US009018017B2

(12) United States Patent
Campbell et al.

(10) Patent No.: US 9,018,017 B2
(45) Date of Patent: Apr. 28, 2015

(54) REAGENTS FOR REDUCING LEUKOCYTE INTERFERENCE IN IMMUNOASSAYS

(71) Applicant: Abbott Point of Care Inc., Princeton, NJ (US)

(72) Inventors: John Lewis Emerson Campbell, Ottawa (CA); Graham Davis, Princeton, NJ (US); John Emegbero Omakor, Stittsville (CA); Adam Roger Moss, Ottawa (CA); Ganesh Guhados, Ottawa (CA)

(73) Assignee: Abbott Point of Care, Inc., Princeton, NJ (US)

( * ) Notice: Subject to any disclaimer, the term of this patent is extended or adjusted under 35 U.S.C. 154(b) by 0 days.

(21) Appl. No.: 13/862,632

(22) Filed: Apr. 15, 2013

(65) Prior Publication Data

US 2013/0273576 A1 Oct. 17, 2013

Related U.S. Application Data

(62) Division of application No. 12/771,634, filed on Apr. 30, 2010, now Pat. No. 8,476,079.

(51) Int. Cl.
*G01N 33/543* (2006.01)
*G01N 33/537* (2006.01)
*G01N 33/53* (2006.01)

(52) U.S. Cl.
CPC ...... *G01N 33/54393* (2013.01); *G01N 33/5375* (2013.01); *G01N 33/5306* (2013.01)

(58) Field of Classification Search
USPC .................. 435/7.1, 7.93, 7.94, 287.1, 287.2; 436/517, 518, 172, 175
See application file for complete search history.

(56) References Cited

U.S. PATENT DOCUMENTS

| | | | |
|---|---|---|---|
| 4,485,175 A * | 11/1984 | Ledis et al. ..................... 436/63 |
| 5,554,339 A | 9/1996 | Cozzette et al. | |
| 6,911,132 B2 | 6/2005 | Pamula et al. | |
| 7,332,327 B2 | 2/2008 | Vikholm et al. | |
| 7,659,122 B2 * | 2/2010 | Guo ................................ 436/10 |
| 7,723,099 B2 | 5/2010 | Miller et al. | |
| 8,084,272 B2 | 12/2011 | Campbell et al. | |
| 8,476,079 B2 * | 7/2013 | Campbell et al. ............. 436/175 |
| 2003/0170881 A1 | 9/2003 | Davis et al. |
| 2005/0054078 A1 | 3/2005 | Miller et al. |
| 2006/0141450 A1 | 6/2006 | Zhang et al. |
| 2006/0160164 A1 | 7/2006 | Miller et al. |
| 2010/0006706 A1 | 1/2010 | Breitsamter et al. |
| 2010/0167308 A1 | 7/2010 | Miller et al. |
| 2010/0167312 A1 | 7/2010 | Miller et al. |
| 2010/0167386 A1 | 7/2010 | Miller et al. |
| 2010/0173396 A1 | 7/2010 | Miller et al. |
| 2010/0203550 A1 | 8/2010 | Miller et al. |
| 2010/0248273 A1 | 9/2010 | Campbell et al. |
| 2011/0117580 A1 | 5/2011 | Campbell et al. |
| 2011/0117581 A1 | 5/2011 | Campbell et al. |
| 2011/0269159 A1 | 11/2011 | Campbell et al. |
| 2011/0306070 A1 | 12/2011 | Campbell et al. |

FOREIGN PATENT DOCUMENTS

| | | |
|---|---|---|
| EP | 0768530 | 4/1997 |
| WO | WO 00/51814 | 9/2000 |
| WO | WO 2004/053115 | 6/2004 |
| WO | WO 2005/026689 | 3/2005 |
| WO | WO 2011/063010 | 5/2011 |
| WO | WO 2011/063012 | 5/2011 |

OTHER PUBLICATIONS

Barnard, et al., J. Chem. Soc. (1966), pp. 227-235.
Skubitz, et al., Blood 65, pp. 333-339 (1985).
International Search Report for PCT/US2011/034121 dated Jul. 4, 2011.
Ginsberg, et al., "Interaction of Mammalian Cells with Polymorphonuclear Leucocytes", Inflammation, vol. 13 (5): pp. 529-542 (1989).
Wines, et al., "The IgC Fc contains distinct Fc receptor (FcR) binding sites: the leukocyte receptors Fc gamma RI and Fc gamma RIIa bind to a region in the Fc distinct from that recognized by neonatal FcR and Protein A", Journal of Immunology, vol. 64, No. 10, May 15, 2000.
International Preliminary Report on Patentability for PCT/US2011/034121 mailed Nov. 15, 2012.
Office Action for corresponding Chinese Appl. No. 201180032709.4 dated May 7, 2014.

\* cited by examiner

*Primary Examiner* — Gail R Gabel

(57) ABSTRACT

Methods and devices for reducing interference from leukocytes in an analyte immunoassay are provided. In one embodiment, a method is provided comprising the steps of amending a biological sample such as a whole blood sample with one or more leukocidal reagents that reduce or eliminate the metabolic activity of leukocytes, and performing an immunoassay on the amended sample to determine the concentration of analyte in the sample. Preferably, the sample is amended with one or more enzymes and optionally one or more enzyme substrates and cofactors.

9 Claims, 25 Drawing Sheets

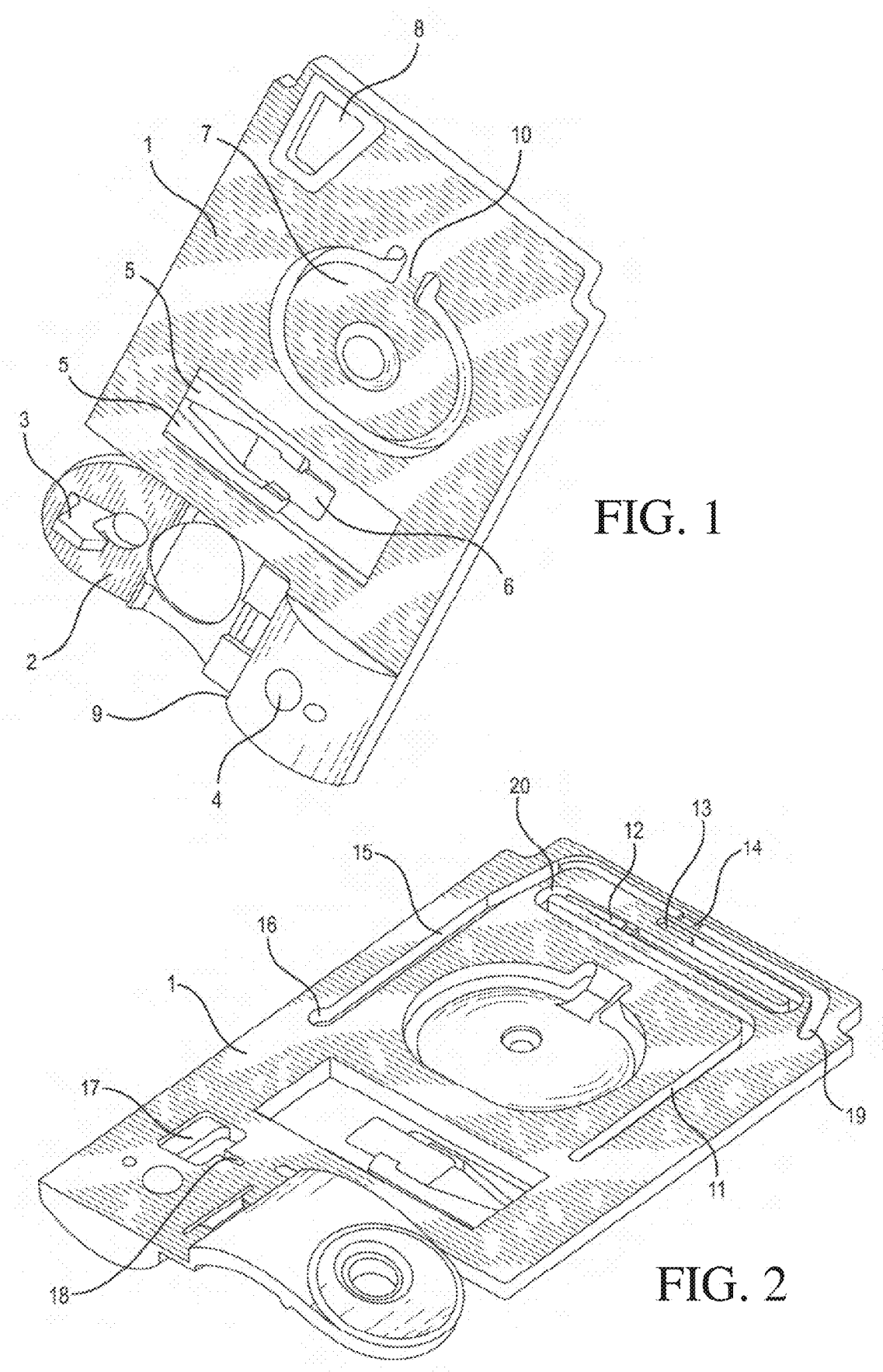

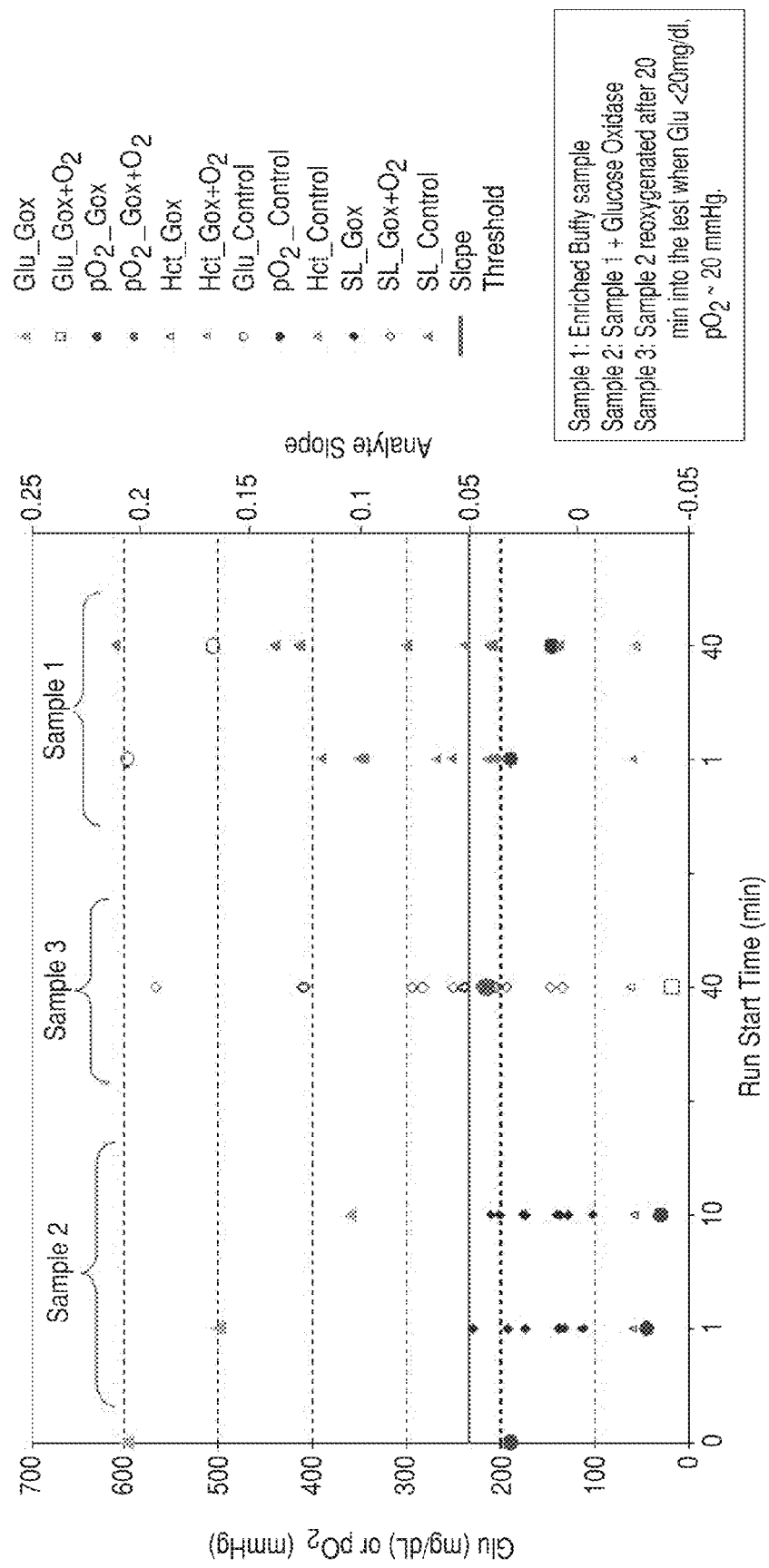
FIG. 28a  Mechanism of Glucose Oxidase Mitigation of Phagocytosis in WBC Enriched Sample

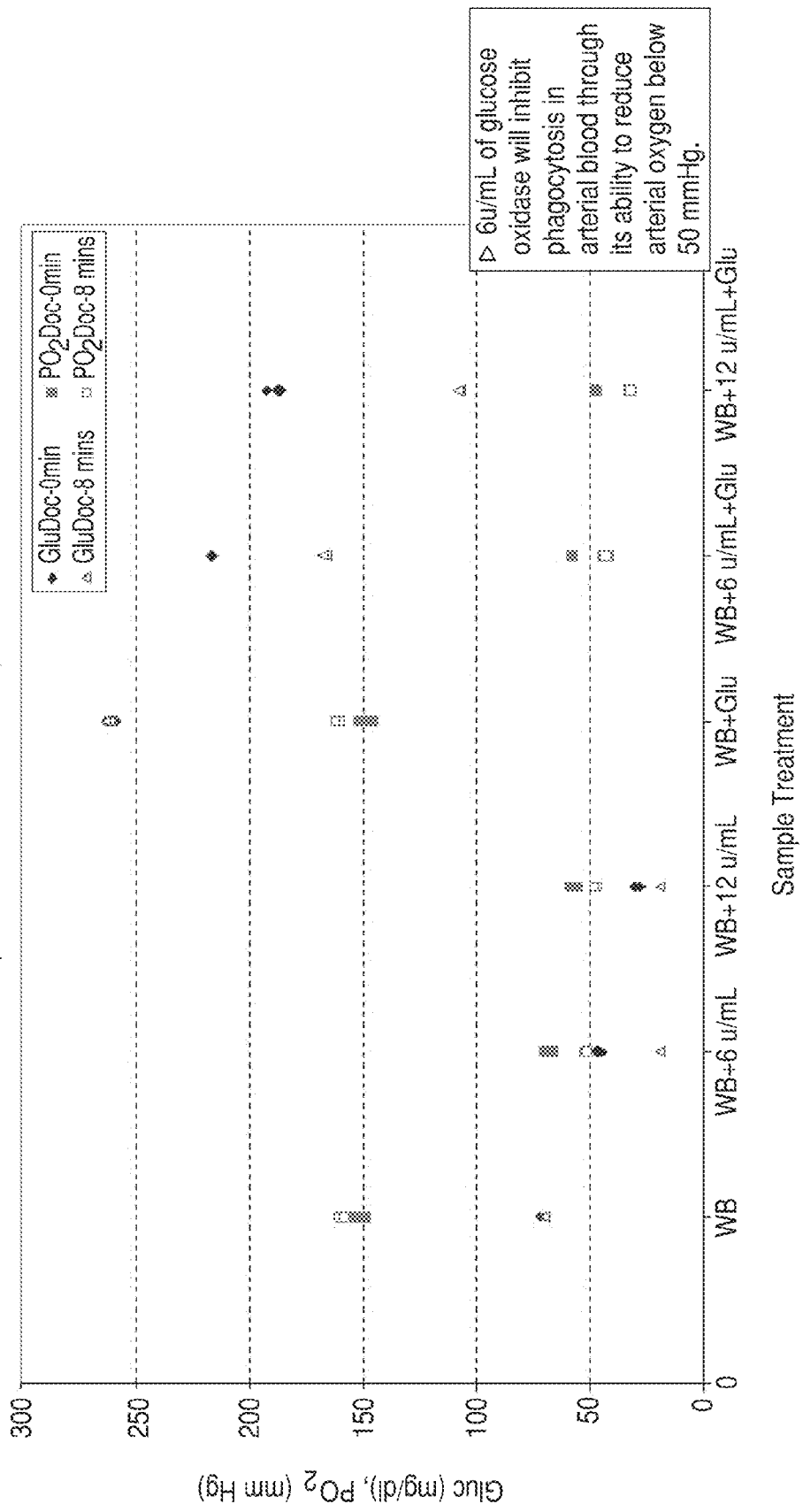

REAGENTS FOR REDUCING LEUKOCYTE INTERFERENCE IN IMMUNOASSAYS

This application is a divisional of U.S. Pat. No. 8,476,079, which issued on Jul. 2, 2013, the entirety of which is incorporated herein by reference.

FIELD OF THE INVENTION

The present invention relates to reducing or eliminating interference from buffy coat components, notably leukocytes, in devices and methods for determining the presence or concentration of an analyte in a blood sample by immunoassay. In particular, the invention relates to reducing or eliminating leukocyte immunosensor interference by amending a blood sample with a leukocidal reagent that reduces or eliminates the activity of leukocytes.

BACKGROUND OF THE INVENTION

A multitude of laboratory immunoassay tests for analytes of interest are performed on biological samples for diagnosis, screening, disease staging, forensic analysis, pregnancy testing and drug testing, among other reasons. While a few qualitative tests, such as pregnancy tests, have been reduced to simple kits for a patient's home use, the majority of quantitative tests still require the expertise of trained technicians in a laboratory setting using sophisticated instruments. Laboratory testing increases the cost of analysis and delays the patient's receipt of the results. In many circumstances, this delay can be detrimental to the patient's condition or prognosis, such as for example the analysis of markers indicating myocardial infarction and heart failure. In these and similar critical situations, it is advantageous to perform such analyses at the point-of-care, accurately, inexpensively and with a minimum of delay.

Many types of immunoassay devices and processes have been described. For example, a disposable sensing device for successfully measuring analytes in a sample of blood is disclosed by Lauks in U.S. Pat. No. 5,096,669. Other devices for successfully measuring features such as for example clotting time are disclosed by Davis et al. in U.S. Pat. Nos. 5,628,961 and 5,447,440. These devices employ a reading apparatus and a cartridge that fits into the reading apparatus for the purpose of measuring analyte concentrations and viscosity changes in a sample of blood as a function of time. The entire contents and disclosures of U.S. Pat. Nos. 5,096,669; 5,628,961; and 5,447,440 are incorporated herein by reference in their entireties.

U.S. Pat. Appl. Pub. 2006/0160164 to Miller et al. describes an immunoassay device with an immuno-reference electrode; U.S. Pat. No. 7,682,833 to Miller et al. describes an immunoassay device with improved sample closure; U.S. Pat. Appl. Pub. 2004/0018577 to Emerson Campbell et al. describes a multiple hybrid immunoassay; and U.S. Pat. No. 7,419,821 to Davis et al. describes an apparatus and methods for analyte measurement and immunoassay, each of which is jointly-owned and is incorporated herein by reference in its entirety.

Non-competitive two-site immunoassays, also called sandwich-type immunoassays, are often employed for determining analyte concentration in biological test samples, and are used for example in the point-of-care analyte detection system developed by Abbott Point of Care Inc., the i-STAT® immunoassay system. In a typical two-site enzyme-linked immunosorbent assay (ELISA), one antibody is bound to a solid support to form an immobilized or capture antibody and a second antibody is conjugated or bound to a signal-generating reagent such as an enzyme to form a signal or labeled antibody. Upon reaction with a sample containing the analyte to be measured, the analyte becomes "sandwiched" between the immobilized antibody and the signal antibody. After washing away the sample and any non-specifically bound reagents, the amount of signal antibody remaining on the solid support is measured and should be proportional to the amount of analyte in the sample.

Electrochemical detection, in which the binding of an analyte directly or indirectly causes a change in the activity of an electroactive species adjacent to an electrode, has also been applied to immunoassays. For a review of electrochemical immunoassays, see Laurell et al., Methods in Enzymology, vol. 73, "Electroimmunoassay", Academic Press, New York, 339, 340, 346-348 (1981).

In an electrochemical immunosensor, the binding of an analyte to its cognate antibody produces a change in the activity of an electroactive species at an electrode that is poised at a suitable electrochemical potential to cause oxidation or reduction of the electroactive species. There are many configurations or arrangements for meeting these conditions. For example, the electroactive species may be attached directly to an analyte, or the antibody may be covalently attached to an enzyme that either produces an electroactive species from an electroinactive substrate or destroys an electroactive substrate. See, M. J. Green (1987), Philos. Trans. R. Soc. Lond. B. Biol. Sci., 316:135-142, for a review of electrochemical immunosensors.

The concept of differential amperometric measurement is well known in the electrochemical art. See, for example, jointly-owned U.S. Pat. No. 5,112,455 to Cozzette et al., which is herein incorporated by reference in its entirety. A version of a differential amperometric sensor combination is disclosed in jointly-owned U.S. Pat. No. 5,063,081 to Cozzette et al. (the "'081 patent"), which is herein incorporated by reference in its entirety. The '081 patent also discloses the use of permselective layers for electrochemical sensors and the use of film-forming latexes for immobilization of bioactive molecules. The use of poly(vinyl alcohol) (PVA) in sensor manufacture is described in U.S. Pat. No. 6,030,827 to Davis et al., which is herein incorporated by reference in its entirety. U.S. Pat. Appl. Pub. 2003/0059954 to Vikholm et al., which is herein incorporated by reference in its entirety, teaches antibodies directly attached to a surface having a biorepellant or biomolecule repellant coating, e.g., PVA, in the gaps between the antibodies on the surface. U.S. Pat. No. 5,656,504 to Johansson et al. teaches a solid phase, e.g., PVA, with antibodies immobilized thereon and is incorporated herein by reference in its entirety, and U.S. Pat. Nos. 6,030,827 and 6,379,883 to Davis et al. teach methods for patterning PVA layers and are incorporated herein by reference in their entireties.

It is well known in the art that immunoassays are susceptible to various forms of interferences. Jointly-owned pending U.S. application Ser. No. 12/411,325 (the "'325 application"), for example, addresses ameliorating interferences from heterophile antibodies by the inclusion IgM into an IgG reagent cocktail. The '325 application is incorporated herein by reference in its entirety.

As immunoassay technology has increasingly been adapted to enter the point-of-care testing market, the use of whole blood as the test medium has increased relative to plasma and serum, which are generally used in central laboratory testing. When whole blood is analyzed, erythrocytes and buffy coat components are present in the assay medium.

Those skilled in the art recognize that the buffy coat is a layer of leukocytes and platelets that forms above the erythrocytes when blood is centrifuged.

It has been found that in certain assays, various assay components, e.g., beads and electrode surfaces, can effectively be opsonized with respect to leukocytes. For example, with respect to an electrode surface, Hill et al. (FEBS 191, 257-263, 1985) opsonized a microvoltammetric electrode with human IgG for the purpose of observing the respiratory burst of a human neutrophil based on electrochemical detection of the superoxide ion.

U.S. Pat. Appl. Pub. 2006/0160164 (the '164 application), referenced above, discusses electrochemical immunosensors, the bias between whole-blood and plasma, and provides that immunoassays for markers such as troponin and the like are generally measured and reported as plasma or serum values. The '164 application teaches that when these immunosensors are used for analysis of whole-blood, either a correction factor or a means for eliminating the bias needs to be employed. The '164 application further teaches that certain aspects of this bias can be eliminated, including the bias in whole-blood electrochemical immunoassays associated with components of the buffy coat, and also the bias associated with hematocrit variations between samples.

As provided in the '164 application, leukocyte (or white cell) interference occurs on immunosensors having beads coated with an analyte antibody, e.g., troponin antibody, and control experiments have shown that this positive bias is absent in plasma samples and in blood samples where the buffy coat has been removed. Thus, it appears that leukocytes are able to stick to the immunosensor and promote non-specific binding of the enzyme-labeled antibodies, which remain bound even after a washing step. In the '164 application, it was shown that this bias could be partially eliminated by adding a small amount of an antibody to human serum albumin during bead preparation. Consequently, when a sample contacts the modified beads, albumin from the sample rapidly coats the beads and once they are coated with a layer of native albumin the leukocytes should not recognize the beads as an opsonized surface.

The '164 application describes an additional solution to the leukocyte interference problem wherein the bias is eliminated by increasing the salt concentration of the blood sample from a normal sodium ion concentration of about 140 mM to above about 200 mM, preferably to about 230 mM. The mechanism that accounts for reduced interference may be that the salt causes osmotic shrinkage of the leukocytes. This interpretation is consistent with the leukocytes' impaired ability to interact with the disclosed immunosensor.

Notwithstanding the above literature, the need remains for improved processes for ameliorating effects of leukocyte activity in immunoassays in at least the following areas: immunosensor interference, most notably in the context of point-of-care testing; electrochemical immunoassays; use of an immunosensor in conjunction with an immuno-reference sensor; whole blood immunoassays; single-use cartridge based immunoassays; non-sequential immunoassays with only a single wash step; and dry reagent coatings.

SUMMARY OF THE INVENTION

The invention is directed to reducing or eliminating leukocyte interference in kits, devices and methods for using kits and devices, that involve immunoassays. According to various embodiments of the invention, samples containing an analyte of interest may be amended with one or more leukocidal reagents that reduce or eliminate the activity of leukocytes, and the resulting amended sample may be analyzed in an immunoassay to determine analyte content and/or concentration without significant leukocyte interference.

In one embodiment, the invention is to a method of performing an immunoassay for a target analyte in a blood sample, comprising contacting a blood sample with a leukocidal reagent, wherein said reagent substantially inhibits activity of leukocytes in the sample, and performing an immunoassay on the sample to detect the target analyte. In some embodiments, the immunoassay is a sandwich assay performed by contacting the sample with an immunosensor comprising an immobilized first antibody to the target analyte, and a labeled second antibody to the target analyte. In other embodiments, the immunoassay is a competitive assay performed by contacting the sample with an immunosensor comprising an immobilized first antibody to the target analyte and to a labeled target analyte.

In another embodiment, the invention is to a kit for performing an immunoassay for a target analyte in a whole blood sample. The kit comprises a leukocidal reagent capable of substantially inhibiting leukocyte activity in the sample, and immunoassay reagents for detecting the target analyte. In some embodiments, the immunoassay is a sandwich assay and wherein the immunoassay reagents comprise an immunosensor comprising an immobilized first antibody to the target analyte, and a labeled second antibody to the target analyte. In other embodiments, the immunoassay is a competitive assay and the immunoassay reagents comprise an immunosensor comprising an immobilized first antibody to the target analyte and to a labeled target analyte.

In preferred embodiments, the leukocyte activity that is to be inhibited is phagocytosis. In certain embodiments of the invention, the leukocidal reagent is an oxygen depleting reagent and/or a glucose depleting reagent. For example, the reagent may comprise glucose oxidase. In additional embodiments, the leukocidal reagent comprises glucose oxidase and glucose. In some embodiments, the leukocidal reagent comprises glucose oxidase and glucose, and the reagent mixes with the sample to provide a glucose oxidase activity above about 3 IU per mL and a glucose concentration above about 500 mg/dL. In other embodiments, the leukocidal reagent comprises glucose oxidase and an electron acceptor. In still other embodiments, the leukocidal reagent comprises hexokinase and a source of adenosine-5'-triphosphate (ATP). In other embodiments, the reagent comprises hexokinase, creatine kinase, adenosine diphosphate (ADP), and creatine phosphate. In some embodiments, the leukocidal reagent comprises glucose dehydrogenase and in yet others, the reagent comprises glucose dehydrogenase, NAD, NADH oxidase, and an electron acceptor. In other embodiments of the invention, the leukocidal reagent is an oxygen depleting reagent. In specific embodiments, the leukocidal reagent is an oxygen depleting reagent selected from the group consisting of dithionite, glucose oxidase, and ascorbate oxidase. In additional embodiments, the leukocidal reagent is a mitochondrial electron transport inhibitor and in others, the reagent is a mitochondrial membrane uncoupling agent. In other embodiments, the leukocidal reagent is selected from the group consisting of cyanide, antimycin, rotenone, malonate, carbonyl cyanide p-[trifluoromethoxyl]-phenyl-hydrozone, 2,4-dinitrophenol, and oligomycin. In others, the leukocidal reagent is an amphipathic reagent. In still other embodiments, the leukocidal reagent is an amphipathic reagent and is a saponin. In other embodiments, the reagent is a leukocidin and in further embodiments, the reagent is a mucopolysaccharide. In certain embodiments, the leukocidal reagent is an AHN-1 antibody and in others, the reagent is lipocortin-1.

In some embodiments, in addition to being contacted with the leukocidal reagent, the sample may be contacted with beads opsonized for leukocytes. For example, in one aspect, the leukocidal reagent comprises glucose oxidase and glucose, and the sample is contacted with beads opsonized for leukocytes. In preferred embodiments of the invention, the sample is a whole blood sample. The sample may be amended with an anticoagulant. In some optional embodiments, the analyte is selected from the group consisting of TnI, TnT, BNP, NTproBNP, proBNP, HCG, TSH, NGAL, theophylline, digoxin, and phenyloin.

BRIEF DESCRIPTION OF THE DRAWINGS

These and other objectives, features and advantages of the present invention are described in the following detailed description of the specific embodiments and are illustrated in the following Figures, in which:

FIG. 1 is an isometric top view of an immunosensor cartridge cover;

FIG. 2 is an isometric bottom view of an immunosensor cartridge cover;

FIG. 28(a) shows the use of glucose oxidase in reducing the effect of leukocyte activity on the signal output slope of an immunosensor where the sample is retained in a closed container versus open to ambient air;

FIG. 29 shows the effect of glucose oxidase on simulated arterial blood samples.

DETAILED DESCRIPTION OF THE INVENTION

Figure 3:
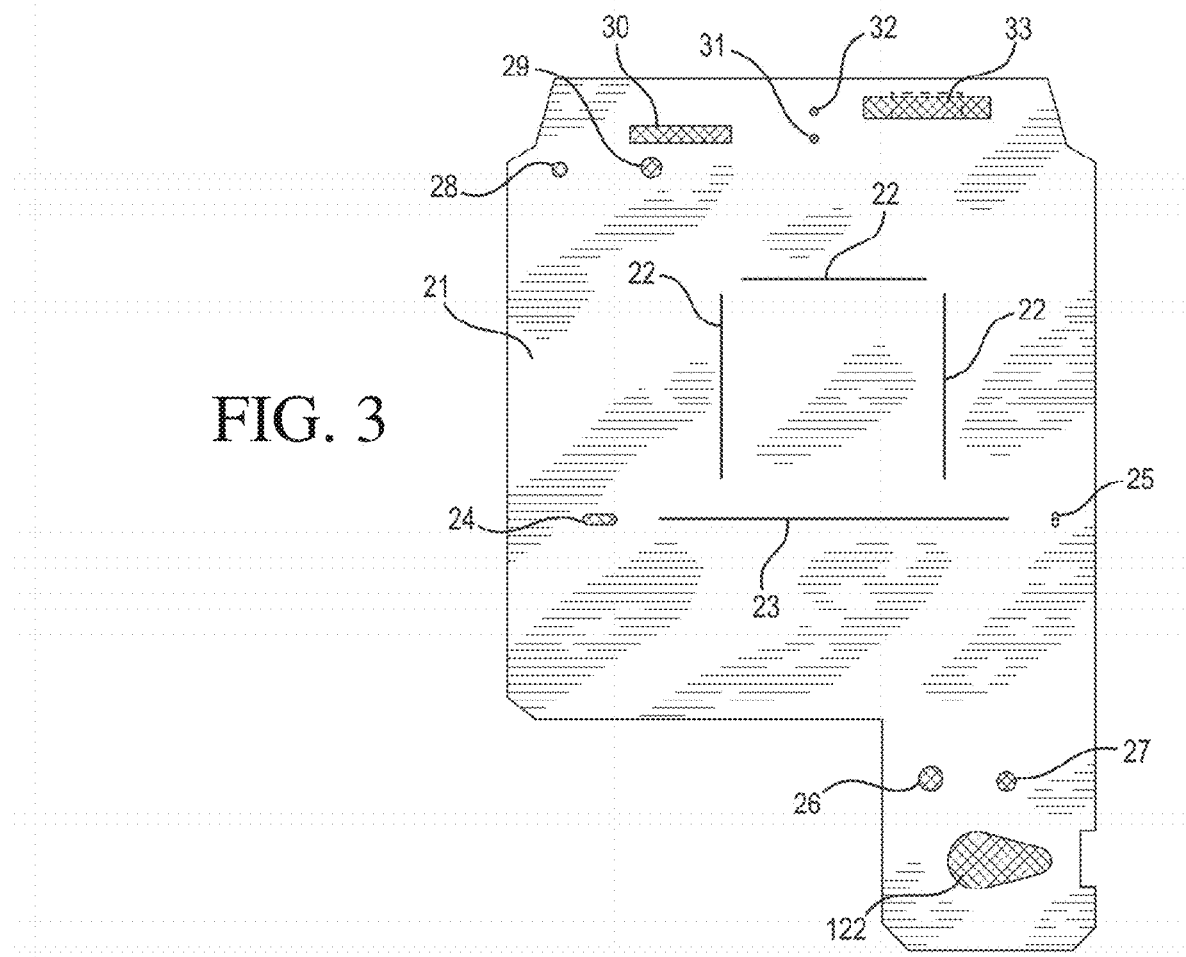
FIG. 3 is a top view of the layout of a tape gasket for an immunosensor cartridge.

The present invention relates to the use of leukocidal reagents to reduce or eliminate interference caused by the presence of leukocytes in immunoassays. In preferred embodiments, the present invention may be employed in one or more of the following areas: immunosensors, most notably in the context of point-of-care testing; electrochemical immunoassays; the use of an immunosensor in conjunction with an immuno-reference sensor; whole blood immunoassays; single-use cartridge based immunoassays; non-sequential immunoassays with only a single wash step; and dry reagent coatings. Notably, while U.S. Pat. Appl. Pub. 2006/0160164 (the '164 application), referenced above, addresses certain interferences associated with leukocytes based on the addition of an anti-human serum, albumin antibody coating on an immunosensor, and the addition of salts to the assay medium, the present specification discloses additional sources of bias associated with leukocytes and provides a novel solution for reducing same. As will be appreciated by those skilled in the art, the general concept disclosed herein is applicable to many immunoassay methods and platforms.

The present invention permits rapid in situ determinations of analytes using a cartridge having an array of analyte sensors and means for sequentially presenting an amended sample to an immunosensor or analyte array. In preferred embodiments, the invention is employed in cartridges that are designed to be operated with a reading device, such as that disclosed in U.S. Pat. No. 5,096,669 to Lauks et al., issued Mar. 17, 1992 (referenced above), or U.S. Pat. No. 7,419,821 to Davis et al., issued Sep. 2, 2008 (referenced above), both of which are incorporated by reference herein in their entireties. The invention is best understood in this context. Consequently, a suitable device and method of operation for a point-of-care immunoassay system is first described, followed by how the system may be best adapted to further reduce or eliminate leukocyte interference in whole blood immunoassays.

In various embodiments, the invention is employed in a heterogeneous electrochemical immunoassay based on the formation of a sandwich at or near the electrode surface. In other embodiments, however, the invention is to other forms of immunoassay. For example, the leukocidal reagents of the present invention may be employed in either heterogeneous or a homogeneous bead-based assays, as well as in non-competitive (sandwich) immunoassays or competitive immunoassays. In this context, the terms "heterogeneous" and "homogeneous" refer to the capture step. Hence, for homogeneous assays, the capture step occurs in the fluid medium, while in heterogeneous assays, the capture step occurs on a macroscopic surface, e.g., sensor surface (in either a competitive or non-competitive manner). In each of these examples, the immobilized assay beads will be susceptible to attack by leukocytes when the assay is performed in a blood sample. In competitive and non-competitive assays, this effect can be reduced by the addition of leukocidal reagents and optionally sacrificial beads opsonized for leukocytes.

Figure 24:
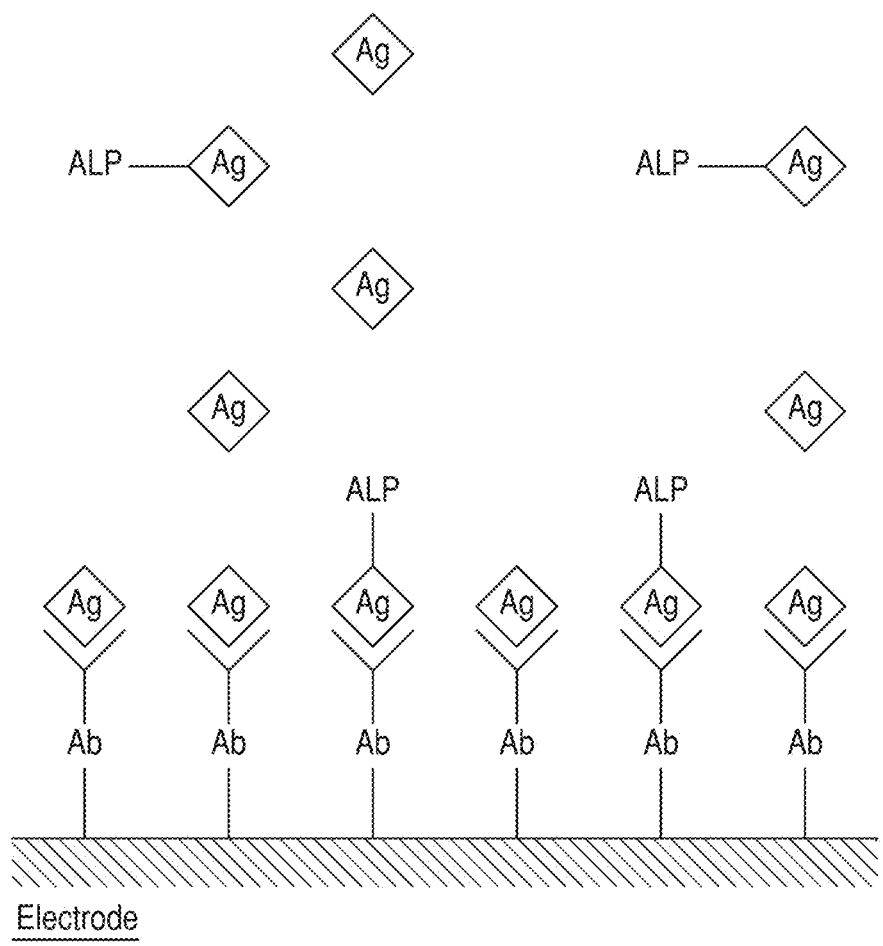
FIG. 24 illustrates a competitive immunoassay, which may be amended with sacrificial beads according to one embodiment of the invention.

In a heterogeneous competitive assay, illustrated in FIG. 24, an (unlabeled) analyte present in a sample competes with a labeled analyte for binding sites on a solid surface, e.g., a sensor element. A sample suspected of containing the analyte of interest (sample analyte) is amended with a quantity of a reagent comprised of the same analyte conjugated to a label, i.e., the labeled analyte. The label may be a dye or any signal-generating element, such as an enzyme, e.g., ALP. In some exemplary embodiments, the labeled analyte may be labeled with a label selected from the group consisting of a radiolabel, an enzyme, a chromophore, a fluorophore, a chemiluminescent species, an ionophore and an electroactive species. In another embodiment, the labeled analyte is labeled with a label selected from the group consisting of a fluorescein, a ferrocene (optionally a carboxylated ferrocene or dicarboxylated ferrocene or aminoferrocene), and a p-aminophenol.

Analytes commonly identified and/or measured by means of competitive assay include the therapeutic agents such as, for example, digoxin, theophylline and biomarkers such as for example C-reactive protein (CRP) as well as phenobarbital, phenyloin, valproic acid and vancomycin. In preferred aspects, the sample analyte is selected from the group consisting of digoxin, phenobarbital, phenyloin, theophylline, valproic acid and vancomycin. In one embodiment of the invention, the amended sample is brought into contact with a solid surface on which is immobilized an antibody to the analyte of interest. The sample-borne analyte and the labeled analyte compete for binding at this solid surface so that the amount of labeled analyte and hence the amount of signal generated therefrom will be inversely proportional to the concentration of analyte in the original sample. After washing non-specifically bound material from the sensor surface, the amount of label is measured; in the case of an enzyme label, this would involve supplying a suitable substrate to the enzyme and detecting the product, e.g., electrochemically or optically. When employed in a heterogeneous competitive immunoassay, the blood sample preferably is amended with a leukocidal reagent prior to contacting the solid surface, i.e., sensor. If desired, the blood sample may be further amended with sacrificial beads opsonized to leukocytes (e.g., IgG-coated microparticles) prior to contacting the solid surface, as described in U.S. patent application Ser. Nos. 12/620,179 and 12/620,230, both filed Nov. 17, 2009, the entireties of which are incorporated herein by reference.

I. Cartridge

In one embodiment, the invention relates to cartridges and methods for processing liquid samples to determine the presence or amount of an analyte in the sample. The cartridges preferably contain a metering means, which permits an unmetered volume of sample to be introduced, from which a metered amount is processed by the cartridge and its associated reading apparatus. Thus, the physician or operator is relieved of manually measuring the volume of the sample prior to measurement thereby saving time, effort, and increasing accuracy and reproducibility. The metering means, in one embodiment, comprises an elongated sample chamber bounded by a capillary stop and having along its length an air entry point. Air pressure exerted at the air entry point drives a metered volume of the sample past the capillary stop. The metered volume is predetermined by the volume of the sample chamber between the air entry point and the capillary stop.

The cartridge may have a closure device for sealing the sample port in an air-tight manner. This closure device is preferably slidable with respect to the body of the cartridge and may provide a shearing action that displaces excess sample located in the region of the port, thereby reliably sealing a portion of the sample in the holding chamber between the entry port and the capillary stop. See, for example, U.S. Pat. No. 7,682,833, the entirety of which is incorporated herein by reference. In one embodiment, the cartridge may be sealed, for example, by slidably moving a sealing element over the surface of the cartridge in a manner that displaces excess fluid sample away from the sample orifice, seals a volume of the fluid sample within the internal fluid sample holding chamber, and inhibits fluid sample from prematurely breaking through the internal capillary stop. The seal obtained by this slidable closure device is preferably irreversible and prevents excess blood from being trapped in the cartridge because the closure device moves in the plane of the orifice through which blood enters the cartridge and provides a shearing action that seals blood below the plane of the entry port, thereby moving excess blood, i.e., blood above the plane of the orifice, away from the entry port and optionally to a waste chamber.

Figure 18:
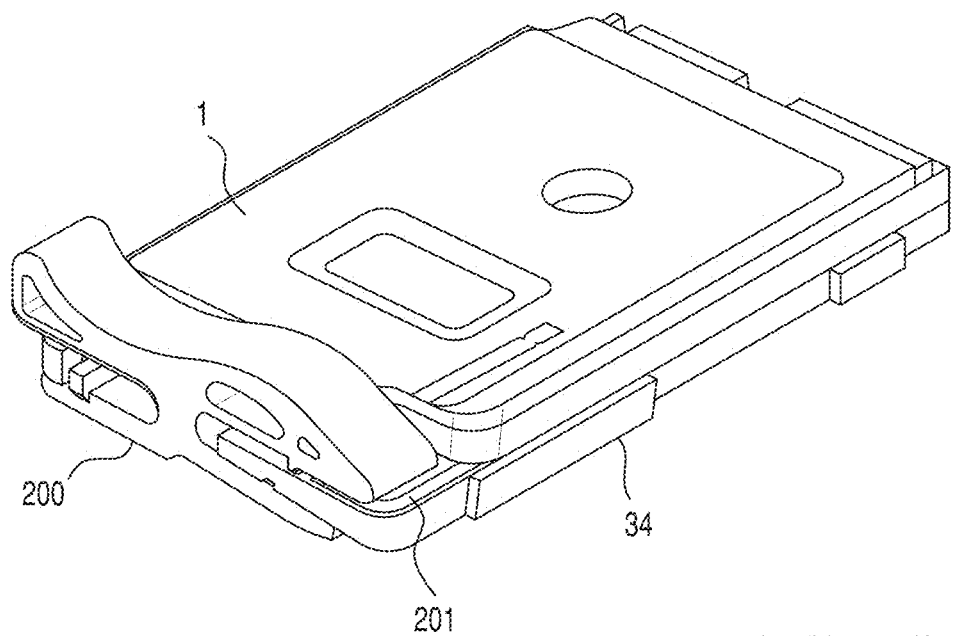
FIG. 18 illustrates the cartridge device with a slidable sealing element for closing the sample entry port in the closed position.
Figure 19:
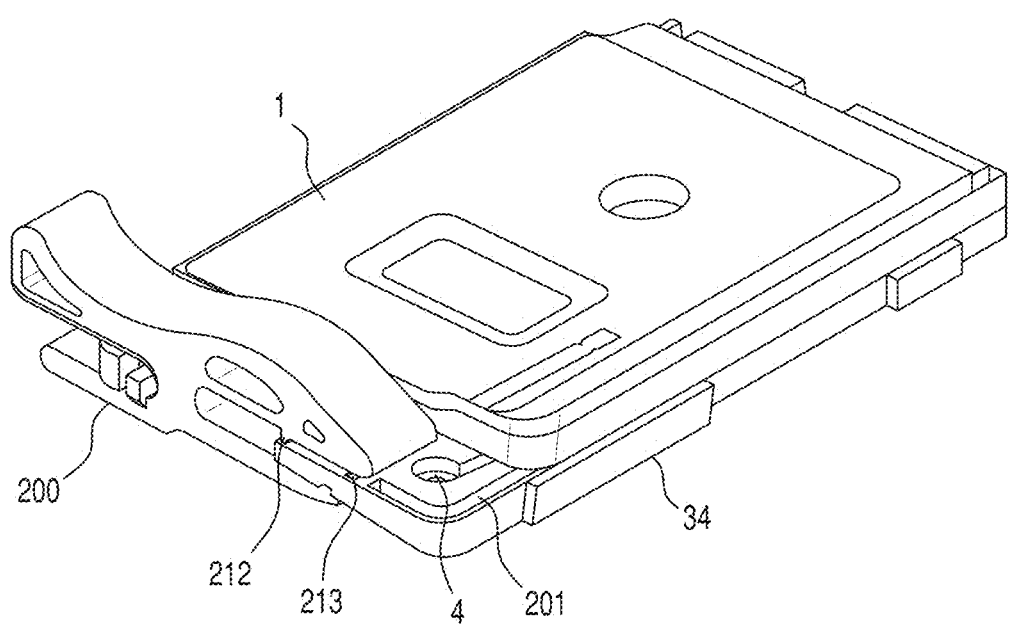
FIG. 19 illustrates the cartridge device with a slidable sealing element for closing the sample entry port in the open position.

An exemplary closure device of one embodiment of the present invention is shown in FIG. 1 and comprises integrated elements 2, 3, 4 and 9 of cover 1. In this embodiment, closure device 2 rotates about a hinge until hook 3 snaps shut blocking sample entry port 4. An alternative to the closure device comprising integrated elements 2, 3, 4 and 9 of cover 1 in FIG. 1 is shown as a separate slidable element 200 in FIGS. 18 and 19. FIGS. 18 and 19 show a cartridge device comprising a modified version of the cover of FIG. 1 attached to a base similar to the base in FIG. 4 with intervening adhesive layer 21 shown in FIG. 3 along with the separate slidable closure element 200. FIG. 19 shows the closure device 200 in the open position, where the sample entry port 4 can receive a sample, e.g., blood. FIG. 18 shows the closure device 200 in the closed position where it seals the sample entry port in an air-tight manner. In operation, element 200 is manually actuated from the open to the closed position after the sample, e.g., blood, has been added to the entry port and it enters the holding chamber 34. In the embodiment shown, any excess blood in the region of the entry port is moved into an overflow chamber 201 or an adjacent retaining region or cavity. This chamber or region may include a fluid-absorbing pad or material to retain the excess sample, e.g., blood.

The sample entry port 4 may be an orifice that is circular, as shown in FIG. 19, or oval and the diameter of the orifice is generally in the range 0.2-5 mm, preferably 1-2 mm, or having a perimeter of 1-15 mm for an oval. The region around the orifice may be selected to be hydrophobic or hydrophilic to control the drop-shape of the applied sample to promote entry into the entry port. One advantage of the closure device shown in FIGS. 18 and 19 is that it prevents the sample from being pushed beyond the capillary stop element 25 at the end of the holding chamber 34. The presence of a small amount of sample, e.g., blood, beyond the capillary stop is not significant for tests that measure bulk concentration of an analyte and thus do not depend on sample volume. However, for immunoassay applications where metering of the sample is generally advantageous the sealing element improves metering accuracy of the device and assures the assayed segment of sample is appropriately positioned with respect to the immunosensor when the analyzer actuates the sample within the cartridge conduits.

In operation, when the sample, e.g., blood, is added to the cartridge it moves to the capillary stop. Thus, sufficient sample for the assay is present when the region from the capillary stop to the sample entry port, i.e., the holding chamber 34, contains the sample. During the process of filling the holding chamber, some sample may remain above the plane of the orifice of the entry port. When the sealing element is moved from the opened to closed position, any sample that is above the entry port is sheared away without trapping additional sample in the act of closure, thereby ensuring that the sample does not move beyond capillary stop 25. In a preferred embodiment, sealing element 200 is positioned within a few thousandths of an inch above the surface of the tape gasket 21 of FIG. 3. The entry port is sealed by the subsequent lowering of the surface of 200 to the adhesive tape gasket when it engages locking features 212 and 213. As the tape is essentially incompressible and the orifice has a small diameter, any inadvertent pressure applied to the sealing element by the user will not cause the sample to move beyond the capillary stop.

In certain cartridge embodiments that use several drops of sample, it is desirable that no bubbles form in the holding chamber as this can affect the assay. Accordingly, a reliable means for introducing more than one drop of sample, e.g., blood, into the holding chamber 34 without entraining bubbles has been developed. In accordance with one embodiment of the invention, the sample entry port can be designed to receive multiple drops of sample without successive drops causing trapped bubbles to form in the holding chamber 34 by first treating the holding chamber with a Corona and/or a reagent cocktail.

The use of Corona treatments on disposable medical devices is well known in the art and is an effective way to increase the surface activity of virtually any material, e.g., metallized surfaces, foils, paper, paperboard stock, or plastics such as polyethylene, polypropylene, nylon, vinyl, polyvinyl chloride (PVC), and polyethylene terephthalate (PET). The Corona treatment makes the materials more receptive to inks, coatings, and adhesives. In practice, the material being treated is exposed to an electrical discharge, or "corona." Oxygen molecules in the discharge area break into atoms and bond to molecules in the material being treated, resulting in a chemically activated surface. Suitable equipment for corona treatments is commercially available (e.g., Corotec Corporation, Farmington, Conn., USA). The process variables are well known and include the amount of power required to treat the material, the material speed, the width, the number of sides to be treated, and the responsiveness of a particular material to corona treatment, which variables can be determined by a skilled operator. The typical place to install a corona treatment is in-line with the printing, coating, or laminating process. Another common installation is directly on a blown film or cast film extruder, because fresh material is more receptive to corona treatment.

II. Signal Generating Reactions

As described above, the non-competitive (sandwich) immunoassay format is the most widely used immunoassay method and it is also a preferred format in the analysis device, e.g., cartridge, discussed herein. In this embodiment, one antibody (the immobilized antibody) is bound to a solid support or immunosensor, and a second antibody (the signal antibody) is conjugated/bound to a signal-generating reagent such as an enzyme, e.g., alkaline phosphatase.

Figure 20:
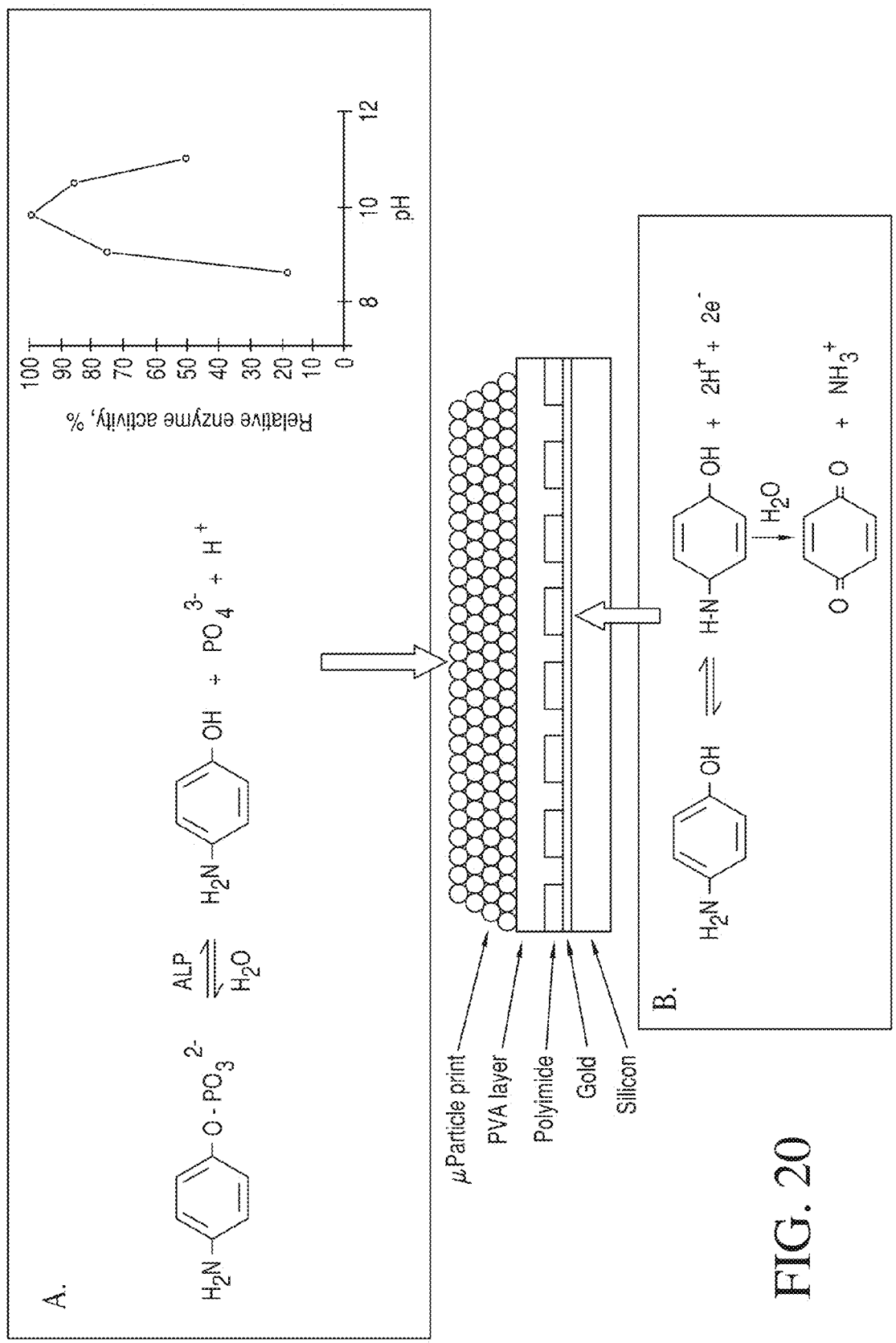
FIG. 20 illustrates the signal generating reactions occurring during the analysis: (a) cleavage of substrate by alkaline phosphatase to generate electroactive p-aminophenol and (b) oxidation of p-aminophenol.

Briefly, FIG. 20 illustrates the signal generating reactions occurring during the analysis with FIG. 20(*a*) showing the cleavage of substrate by alkaline phosphatase to generate electroactive p-aminophenol and FIG. 20(*b*) showing oxidation of p-aminophenol. The reaction in FIG. 20(*a*) occurs in the upper layer of the sensor structure while that in FIG. 20(*b*) occurs at the gold electrode surface. The inset in FIG. 20(*a*) illustrates the pH-dependence of the alkaline phosphatase catalyzed hydrolysis. The central illustration depicts the gross features of the immunosensor structure prior to exposure to sample.

The signal-generating reagent (e.g., signal antibody for non-competitive assays or labeled analyte for competitive assays) may be part of a dry reagent coating in the analysis device, as described below, and preferably dissolves into the biological sample before the sample reaches the immunosensor. For non-competitive assays, after washing away the sample and non-specifically bound reagents, the amount of signal-generating reagent (e.g., signal antibody) remaining on the solid support should in principle be proportional to the amount of analyte in the sample. For competitive assays, as discussed above, after washing away the sample and non-specifically bound reagents, the amount of signal-generating reagent (e.g., labeled analyte) remaining on the solid support should in principle be inversely proportional to the amount of analyte in the sample. However, one limitation of these assay configurations is the susceptibility to interference(s) caused by leukocytes present in the blood sample.

III. Leukocidal Reagents

While leukocyte interferences have been mitigated by the means disclosed in jointly-owned U.S. Pat. Appl. Pub. 2006/0160164 to Miller et al., referenced above, it has now been discovered that for certain blood samples, leukocidal activity in a sample, e.g., blood sample, may be surprisingly and unexpectedly reduced or eliminated by the addition of one or more leukocidal reagents. Thus, in contrast with conventional processes for mitigating leukocyte interference, in various embodiments of the invention, leukocyte activity may be substantially reduced or eliminated with a leukocidal reagent, defined herein as any composition that is capable of metabolically or amphipathically reducing or eliminating leukocyte activity. As discussed below, a non-limiting list of examples of leukocidal reagents includes enzymes and their co-reagents, saponins, cytotoxins, mucopolysaccharides, leukocidins and anti-leukocyte antibodies. In many embodiments, the leukocidal reagent is an organic, optionally nonionic, species, while in others the reagent may be inorganic and ionic (e.g., cyanide, dicyanate-containing reagents or dithionite species).

Without being bound by theory, the process of phagocytosis involves an oxidative burst by the leukocytes to generate oxygen radical species, such as superoxide and hydroxyl radicals, that attack a xenobiotic entity, e.g., bacteria. As phagocytosis is an oxygen-dependent process, reducing the bulk oxygen concentration in the sample can be used as a means to prevent or ameliorate leukocyte interference in an immunoassay. Likewise, impeding the metabolic path of these cells in other ways is also a useful approach to reducing leukocyte interference. In other embodiments, as described below, sacrificial beads may be used in combination with the leukocidal reagents to reduce or eliminate leukocidal activity.

Several approaches are possible for the metabolic inhibition of leukocytes. In one embodiment, the leukocytes are deprived of oxygen that is available in plasma, for example, by using an added enzyme such as glucose oxidase to consume the glucose and make hydrogen peroxide. This deprives the cells of oxygen, which is the terminal electron acceptor in the respiratory chain. Note that any peroxide in the sample will quickly be dismutated by catalase to oxygen and water, but the net driving force of the reaction substantially removes all the oxygen from the sample.

In another embodiment, substantially all of the glucose is removed from the plasma fraction of the sample. In general, the bulk oxygen concentration in the blood sample will generally be much lower than the glucose concentration ($[O_2]$ ~100 μM; [glucose]~5-10 mM). Thus, the addition of a soluble electron acceptor for glucose oxidase such as, for example, ferrocenium monocarboxylic acid, phenazine methosulphate, or N,N,N',N'-tertramethyl-p-phenylene diamine, is desirable for removing substantially all the glucose. Alternatively, a glucose dehydrogenase (GDH) can be used; however addition of the cofactor NAD+ is required, with the exception of a GDH with the PQQ cofactor. In this example NADH oxidase (diaphorase) can also be added along with an electron acceptor, as indicated above. In another embodiment, hexokinase may be added, which phosphorylates the available glucose in the sample. Here, a source of ATP is required, which is preferably made in situ by adding creatine phosphate, ADP and creatine kinase. In this example only the bulk glucose concentration is affected and not the oxygen concentration.

Generally, it has been found that it is more effective to remove substantially all of the oxygen rather than substantially all of the glucose in the plasma fraction of the sample. This is related to the fact that the cells already have stored energy (reducing equivalent), but substantially lack an "oxygen store." Particular embodiments are directed to the elimination of oxygen though a chemical means, for example, by the addition of an excess of dithionite, or enzymatically by the addition of ascorbate oxidase, which reduces oxygen directly to water.

In some embodiments, the invention is directed to methods of performing an immunoassay for a target analyte in a blood sample. In one aspect, the method comprises the step of contacting a sample, e.g., a blood sample, with a leukocidal reagent, wherein the reagent substantially inhibits activity of leukocytes in the sample, and performing an immunoassay on the sample to detect a target analyte. In certain embodiments of the invention, the reagent is an oxygen depleting regent or a glucose depleting reagent or both. In one aspect, the reagent comprises glucose oxidase. In other aspects, the reagent comprises glucose oxidase and glucose. In other embodiments, the leukocidal reagent comprises glucose oxidase and glucose, and the leukocidal reagent mixes with the sample to provide a glucose oxidase activity above about 3 IU per mL and a glucose concentration above about 500 mg/dL.

As indicated above, another approach to reducing leukocyte interference is to use an electron transport inhibitor or uncoupling agents that inhibit the mitochondria within the leukocytes. Thus, in one aspect, the leukocidal reagent comprises an electron transport inhibitor. Suitable electron transport inhibitors and uncoupling agents include, but are not limited to, rotenone, antimycin, cyanide, malonate (a succinate dehydrogenase inhibitor), 2,4-dinitrophenol (DNP), carbonyl cyanide p-[trifluoromethoxy]-phenyl-hydrazone (FCCP) and oligomycin (an inhibitor of oxidative phosphorylation). While malonate and cyanide can be added directly to the sample (for example in reagent coating in an immunoassay device), other electron transport inhibitors and uncoupling agents may require addition of ethanol or similar solvent to aid dissolution in the plasma fraction.

Without being bound by theory, electron transport inhibitors generally act by binding along the electron transport chain, thus preventing electrons from being passed from one molecule in the sequence to the next. The mechanism of inhibition can be along the NADH pathway, the succinate pathway, or the common pathway. For example, cyanide is an effective reversible inhibitor of cytochrome oxidase which is the terminal enzyme in the common pathway. Specifically, a concentration of about 1 mM KCN (optionally from 0.5 to 50 mM) should be sufficient to substantially inhibit oxygen consumption in mitochondria present in a human blood sample.

Uncoupling agents act by interfering with the chemiosmotic gradient. For example, 2,4-dinitrophenol works as a proton ionophore, binding to protons on one side of the membrane, and being lipophilic, transports the protons across the membrane. Thus, the respiratory chain is prevented from maintaining a proton gradient across the membrane. Carbonyl cyanide p-[trifluoromethoxyl]-phenyl-hydrozone (FCCP) also works in this manner. Oligomycin has a related effect and acts by binding ATP synthase in such a way as to block the proton channel, thus inhibiting oxidative phosphorylation. The use of these agents is also beneficial for ameliorating interference based on any anaerobic leukocyte activity. Specifically, even when the cells are deprived of oxygen, conversion of glucose to lactate still can yield ATP, unless the uncoupling agents are used.

In some embodiments of the invention, the reagent is glucose oxidase and an electron acceptor. In still other embodiments, the reagent comprises hexokinase and a source of adenosine-5'-triphosphate (ATP). In other embodiments, the reagent comprises hexokinase, creatine kinase, adenosine diphosphate (ADP), and creatine phosphate. In some embodiments, the reagent comprises glucose dehydrogenase and in yet others, the reagent comprises glucose dehydrogenase, NAD, NADH oxidase, and an electron acceptor. In other embodiments of the invention, the reagent is an oxygen depleting reagent. In others, the reagent is an oxygen depleting reagent selected from the group consisting of dithionite, glucose oxidase, and ascorbate oxidase. In additional embodiments, the reagent is a mitochondrial electron transport inhibitor and in others, the reagent is a mitochondrial membrane uncoupling agent. In other embodiments, the reagent is selected from the group consisting of cyanide, antimycin, rotenone, malonate, carbonyl cyanide p-[trifluoromethoxyl]-phenyl-hydrozone, 2,4-dinitrophenol, and oligomycin. In others, the reagent is an amphipathic reagent.

A preferred approach for reducing or eliminating phagocytic activity of leukocytes towards an immunosensor is based on the addition of saponin, e.g., from Quillaja bark, which is an amphipathic reagent. The saponin acts as a surfactant and hemolytic agent that enhances transport of proteins and other macromolecules through the cell membrane.

In an alternative embodiment of the invention, a leukocidin may be used as the leukocidal reagent. Leukocidin is a type of cytotoxin from bacteria, e.g., Panton-Valentine leukocidin. Leukocidin is a pore forming toxin capable of killing leukocytes. See, for example, Hongo et al., Journal of Infectious Diseases 200, 715-723, (2009).

In another embodiment, a mucopolysaccharide, e.g., heparin, may be used to induce leukocyte lysis. See, for example, Adachi et al, J Pharmacobio-Dyn 9, 207-210 (1986).

In certain embodiments, the leukocidal reagent is an AHN-1 antibody. In other embodiments of the invention, the leukocidal reagent is lipocortin-1 or an equivalent thereof.

In still other embodiments, the leukocidal reagent as described herein can be used in conjunction with beads opsonized for leukocytes. In one preferred embodiment, the leukocidal reagent comprises glucose oxidase and glucose, and this leukocidal reagent is used in conjunction with beads opsonized for leukocytes.

In a preferred embodiment, the one or more leukocidal reagents are incorporated into a dry reagent coating, while in other embodiments, the leukocidal reagents are provided in a separate reagent fluid, e.g., in a fluid pouch for mixing with the sample. If provided as a dry reagent, the one or more leukocidal reagents may be provided in the same dry reagent coating that contains the signal-generating reagent (e.g., signal antibody for non-competitive assays or labeled analyte for competitive assays). Thus, in one embodiment of the invention, the analysis device includes a dry reagent coating that comprises either or both: (a) one or more leukocidal reagents, and/or (b) a signal-generating reagent such as a signal antibody or a labeled analyte. The dry reagent coating may be formed from a reagent cocktail, which also preferably comprises either or both: (a) one or more leukocidal reagents, and/or (b) a signal-generating reagent such as a signal antibody or a labeled analyte. In some embodiments, the reagent coating and/or cocktail further comprises one or more of: (a) IgM or fragments thereof for ameliorating interference caused by heterophile antibodies, as disclosed in co-pending U.S. application Ser. No. 12/411,325, referenced above, and/or (b) sacrificial beads opsonized for leukocytes (discussed below), as described in previously discussed U.S. patent application Ser. Nos. 12/620,179 and 12/620,230. The surface on which the reagent cocktail is to be deposited preferably is first Corona treated to provide charged surface groups that will promote spreading of the printed cocktail.

In some embodiments, the reagent cocktail used to form the dry reagent coating may further comprise one or more of a water-soluble protein, an amino acid, a polyether, a polymer containing hydroxyl groups, a sugar or carbohydrate, a salt and optionally a dye molecule. In one embodiment, the cocktail contains bovine serum albumin (BSA), glycine, salt, methoxypolyethylene glycol, sucrose and optionally a visualization agent such as for example bromophenol blue to provide color that aids visualizing the printing process. In another embodiment, from 1 to 20 μL of cocktail is printed onto the desired surface, e.g., within the holding chamber or other conduit, of the analysis device and allowed to air dry (with or without heating) before being assembled with its cover. In a preferred embodiment, the reagent cocktail and the dry reagent coating formed therefrom comprise lactitol, DEAE-dextran, salts such as magnesium and sodium chloride, IgG/IgM, heparin, surfactant(s) and rhodamine.

In other embodiments of the invention, the cartridge may comprise a plurality of dry reagent coatings (in which case the coatings may be respectively referred to as a first reagent coating, a second reagent coating, etc., in order to distinguish them). For example, the leukocidal reagent may be included in a first reagent coating, which, for example, may be adjacent to a second reagent coating that contains the signal generating element, e.g., signal antibody for non-competitive assays or labeled analyte for competitive assays. In this aspect, the second reagent coating may be located upstream or downstream of the first reagent coating, although it is preferable for the reagent coating that contains the signal generating element to be located downstream of the reagent coating that contains the sacrificial beads. In a preferred embodiment, the holding chamber is coated with a first reagent coating that comprises the leukocidal reagent and optionally other reagents, e.g., sacrificial beads, that ameliorate various forms of interference. In this aspect, a second reagent coating comprising the signal generating element preferably is located downstream of the holding chamber, e.g., immediately upstream of the immunosensor.

In some embodiments, a reagent cocktail preferably is formulated as a printable aqueous solution containing the leukocidal reagent and optionally other interference-reducing reagents, e.g., sacrificial beads. Upon introduction of a biological sample, e.g., blood, the sample preferably mixes with the reagent in a first step of the assay. In some embodiments, the reagent may also include inorganic salts and surfactants to optimize assay performance with respect to chemical and fluidic attributes. In further embodiments, the reagent may include optional additives such as an anticoagulant or anticoagulation agent (e.g., heparin) to ensure adequate anticoagulation and/or a visualization agent (e.g., a dye or colorant) for visualization of the location of the reagent after printing. Also optionally present are stabilizers such as sodium azide for inhibition of microbial growth and a mixture of lactitol and diethylaminoethyl-dextran (Applied Enzyme Technologies Ltd., Monmouth House, Mamhilad Park, Pontypool, NP4 0HZ UK) for stabilization of proteins. Once deposited in the device, the deposited reagent may, for example, be dried for 30 to 60 minutes in a stream of warm air. In one embodiment, the reagent is printed in the sample inlet of the device using an automated printing instrument and dried to form a leukocidal reagent-containing coating layer.

IV. Sacrificial Beads

As indicated above, in addition to the use of one or more leukocidal reagents, the sample, e.g., blood sample, may be further amended with sacrificial or decoy beads that are homogeneously mixed with the sample, and where the beads are specifically opsonized with respect to leukocytes.

In one embodiment of the invention, the sacrificial beads are coated with a non-human IgG (IgG class immunoglobulins) or fragments thereof isolated from animal species. As used herein, the term "fragment" refers to any epitope-bearing fragment derived from the specified molecule. Thus, an IgG fragment may comprise, for example, epitope bearing F(ab')2 or Fab fragments or an Fc fragment. In addition, the phrase "IgG or fragments thereof" is meant to include IgG alone, IgG fragments alone (i.e., one or more of F(ab')2 fragments, Fab fragments and/or Fc fragments of IgG), or a combination of IgG and IgG fragments. The desired effect may be achieved with a variety of surface coatings, so long as the surface coating is opsonized or opsonizable upon exposure to a sample to be assayed.

As indicated above, in a preferred embodiment, the sacrificial beads are incorporated into a dry reagent coating, which in some embodiments may be the same dry reagent coating that contains the signal-generating reagent (e.g., signal antibody for non-competitive assays or labeled analyte for competitive assays) or the leukocidal reagent. Thus, in one embodiment of the invention, the analysis device includes a dry reagent coating that comprises either or both: (a) a leukocidal reagent; (b) a component suitable for ameliorating the effect of leukocytes, e.g., beads coated with IgG or fragments thereof, and/or (c) a signal-generating reagent such as a signal antibody or a labeled analyte.

V. Additives

In some embodiments of the invention, additives may be included in the cartridge or used in conjunction with the assay. In certain embodiments, an anticoagulant can be added. For example, in some embodiments, heparin is added to improve performance in cases where the sample was not collected in a heparinized tube or was not properly mixed in a heparinized tube. A sufficient amount of heparin is added so that fresh unheparinized blood will remain uncoagulated during the assay cycle of the cartridge, typically in the range of 2 to 20 minutes. In other embodiments, goat and mouse IgG can be added to combat heterophile antibody problems known in the immunoassay art. In still other embodiments, one or more of proclin, DEAE-dextran, tris buffer, and lactitol can be added as reagent stabilizers. In other embodiments, a surfactant such as for example polysorbate 20 (Tween-20) can be added to reduce binding of proteins to the plastic, which is the preferred material for the cartridge. The addition of a surfactant also facilitates the even coating of reagents on the plastic surface and acts as an impurity that minimizes the crystallization of sugars, such as lactitol. In other embodiments of the invention, a antibacterial agent or biocide (e.g., sodium azide) may be added to inhibit bacterial growth.

VI. Preparation of Print Cocktail and Printing

In a preferred embodiment, the base print cocktail is prepared as follows for a 1 liter (L) batch: protein stabilization solution (PSS, AET Ltd., 50% solids, 100.0 g) is added to 200-250 mL of an aqueous solution of sodium chloride (8.00 g) and sodium azide (0.500 g) and the resulting solution is transferred to a 1 L volumetric flask. A solution of murine IgG is prepared by adding murine IgG (0.9 g) to 75 mL of deionized water and stirred for 15-60 minutes until dissolution is complete. An equally concentrated solution of caprine IgG is prepared in an identical manner and both solutions are filtered through a 1.2 µM filter. Murine IgM is acquired as a liquid from a supplier (for example, Sigma-Aldrich). The protein concentrations of each of the three immunoglobulin (Ig) stock solutions are measured spectrophotometrically at 280 nm. The masses of these Ig solutions required to provide murine IgG (0.75 g), caprine IgG (0.75 g), and murine IgM (25 mg) are calculated and these amounts are added to the printing solution. A solution of diethylaminoethyl-dextran (DEAE-dextran) is prepared by adding DEAE-dextran (2.5 g) to 50-100 mL of deionized water and stirring for 30 minutes. The DEAE-dextran solution is added to the printing solution. To this is added sodium heparin (10,000 IU/mL, 3.00 mL), Tween-20 (3.00 g) and a 5% (w/v) aqueous solution of rhodamine (200 µl). The resulting solution is diluted to 1.000 L with deionized water and stored in a freezer or refrigerator until use. When included, IgG-coated microparticles for leukocyte interference mitigation can be added before this final dilution. Likewise leukocidal reagents of the type described above may be added before the final dilution or just prior to deposition into a test device, e.g., a cartridge of the general type shown in FIGS. 1-6.

In various embodiments of the invention, printing of print cocktails and similar fluids to forth a dry reagent coating on the cartridge component is preferably automated and based on a microdispensing system, including a camera and computer system to align components, as disclosed in U.S. Pat. No. 5,554,339 to Cozzette et al. (the "'339 patent"), which is incorporated herein by reference in its entirety. In the '339 patent, the wafer chuck is replaced by a track for feeding the plastic cartridge bases to the dispensing head. The track presents the bases to the head in a predetermined orientation to ensure consistent positional dispensing.

VII. Collection and Analysis

According to various embodiments of the invention, the leukocidal reagent, and (if employed) sacrificial beads may be incorporated in a sample collection device, e.g., capillary, Vacutainer™ or syringe. In some embodiments, the leukocidal reagent coating is formed on an interior wall of the collection device. As such, in one embodiment, the invention is to a kit for performing an immunoassay that comprises the leukocidal reagent, which is first used to amend the blood sample in a first container or location, and then the sample is passed to a second container or location which has the capture and signal antibodies.

In another embodiment, the leukocidal reagent may be contained in solution and mixed with the biological sample, e.g., blood, and the resulting amended sample is introduced into the analysis device, e.g., cartridge. In one embodiment, for example, a blood sample may be mixed with the leukocidal reagent (and optionally sacrificial beads) to form an amended sample, which is then introduced into the analysis device, e.g., cartridge. In another aspect, the device includes a pouch therein that contains a liquid comprising the leukocidal reagent and optionally sacrificial beads, which may be mixed with a blood sample in the device and then processed substantially as described herein to form an assay, e.g., sandwich assay, for analyte detection.

In still another embodiment, electrowetting is employed to mix a first liquid comprising the leukocidal reagent with a liquid biological sample such as for example blood. In this embodiment, an apparatus may be provided for manipulating droplets. The apparatus, for example, may have a single-sided electrode design in which all conductive elements are contained on one surface on which droplets are manipulated. In other embodiments, an additional surface can be provided parallel with the first surface for the purpose of containing the droplets to be manipulated. The droplets are manipulated by performing electrowetting-based techniques in which electrodes contained on or embedded in the first surface are sequentially energized and de-energized in a controlled manner. The apparatus may allow for a number of droplet manipulation processes, including merging and mixing two droplets together, splitting a droplet into two or more droplets, sampling a continuous liquid flow by forming from the flow individually controllable droplets, and iterative binary or digital mixing of droplets to obtain a desired mixing ratio. In this manner, droplets of the first liquid comprising the leukocidal reagent and other reagents (e.g., sacrificial beads) may be carefully and controllably merged and mixed with the liquid biological sample, e.g., blood. (See, e.g., U.S. Pat. No. 6,911,132 to Pamula et al., the entirety of which is incorporated herein by reference).

VIII. Immunosensor Embodiments and Methods Related Thereto

While the present invention is broadly applicable to immunoassay systems, it is best understood in the context of the i-STAT® immunoassay system (Abbott Point of Care Inc., Princeton, N.J., USA), as described in the jointly-owned pending and issued patents cited above. See also U.S. Patent Application No. 61/288,189, entitled "Foldable Cartridge Housings for Sample Analysis," filed Dec. 18, 2009, the entirety of which is incorporated herein by reference. In various embodiments, the system employs an immuno-reference sensor (See, e.g., U.S. Pat. Appl. Pub. 2006/0160164 to Miller et al., referenced above and incorporated herein by reference in its entirety) for purposes of assessing the degree of non-specific binding (NSB) occurring during an assay. NSB may arise due to inadequate washing or due to the presence of interferences. The net signal from the assay is comprised of the specific signal arising from the analyte immunosensor corrected by subtracting the non-specific signal arising from the immuno-reference sensor. The amount of signal at the immuno-reference sensor is subject to limits defined by a quality control algorithm.

Embodiments of the present invention improve the resistance of the i-STAT® immunoassay format to interference caused by leukocytes; however, such embodiments are equally applicable to the standard ELISA format, where cells are present in the analysis medium. In some embodiments, the sample is amended with sacrificial beads preferably in combination with a leukocidal reagent of the present invention to provide reduced or eliminated leukocyte interference.

It should be noted that while traditional sandwich assays may yield erroneous results for biological samples having a high leukocyte level, prior i-STAT® system assays did not previously report inaccurate results for these samples, as the system includes an algorithm that detects spurious signals, alerts the user with an error code, and suppresses the result from being displayed. This is one embodiment of a quality system for reliable point-of-care testing. In this way the quality and integrity of the analytical system is maintained.

Surprisingly and unexpectedly, when modified cartridges containing leukocidal reagents were tested and the results compared with conventional cartridges lacking these materials, the results demonstrated that blood samples exhibiting leukocyte interference in the conventional cartridges could be analyzed accurately when the leukocidal reagents were employed.

Figure 11:
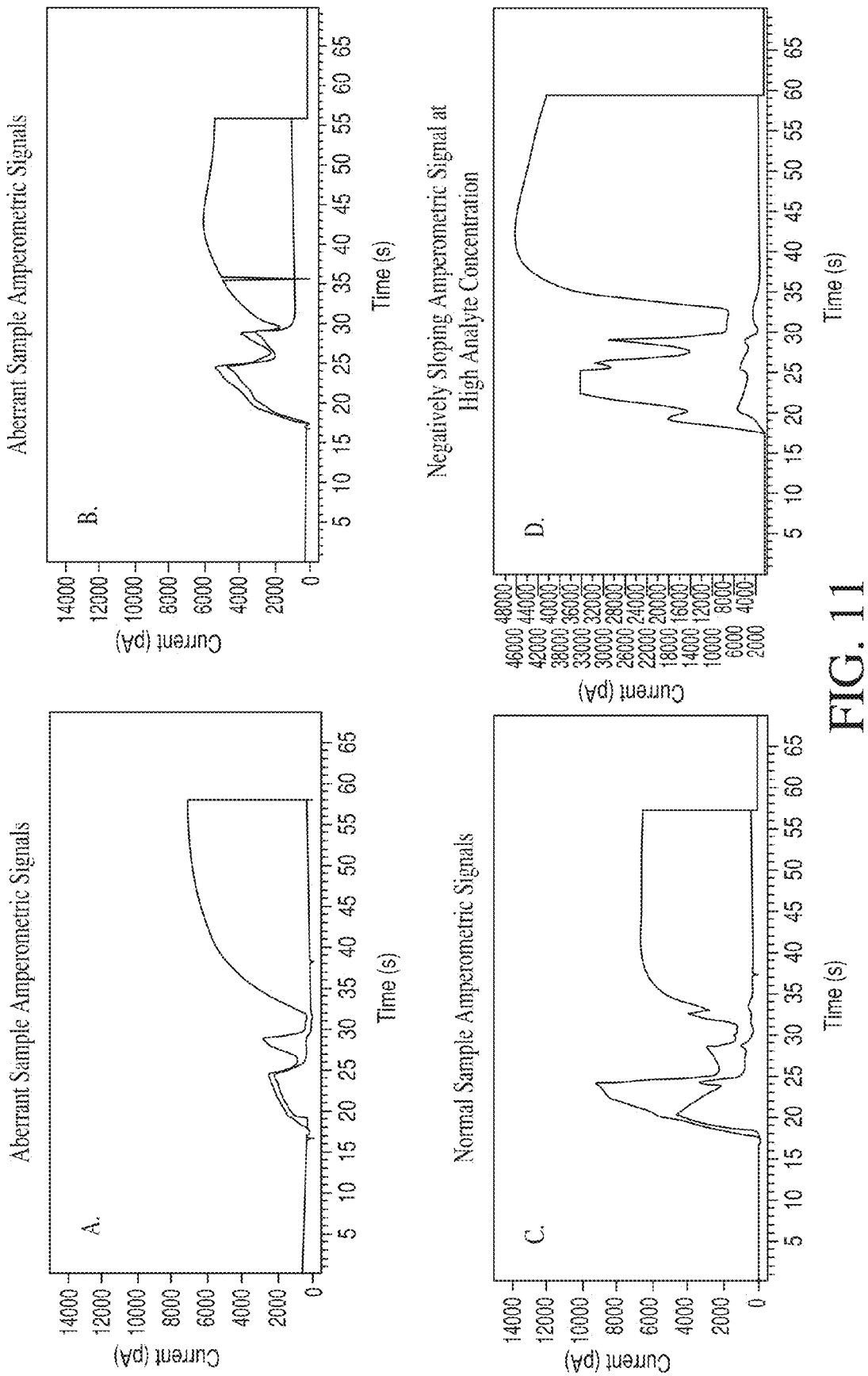
FIG. 11(a) shows an unexpected waveform for a brain natriuretic peptide (BNP) cartridge with a positively sloping output signal.
FIG. 11(b) shows an unexpected waveform for a BNP cartridge with a negatively sloping output signal.
FIG. 11(c) shows a normal response, which has a near-zero slope for low analyte concentrations.
FIG. 11(d) illustrates that negative slopes are expected only at high analyte concentrations where the measurement can become substrate-limited rather than enzyme limited.

With regard to the subject matter of the present invention, it was discovered that certain immunoassay test cartridges, notably BNP cartridges, exhibited unexpected positively and negatively sloping waveforms arising from a previously unknown interference mechanism. See, for example, FIGS. 11(a) and (b), respectively. This led to a hypothesis concerning the mechanism of the interference based on experiments on the effect of pulsing the electrode to positive potentials during the wash step. As shown in FIGS. 11(c) and (d), the normal immunosensor response, expected on a theoretical basis, has a near-zero slope at low analyte concentrations, and negative slopes are expected only at high analyte concentrations where the measurement can become substrate-limited rather than enzyme limited.

There are several potential mechanisms causing dynamic (non-steady state) amperometric signals. Dynamic electrode activity (changing effective electrode area) is unlikely since the electrode is sequestered from formed elements owing to the presence of immobilized assay beads (microparticles) on a polyvinyl alcohol (PVA) layer, neither of which exhibit this effect in plasma samples. Dynamic layer thickness, e.g., swelling or shrinking of the components above, depending on fluid contact, is unlikely as there is no driving force for such a phenomenon that would elicit both positive and negative slopes. Dynamic coverage of the enzyme (e.g., ALP, changing surface concentration of enzyme) is ruled out because in the thin-layer format, diffusion of enzyme (e.g., ALP) from the sensor over the time-scale of the measurement is not possible. Dynamic transport of the enzyme substrate, e.g., para-aminophenol phosphate (p-APP), to the electrode surface is unlikely given the size of the molecule, which is relatively small and has a relatively facile diffusion (D≈5× $10^{-6}$ cm$^2$/s). Thus, by the process of elimination, dynamic ALP activity was considered the most likely cause of dynamic sensor signals and further investigation was made to assess the mechanism. It is noted that the hydrolysis of p-aminophenyl phosphate by ALP is pH-dependent with an optimum near pH 10. In some embodiments, in the cartridge, a working pH of 9.2 is used as this slightly lower pH value ensures stability of immunocomplexes. In addition, the oxidation of para-aminophenol (p-AP) at the electrode is pH dependent and is expected to shift by about +59 mV per decade decrease in pH, i.e., at lower pH the reaction must be driven harder, i.e., an increased applied potential is required.

In embodiments where the microparticle print layer was to become less permeable due to interaction with the interfering components to the extent that sample fluid (pH 7.4) within the sensor structure could not be fully replaced with analysis fluid (pH 9.2) during the wash step, this results in suboptimal detection step pH, particularly for the electrode reaction which occurs at a region farthest from the point of entry of the analysis fluid. This impaired fluid replacement creates a pH gradient that undergoes relaxation with time. As the relative rates of the enzyme and electrode reactions change, so will the observed signal. This technical evaluation has the considerable advantage that it offers an explanation for both positive and negatively sloping signals. See, e.g., FIGS. 11(a) and (b).

Figure 12:
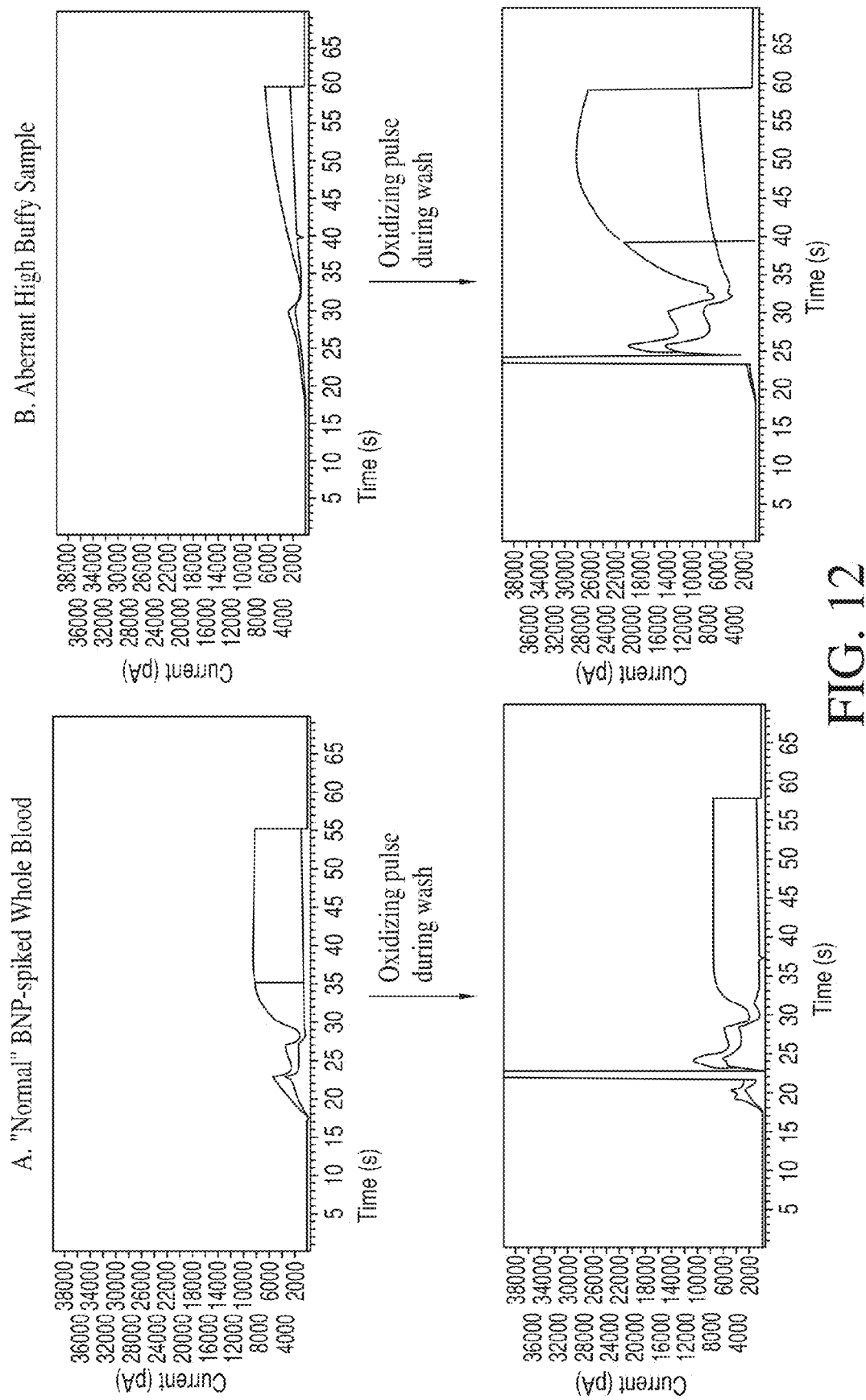
FIG. 12 shows the effect of oxidative electrode pulsing during the wash step on (a) a normal sample, and (b) an aberrant buffy sample.
Figure 13:
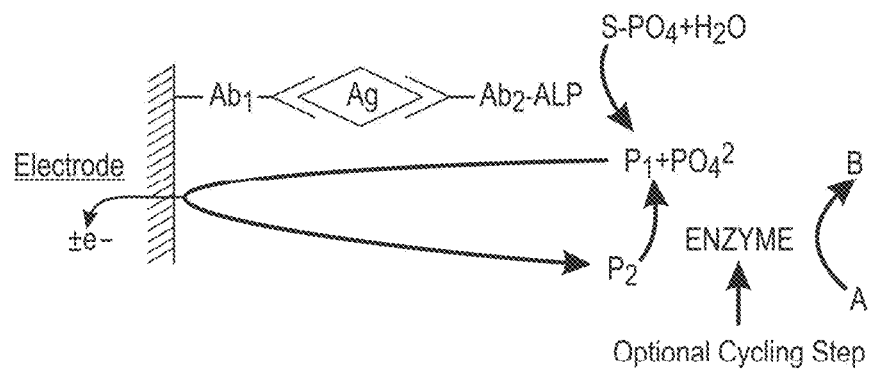
FIG. 13 is a schematic illustration of enzymatic regeneration of an electroactive species.

The conception that the observed interference is associated with an incomplete wash step due to "plugging" or "fouling" of the microparticle layer was assessed further by applying a pulse to extreme potentials, e.g., applying a pulse to an oxidizing potential, during the wash step. It was anticipated that positively sloping waveforms might be caused by an inactive blocked sensor and that pulsing might be employed to clean the electrode prior to the analysis step. It was observed that applying an oxidizing pulse during the wash step in a normal sample had no effect on observed signal and in the subsequent analysis. See FIG. 12(a). However, in the case of aberrant high buffy samples the effect of pulsing was large and dynamic signals and further, these signals were greater than expected given the concentration of analyte. See FIG. 12(b).

The difference in the response to an oxidizing potential pulse in these two cases demonstrated that the fluids within the sensor structure were indeed different. As anticipated, the correct response resulted from the presence of desired analysis fluid over the sensor, whereas the abnormal response arose because the fluid over the sensor structure was plasma, or a combination of plasma and analysis fluid. The difference in response can be understood as follows: the oxidizing pulse results in the evolution of oxygen and a decrease in pH according to: $H_2O \rightarrow \frac{1}{2} O_2 + 2H^+ + 2 e^-$.

In the case of the sensor structure containing analysis fluid buffered to pH 9.2, protons evolved at the electrode were rapidly consumed in the presence of the buffer (100 mM carbonate in analysis fluid). However, in the absence of the buffering afforded by the analysis fluid, protons persisted in the region of the electrode resulting in a plume of acidic fluid. This acidic plume resulted in the acid-catalyzed hydrolysis of pAPP to pAP generating a larger signal than anticipated. Specifically, the aberrant waveform arose from pAP generated by the enzymatic action of the enzyme, e.g., ALP, on pAPP and also non-enzymatic acid-catalyzed hydrolysis.

It is noted that the acid-catalyzed hydrolysis reaction does not occur significantly for p-aminophenyl phosphate unless the amino group is protonated as it is at low pH. This is because the reaction requires a strongly electron-withdrawing substituent in the para position (Barnard et al., J. Chem. Soc. (1966), 227-235). As is known in the art, an —$NH_2$ substituent is significantly electron-donating, whereas upon protonation the —$NH_3^+$ substituent becomes highly electron-withdrawing (more so even than —$NO_2$; for example the Hammet para-rho values are −0.66 for —$NH_2$ and 1.70 for —$NH_3^+$).

These experiments associated the observed interference with "high buffy" samples and could intentionally be elicited by running whole blood samples with an enriched buffy coat. This term is given to the layer of white blood cells and platelets that form at the plasma-red cell boundary when a blood sample is centrifuged. Further evidence implicating leukocytes and potentially platelets as fouling agents is shown in the micrographs FIG. 17(*a*) (assay without use of sacrificial beads or leukocidal reagent) and 17(*b*) (assay after using sacrificial beads). For comparison, a pristine immunosensor prior to contact with a blood sample is illustrated in FIG. 20. Similar results were obtained providing visual confirmation for the use of leukocidal reagents in reducing leukocyte adhesion to sensors.

FIG. 17(*a*) shows a sensor that was exposed to a high buffy sample (~$10^5$ leukocytes per μL) using the standard measurement cycle with a sensor incubation time of 10 minutes. The sample was not exposed to opsonized sacrificial beads or any leukocidal reagents. It is clear that a portion of the assay bead-coated sensor surface is covered with an adhered layer of cells that were not easily removed by the wash step.

By contrast, FIG. 17(*b*) shows a sensor that was exposed to a high buffy sample (~$10^5$ leukocytes per μL) using the standard measurement cycle with a sensor incubation time of 10 minutes. However, in contrast to the assay shown in FIG. 17(*a*), the sample shown in FIG. 17(*b*) was exposed to opsonized (IgG coated) sacrificial beads. It is clear that the portion of the assay bead-coated sensor surface had significantly less adhered cells when compared to FIG. 17(*a*) after the wash step.

IgG acts as an opsonin, which is a substance capable of marking a pathogen for phagocytosis, for example, by leukocytes. IgGs are generally added to immunoassays to manage heterophile antibody interference as described in jointly-owned pending U.S. application Ser. No. 12/411,325, and are present on assay beads in the BNP cartridge described herein. Consequently, it is likely that either this source of IgG (when present in an immunoassay device) or IgG naturally present in the blood sample may act to undesirably opsonize the sensor surface to leukocytes. In addition, as the assay beads are similar in size to biological cells (bacteria), which are the natural target of phagocytosis, it is probable that IgG accumulation on the assay beads is undesirably promoting accumulation of leukocytes on these beads. This is consistent with the observed interference in samples with high white cell counts, and possibly those with an activated immune status. The present invention provides a solution to this leukocyte interference whereby the amendment of a sample with a leukocidal reagent, optionally with sacrificial IgG-coated microparticles, affords a means for decreasing leukocyte activity so as to divert them from the primary immune reagents on the sensor.

As indicated above, in some embodiments, the sample is amended with sacrificial beads in addition to the leukocidal reagent. Preparation of IgG-coated microparticles may be effected using methods analogous to those employed for preparation of the assay beads. This method involves adsorption of IgG onto carboxylated polystyrene microparticles in MES buffer (2-(N-morpholino)ethanesulfonic acid) followed by cross-linking in the presence of EDAC (1-ethyl-3-(3-dimethylaminopropyl)carbodiimide).

One non-limiting method for forming the sacrificial beads is now described. In a preferred procedure, raw microparticles are pelleted by centrifugation at 18,000 RCF (relative centrifugal force) for 20 minutes from their matrix (10% microparticles in water, Seradyn) and re-suspended in 25 mM MES buffer to a concentration of 100-200 mg/mL microparticles. IgG dissolved in 25 mM MES buffer is then added in a quantity equal to about 1 to 5% of the weight of the microparticles. After a 15-20 minutes nutation in a refrigerator, the microparticles are pelleted by centrifugation for 20 minutes at 1300 RCF is re-suspended in fresh MES buffer to a concentration of 75 mg/mL. The supernatant from centrifugation is assayed for protein content by measuring absorbance at 280 nm (effective extinction coefficient of 1.4 AU/mg/mL protein) to confirm the IgG has absorbed onto the microparticles. Freshly prepared EDAC cross-linking agent (10 mM in MES buffer) is added to the re-suspended microparticles to a final concentration of about 2-4 mM. The mixture is then stirred by nutation in a refrigerator for 120±15 minutes. The microparticles may then again be pelletized by centrifugation at 1300 RCF for 20 minutes and re-suspended in 1/5 PPS (phosphate buffered saline) and nutated in the refrigerator for 15-30 minutes. Upon final centrifugation, the microparticles can be re-suspended in PBS+0.05% Sodium Azide or in 1:1 1/5 PPB:PSS (1/5 PPB is PBS diluted with 4 parts water, PSS=protein stabilization solution, Applied Enzyme Technologies, Ponypool, UK) to a concentration of 10% solids. The resulting preparation may be aliquoted and stored frozen, preferably at −60° C. Microparticles suspended in PBS formed by this process were employed in the experiments described herein and were dosed directly into blood samples.

Preparation of an enriched or high buffy whole blood sample, as described for use in the experiments described herein, was as follows. Fresh whole blood was drawn from a donor into two 6 mL EDTA-anticoagulated Vacutainers™ and was centrifuged for 10 minutes at 2000 RCF (standard rotor). Where BNP "positive" samples were desired, the tubes were spiked with the BNP antigen prior to centrifugation. All of the plasma except the last millimeter above the plasma/buffy coat/red blood cell interface was withdrawn and set aside. The interfacial region was then withdrawn using a pipettor (with the intention of removing as much of the buffy coat layer as possible) and was set aside. The red blood cells were then removed and set aside. By recombining the buffy coat materials with lesser portions of the plasma and red cell fractions, it was possible to create high buffy blood samples while retaining a normal sample hematocrit, e.g., 35-55 wt. %. Similarly, samples with a low or essentially no buffy material (leukocytes and platelets) present can be created.

In experiments, BNP test cartridges were tested with: (i) high buffy samples, (ii) high buffy samples treated with a 10 percent volume a suspension of 10 weight percent microparticles coated with IgG (μP-IgG) in PBS immediately before running, (iii) high hematocrit leukocyte-free samples, and (iv) low hematocrit leukocyte-free samples.

Figure 21:
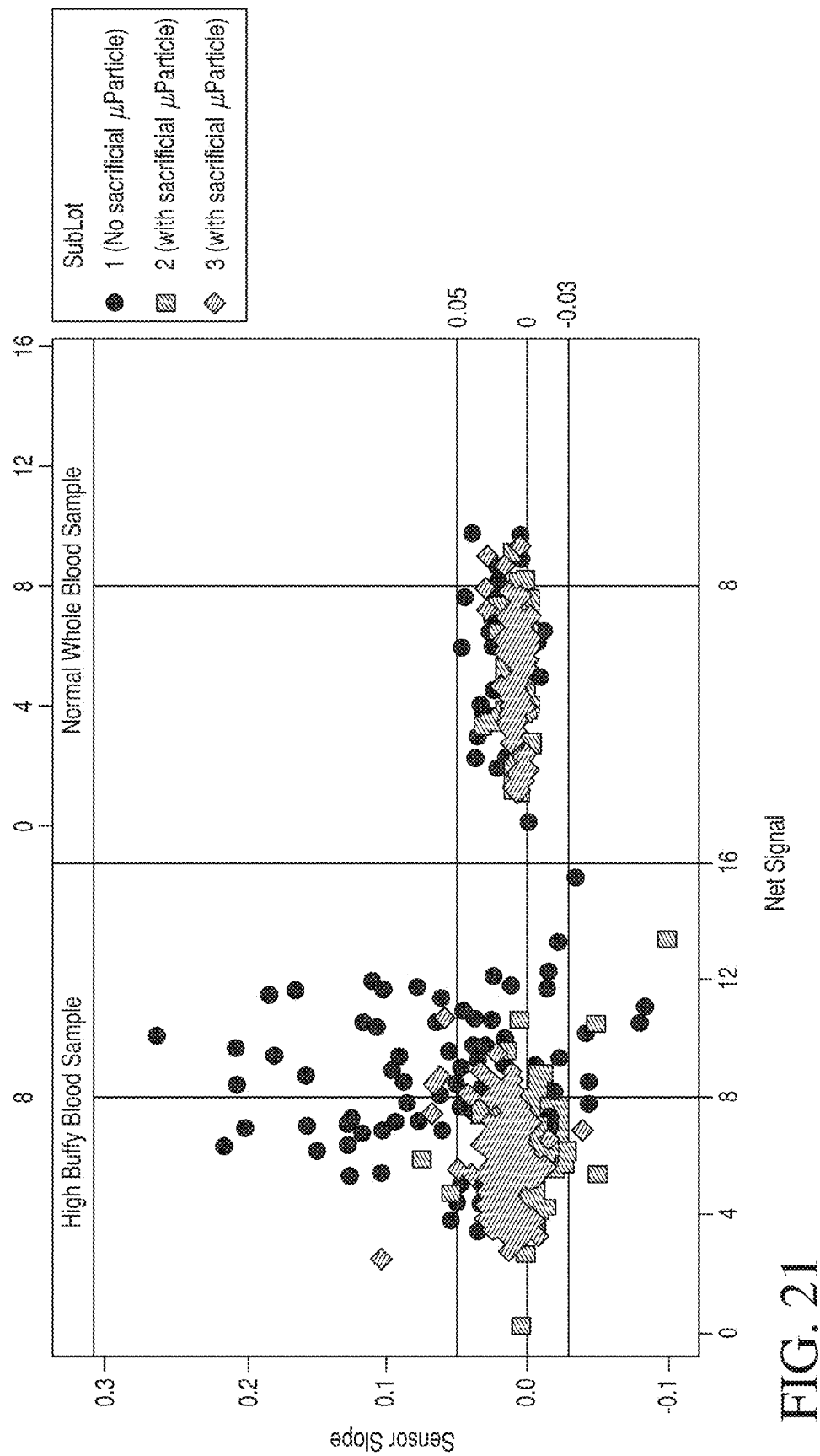
FIG. 21 shows graphical data for the effect on immunosensor slope in high buffy (left panel) and normal whole blood (right panel) samples with (sublots 2 and 3) and without (sublot 1) sacrificial microparticles incorporated in the reagent.

FIG. 21 contains graphical data illustrating the effect of leukocyte interference on electrochemical immunosensor signal slopes and the effect of sacrificial microparticle treatment on the slopes. Illustrated in the right and left panels are Sensor Slopes (y-axis) plotted as a function of Net Signal (x-axis) for normal whole blood sample (right panel) and high buffy blood sample (enriched leukocyte, high buffy, left panel). The left panel illustrates the considerable variability of signal slopes observed in high buffy samples in the absence of sacrificial microparticles (Sublot 1). This variability was substantially ameliorated in the presence of sacrificial microparticles (Sublots 2 and 3). Minimal signal slope variability was observed in the normal whole blood samples (right panel) both with and without sacrificial microparticles.

Figure 17A:
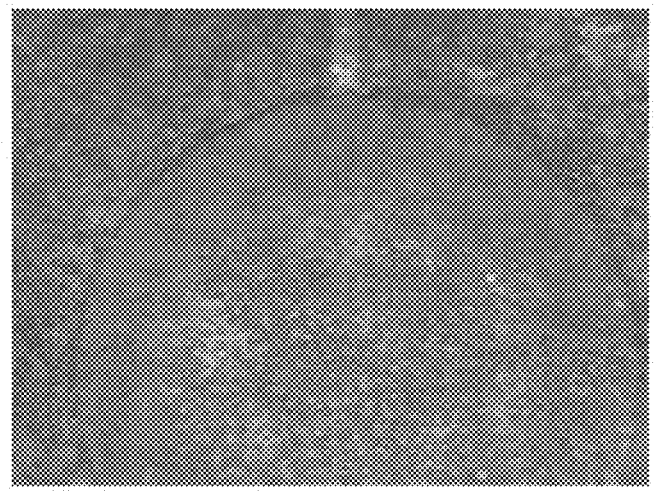
FIGS. 17(a) and (b) show micrographs of immunosensors after assay of BNP in a high buffy sample in the (a) absence and (b) presence of sacrificial beads in the sample.
Figure 17B:
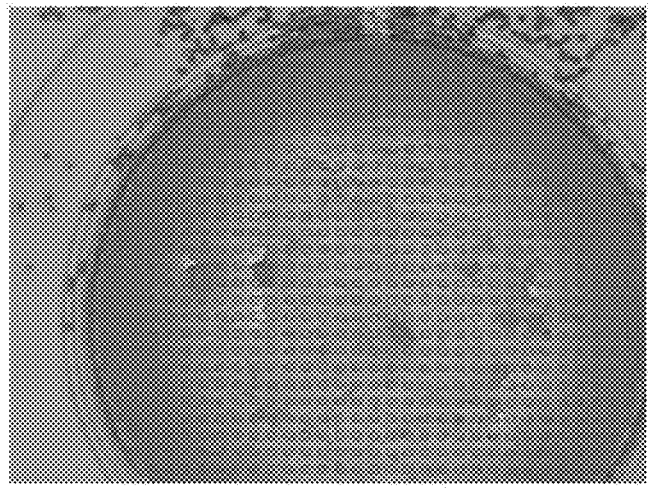
Figure 22:
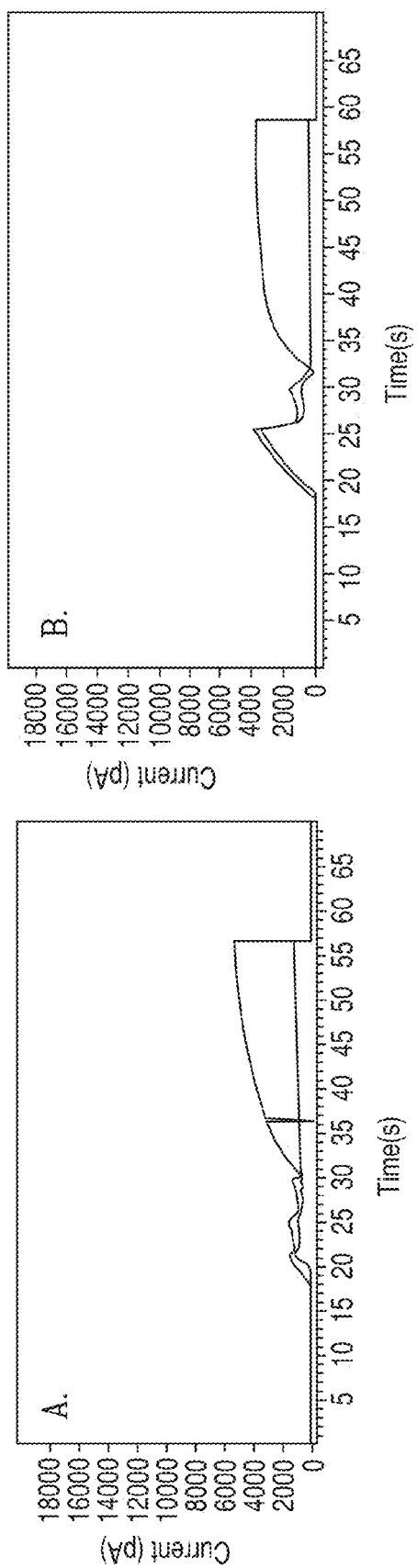
FIGS. 22(a) and (b) show analyzer waveforms for the associated immunosensor micrographs in FIGS. 17(a) and (b)
Figure 23:
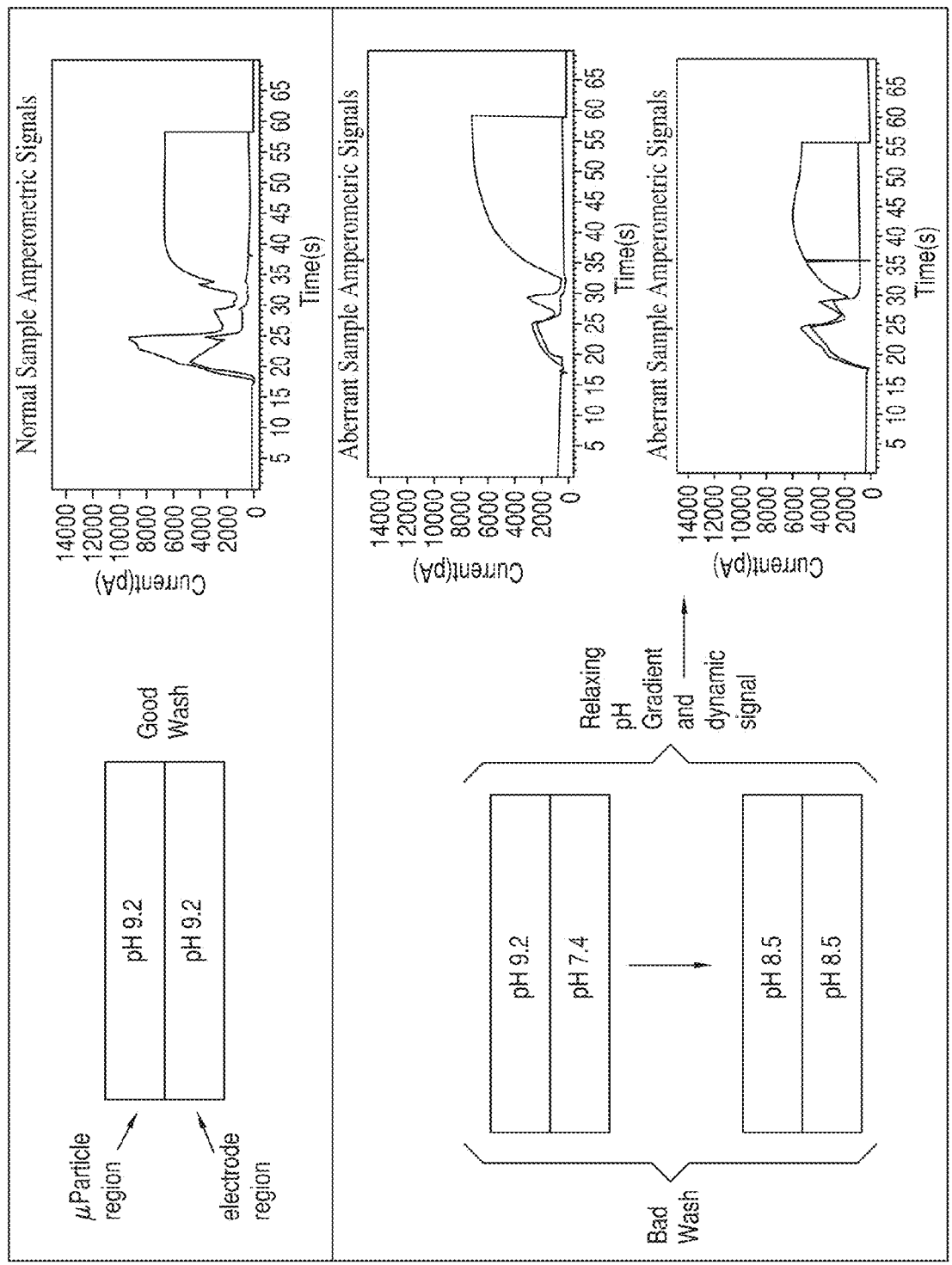
FIG. 23 illustrates the effect of poor washing (inability to replace sample fluid within sensor structure with analysis fluid) on amperometric waveforms.

Microscopic inspection of sensors following the assay revealed the presence of a thick deposit on chips run in high buffy (HB) and the absence of a deposit on samples run in HB/μP-IgG. Micrographs of the immunosensors are shown in FIGS. 17(a) and 17(b) and their associated analyzer waveforms are illustrated in FIGS. 22(a) and (b), respectively. It is clear from a comparison of a pristine immunosensor prior to contact with a blood sample as illustrated in FIG. 20 with the immunosensor after contact with blood treated with the sacrificial beads (FIG. 17(b)) that visually there is a significant improvement, i.e., a reduction in adhered leukocytes compared to FIG. 17(a). Based on many observations, this visual improvement correlates directly with an actual improvement in immunosensor performance.

Additional experiments showed that the interference phenomenon does not occur in plasma alone or in samples containing platelets but not leukocytes, but only in samples containing a high buffy level. In addition, smaller microparticles, e.g., those having an average particle size less than 0.2 μM, coated with IgG do not have the same interference mitigating effect on sensor slopes as do larger particles. Preferably, the average particle size of the IgG-coated microparticles (sacrificial beads), if included with the leukocidal reagent(s), is from 0.01 to 20 μm, e.g., from 0.1 to 20 μM, from 1 to 10 μm, from 0.1 to 5 μM, or from 2 to 5 μm. The particle size distribution of the sacrificial microparticles preferably is unimodal, although polymodal distributions are also possible. In principle, any particles of the correct size and capable of being opsonized may be used; however, polystyrene beads are preferred. In preferred embodiments of the invention, goat or sheep IgG coated particles are employed, although other IgG sources may be employed such as, for example, mouse or rabbit IgG. In general, it was found that the size of the microparticles is important, but not its composition or the source of the IgG. With regard to the sacrificial beads, the beads, if employed, preferably comprise substrate beads formed of a material selected from the group consisting of polystyrene, polyacrylic acid and dextran, and can have an average particle size in the range of about 0.01 μm to about 20 μm, more preferably an average particle size in the range of from 0.1 μm to 5 μm or from about 2 μm to about 5 μm. While use of a spherical bead is preferred, in other embodiments, other bead shapes and structures, e.g., ovals, sub-spherical, cylindrical and other irregular shaped particles, are within the meaning of the terms "beads" and "microparticles" as used and defined herein. As used herein, the term "average particle size" refers to the average longest dimension of the particles, for example the diameter for spherical particles, as determined by methods well-known in the art.

Collectively, the experimental data support the conclusion that leukocytes are primarily responsible for a phenomenon in which the sensor becomes less permeable in the wash cycle and that this immunoassay interference can be ameliorated by addition of sacrificial IgG coated particles to the assay medium.

Figure 9:
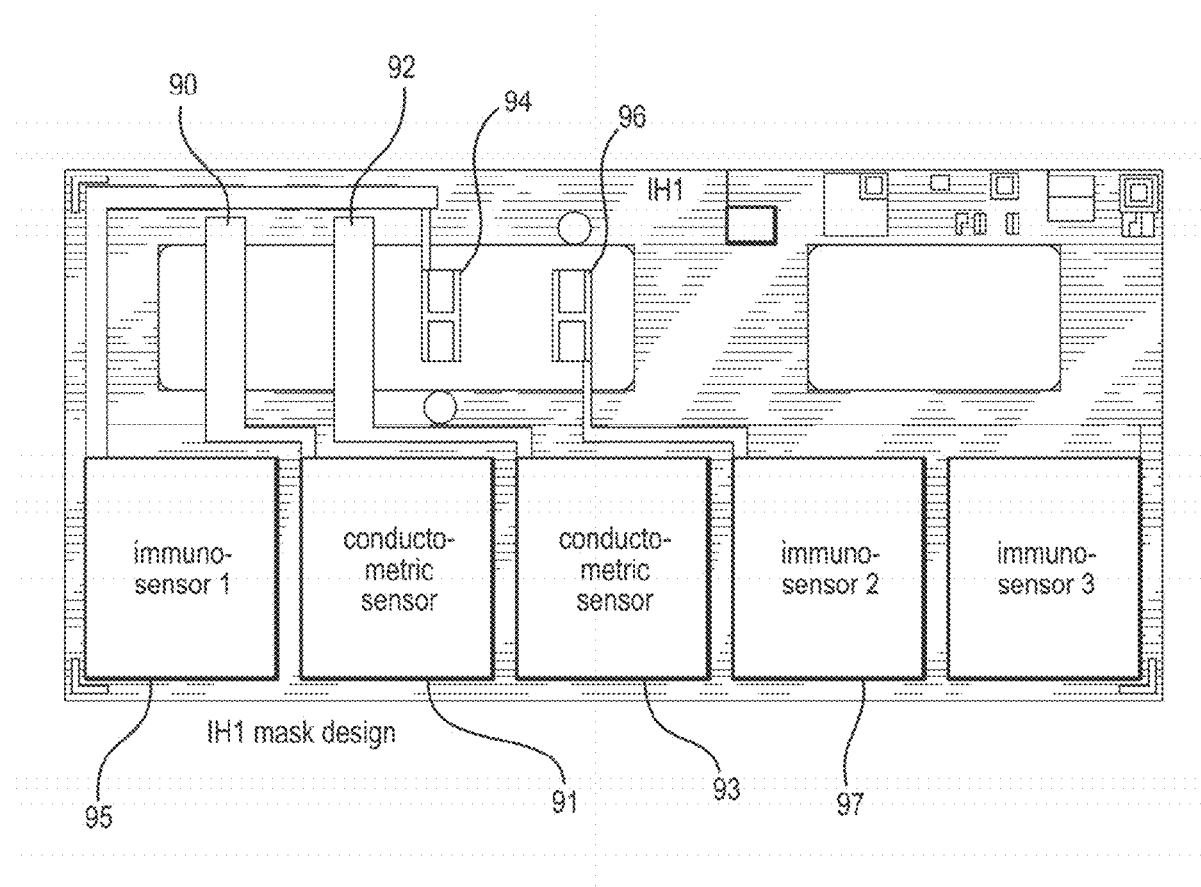
FIG. 9 is a top view of the mask design for the conductimetric and immunosensor electrodes for an immunosensor cartridge.

Wafer-level microfabrication of a preferred embodiment of the immunosensor of the present invention is as follows. As shown in FIG. 9, the base electrode 94 comprises a square array of 7 μm gold disks on 15 μm centers. The array covers a circular region approximately 600 μm in diameter, and is achieved by photo-patterning a thin layer of polyimide of thickness 0.35 μm over a substrate made from a series of layers comprising Si/SiO$_2$/TiW/Au. The array of 7 μm microelectrodes affords high collection efficiency of electroactive species with a reduced contribution from any electrochemical background current associated with the capacitance of the exposed metal. The inclusion of a poly(vinyl alcohol) (PVA) layer over the metal significantly enhances the reduction of background currents.

In some embodiments, the porous PVA layer is prepared by spin-coating an aqueous mixture of PVA plus a stilbizonium photoactive, cross-linking agent over the microelectrodes on the wafer. The spin-coating mixture optionally includes bovine serum albumin (BSA). The wafer is then photo-patterned to cover only the region above and around the arrays and preferably has a thickness of about 0.6 μm.

The general concept of differential measurement is known in the electrochemical and sensing arts. A novel means for reducing interfering signals in an electrochemical immunosensing systems is now described. However, while it is described for pairs of amperometric electrochemical sensors it is of equal utility in other electrochemical sensing systems including, but not limited to potentiometric sensors, field effect transistor sensors and conductimetric sensors. Embodiments of the present invention are also applicable to optical sensors, e.g., evanescent wave sensors and optical wave guides, and also other types of sensing including acoustic wave and thermometric sensing and the like. Thus, according to various embodiments of the invention, the immobilized antibody may be attached to a sensor selected from the group consisting of an amperometric electrode, a potentiometric electrode, a conductimetric electrode, an optical wave guide, a surface plasmon resonance sensor, an acoustic wave sensor and a piezoelectric sensor. Ideally, in the non-competitive assay embodiments, the signal from an immunosensor (IS) is derived solely from the formation of a sandwich comprising an immobilized antibody (Ab1), the analyte, and a signal antibody (Ab2) that is labeled, wherein the label (e.g., an enzyme) reacts with a substrate (S) to form a detectable product (P) as shown below in scheme (1).

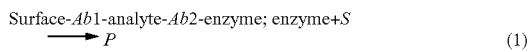

Surface-*Ab*1-analyte-*Ab*2-enzyme; enzyme+*S* ⟶ *P*     (1)

It is known that some of the signal antibody (Ab2) may bind non-specifically to the surface, as shown below in schemes (2) and (3), and might not be washed away completely from the region of the immunosensor (up to approx. 100 microns away) during the washing step thereby giving rise to a portion of the total detected product that is not a function of the surface-Ab1-analyte-Ab2-enzyme immunoassay sandwich structure, thereby creating an interfering signal.

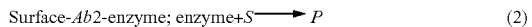

Surface-*Ab*2-enzyme; enzyme+*S* ⟶ *P*     (2)

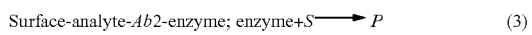

Surface-analyte-*Ab*2-enzyme; enzyme+*S* ⟶ *P*     (3)

As indicated above, a second immunosensor optionally may be placed in the cartridge that acts as an immuno-reference sensor (IRS) and gives the same (or a predictably related) degree of NSB as occurs on the primary immunosensor. In one embodiment, interference can be reduced by subtracting the signal of this immuno-reference sensor from that of the primary immunosensor, i.e., the NSB component of the signal is removed, improving the performance of the assay, as shown in scheme (4) below. In another embodiment, the correction may optionally include the subtraction or addition of an additional offset value.

Corrected signal–*IS*–*IRS*     (4)

In preferred embodiments of the invention, the reference immunosensor, also referred to as immuno-reference sensor, is the same in all significant respects (e.g., dimensions, porous screening layer, latex particle coating, and metal electrode composition) as the primary immunosensor except that the capture antibody for the analyte (e.g., cTnI) is replaced by an antibody to a plasma protein that naturally occurs in samples (both normal and pathological) at a high concentration. The immunosensor and reference immunosensor may be fabricated as adjacent structures 94 and 96, respectively, on a silicon chip as shown in FIG. 9. While the preferred embodiment is described for troponin I and BNP assays, this structure is also useful for other cardiac marker assays including, for example, troponin T, creatine kinase MB, procalcitonin, proBNP, NTproBNP, myoglobin and the like, plus other sandwich assays used in clinical diagnostics, e.g., PSA, D-dimer, CRP, HCG, NGAL, myeloperoxidase and TSH.

Examples of suitable antibodies that bind to plasma proteins include antibodies to human serum albumin, fibrinogen and IgG fc region, with albumin being preferred. However, any native protein or blood component that occurs at a concentration of greater than about 100 ng/mL can be used if an appropriate antibody is available. The protein should, however, be present in sufficient amounts to coat the sensor quickly compared to the time needed to perform the analyte assay. In a preferred embodiment, the protein is present in a blood sample at a concentration sufficient to bind more than 50% of the available antibody on the reference immunosensor within about 100 seconds of contacting a blood sample. In general the second immobilized antibody has an affinity constant of about $1 \times 10^{-7}$ to about $1 \times 10^{-15}$ M. For example, an antibody to albumin having an affinity constant of about $1 \times 10^{-10}$ M is preferred, due to the high molar concentration of albumin in blood samples, which is about $1 \times 10^{-4}$ M.

According to various embodiments of the present invention, providing a surface that is covered by native albumin derived from the sample significantly reduces the binding of other proteins and cellular materials that may be present. This method is generally superior to conventional immunoassays that use conventional blocking agents to minimize NSB because these agents must typically be dried down and remain stable for months or years before use, during which time they may degrade, creating a stickier surface than desired and resulting in NSB that rises with age. In contrast, the embodiments of the present invention provide for a fresh surface at the time of use.

An immunosensor for cardiac brain natriuretic peptide (BNP) with a reference immunosensor for performing differential measurement to reduce the effect of NSB is described as follows. In one embodiment, carboxylate-modified latex microparticles (supplied by Bangs Laboratories Inc., Fishers, Ind., USA or Seradyn Inc., Indianapolis, Ind., USA) coated with anti-BNP and anti-HSA are both prepared by the same method. The particles are first buffer exchanged by centrifugation, followed by addition of the antibody, which is allowed to passively adsorb onto the particles. The carboxyl groups on the particles are then activated with EDAC in MES buffer at pH 6.2, to form amide bonds to the antibodies. Any bead aggregates are removed by centrifugation and the finished beads are stored frozen.

In another embodiment, the anti-human serum albumin (HSA) antibody, saturation coverage of the latex beads results in about a 7% increase in bead mass. In yet another embodiment, coated beads are prepared using covalent attachment from a mixture comprising 7 mg of anti-HSA and 100 mg of beads. Using this preparation, a droplet of about 0.4 nL, comprising about 1% solids in deionized water, is microdispensed (using the method and apparatus of U.S. Pat. No. 5,554,339, referenced above and incorporated herein by reference in its entirety) onto a photo-patterned porous PVA permselective layer covering sensor 96, and is allowed to dry. The dried particles adhere to the porous layer and substantially prevent their dissolution in the blood sample or the washing fluid.

In one embodiment of the invention, for the BNP antibody, saturation coverage of the latex bead surface results in a mass increase in the beads of about 10%. Thus by adding 10 mg of anti-BNP to 100 mg of beads along with the coupling reagent, saturation coverage was achieved. These beads were then microdispensed onto sensor 94.

In another embodiment, immunosensor 94 is coated with beads having both a plasma protein antibody, e.g., anti-HSA, and the analyte antibody, e.g., anti-BNP. Latex beads made with the about 2 mg or less of anti-HSA per 100 mg of beads saturation-coated with anti-BNP provide superior NSB properties at the immunosensor. It has been found that the slope (signal versus analyte concentration) of the troponin assay is not materially affected because there is sufficient anti-BNP on the bead to capture the available analyte (antigen). By determining the bead saturation concentration for different antibodies, and the slope of an immunosensor having beads with only the antibody to the target analyte, appropriate ratios of antibody combinations can be determined for beads having antibodies to both a given analyte and a plasma protein.

An important aspect of immunosensors having a reference immunosensor is the "humanizing" of the surface created by a layer of plasma protein, preferably the HSA/anti-HSA combination. This surface "humanizing" appears to make the beads less prone to NSB of the antibody-enzyme conjugate and also seems to reduce bead variability. Without being bound by theory, it appears that as the sensors are covered by the sample they are rapidly coated with native albumin due to the anti-HSA surface. This gives superior results compared to conventional blocking materials, which are dried down in manufacturing and re-hydrated typically after a long period in storage. Another advantage to "humanizing" the sensor surface is that it provides an extra mode of resistance to human anti-mouse antibodies (HAMA) and other heterophile antibody interferences. The effects of HAMA on immunoassays are well known.

In another embodiment, the immuno-reference sensor is employed in the devices and methods of the invention to monitor the wash efficiency obtained during the analytical cycle. As stated above, one source of background noise is the small amount of enzyme conjugate still in solution, or non-specifically absorbed on the sensor and not removed by the washing step. This aspect of the invention relates to performing an efficient washing step using a small volume of washing fluid, by introducing air segments as mentioned in Example 2.

In operation of the preferred embodiment, which is an amperometric electrochemical system, the currents associated with oxidation of p-aminophenol at immunosensor 94 and immuno-reference sensor 96 arising from the activity of ALP, are recorded by the analyzer. The potentials at the immunosensor and immuno-reference sensor are poised at the same value with respect to a silver-silver chloride reference electrode. To remove the effect of interference, the analyzer subtracts the signal of the immuno-reference sensor from that of the immunosensor according to equation (4) above. Where there is a characteristic constant offset between the two sensors, this value is also subtracted. It is not necessary for the immuno-reference sensor to have all of the same non-specific properties as the immunosensor, only that the immuno-reference sensor be consistently proportional in both the wash and NSB parts of the assay. In one embodiment, an algorithm embedded in the analyzer can account for any other essentially constant difference between the two sensors.

Use of a differential combination of immunosensor and immuno-reference sensor, rather than an immunosensor alone, provides the following improvement to the assay. In a preferred embodiment, the cartridge design provides dry reagent that yields about 4-5 billion enzyme conjugate molecules dissolved into about a 10 µL blood sample. At the end of the binding and wash steps the number of enzyme molecules at the sensor is about 70,000. In experiments with the preferred embodiment there were, on average, about 200,000 (±about 150,000) enzyme molecules on the immunosensor and the reference immunosensor as non-specifically bound background. Using a differential measurement with the immuno-reference sensor, about 65% of the uncertainty was removed, significantly improving the performance of the assay. While other embodiments may have other degrees of improvement, the basis for the overall improvement in assay performance remains.

An additional use of the optional immuno-reference sensor is to detect anomalous sample conditions, such as for example improperly anti-coagulated samples which deposit material throughout the conduits and cause increased currents to be measured at both the immunosensor and the immuno-reference sensor. This effect is associated with both non-specifically adsorbed enzyme and enzyme remaining in the thin layer of wash fluid over the sensor during the measurement step.

Another use of the optional immuno-reference sensor is to correct signals for washing efficiency. In certain embodiments, the level of signal at an immunosensor depends on the extent of washing. For example, longer washing with more fluid/air segment transitions can give a lower signal level due to a portion of the specifically bound conjugate being washed away. While this may be a relatively small effect, e.g., less than 5%, correction can improve the overall performance of the assay. Correction may be achieved based on the relative signals at the sensors, or in conjunction with a conductivity sensor located in the conduit adjacent to the sensors, acting as a sensor for detecting and counting the number of air segment/fluid transitions. This provides the input for an algorithmic correction means embedded in the analyzer.

In another embodiment of the reference immunosensor with an endogenous protein, e.g., HSA, it is possible to achieve the same goal by having an immuno-reference sensor coated with antibody to an exogenous protein, e.g., bovine serum albumin (BSA). In this case the step of dissolving a portion of the BSA in the sample, provided as an additional reagent, prior to contacting the sensors is needed. This dissolution step can be done with BSA as a dry reagent in the sample holding chamber of the cartridge, or in an external collection device, e.g., a BSA-coated syringe. This approach offers certain advantages, for example the protein may be selected for surface charge, specific surface groups, degree of glycosylation and the like. These properties may not necessarily be present in the available selection of endogenous proteins.

In addition to salts, other reagents can improve whole-blood precision in an immunoassay. These reagents should be presented to the blood sample in a way that promotes rapid dissolution. In some embodiments, support matrices including cellulose, polyvinyl alcohol (PVA), and gelatin (or mixtures thereof) coated onto the wall of the blood-holding chamber (or another conduit) promote rapid dissolution, e.g., greater than 90% complete in less than 15 seconds.

A cartridge of the present invention has the advantage that the sample and a second fluid can contact the sensor array at different times during an assay sequence. The sample and the second fluid also may be independently amended with other reagents or compounds present initially as dry coatings within the respective conduits. Controlled motion of the liquids within the cartridge further permits more than one substance to be amended into each liquid whenever the sample or fluid is moved to a new region of the conduit. In this way, provision is made for multiple amendments to each fluid, greatly extending the complexity of automated assays that can be performed, and therefore enhancing the utility of the present invention.

In a disposable cartridge, the amount of liquid contained is preferably kept small to minimize cost and size. Therefore, in the present invention, segments within the conduits may also be used to assist in cleaning and rinsing the conduits by passing the air-liquid interface of a segment over the sensor array or other region to be rinsed at least once. It has been found that more efficient rinsing, using less fluid, is achieved by this method compared to continuous rinsing by a larger volume of fluid.

Restrictions within the conduits serve several purposes in the present invention. In one embodiment, a capillary stop located between the sample holding chamber and first conduit is used to facilitate sample metering in the holding chamber by preventing displacement of the sample in the holding chamber until sufficient pressure is applied to overcome the resistance of the capillary stop. In another embodiment, a restriction within the second conduit is used to divert wash fluid along an alternative pathway towards the waste chamber when the fluid reaches the constriction. Small holes in the gasket, together with a hydrophobic coating, are provided to prevent flow from the first conduit to the second conduit until sufficient pressure is applied. Features that control the flow of liquids within and between the conduits of the present invention are herein collectively termed "valves."

One embodiment of the invention provides a single-use cartridge with a sample holding chamber connected to a first conduit that contains an analyte sensor or array of analyte sensors. A second conduit, partly containing a fluid, is connected to the first conduit and air segments can be introduced into the fluid in the second conduit in order to segment it. Pump means are provided to displace the sample within the first conduit, and this displaces fluid from the second conduit into the first conduit. Thus, the sensor or sensors can be contacted first by a sample and then by a second fluid.

In another embodiment, the cartridge includes a closeable valve located between the first conduit and a waste chamber. This embodiment permits displacement of the fluid from the second conduit into the first conduit using only a single pump means connected to the first conduit. This embodiment further permits efficient washing of the conduits of the cartridge of the present invention, which is an important feature of a small single-use cartridge. In operation, the sample is displaced to contact the sensors, and is then displaced through the closeable valve into the waste chamber. Upon wetting, the closeable valve seals the opening to the waste chamber, providing an airtight seal that allows fluid in the second conduit to be drawn into contact with the sensors using only the pump means connected to the first conduit. In this embodiment, the closeable valve permits the fluid to be displaced in this manner and prevents air from entering the first conduit from the waste chamber.

In another embodiment, both a closeable valve and means for introducing segments into the conduit are provided. This embodiment has many advantages, among which is the ability to reciprocate a segmented fluid over the sensor or array of sensors. Thus a first segment or set of segments is used to rinse a sensor, and then a fresh segment replaces it for taking measurements. Only one pump means (that connected to the first conduit) is required.

In another embodiment, analyte measurements are performed in a thin-film of liquid coating an analyte sensor. Such thin-film determinations are preferably performed amperometrically. This cartridge differs from the foregoing embodiments in having both a closeable valve that is sealed when the sample is expelled through the valve, and an air vent within the conduits that permits at least one air segment to be subsequently introduced into the measuring fluid, thereby increasing the efficiency with which the sample is rinsed from the sensor, and further permitting removal of substantially all the liquid from the sensor prior to measurement, and still further permitting segments of fresh liquid to be brought across the sensor to permit sequential, repetitive measurements for improved accuracy and internal checks of reproducibility.

In non-competitive assay embodiments, as discussed above, the analysis scheme for the detection of low concentrations of immunoactive analyte relies on the formation of an enzyme labeled antibody/analyte/surface-bound antibody "sandwich" complex. The concentration of analyte in a sample is converted into a proportional surface concentration of an enzyme. The enzyme is capable of amplifying the analyte's chemical signal by converting a substrate to a detectable product. For example, where alkaline phosphatase is the enzyme, a single enzyme molecule can produce about nine thousand detectable molecules per minute, providing several orders of magnitude improvement in the detectability of the analyte compared to schemes in which an electroactive species is attached to the antibody in place of alkaline phosphatase.

In immunosensor embodiments, it is advantageous to contact the sensor first with a sample and then with a wash fluid prior to recording a response from the sensor. In some specific embodiments, in addition to being amended with an IgG-coated microparticle in order to reduce leukocyte interference, the sample is amended with an antibody-enzyme conjugate (signal antibody) that binds to the analyte of interest within the sample before the amended sample contacts the sensor. Binding reactions in the sample produce an analyte/antibody-enzyme complex. The sensor comprises an immobilized antibody to the analyte, attached close to an electrode surface. Upon contacting the sensor, the analyte/antibody-enzyme complex binds to the immobilized antibody near the electrode surface. It is advantageous at this point to remove from the vicinity of the electrode as much of the unbound antibody-enzyme conjugate as possible to minimize background signal from the sensor. The enzyme of the antibody-enzyme complex is advantageously capable of converting a substrate, provided in the fluid, to produce an electrochemically active species. This active species is produced close to the electrode and provides a current from a redox reaction at the electrode when a suitable potential is applied (amperometric operation). Alternatively, if the electroactive species is an ion, it can be measured potentiometrically. In amperometric measurements the potential may either be fixed during the measurement, or varied according to a predetermined waveform. For example, a triangular wave can be used to sweep the potential between limits, as is used in the well-known technique of cyclic voltammetry. Alternatively, digital techniques such as square waves can be used to improve sensitivity in detection of the electroactive species adjacent to the electrode. From the current or voltage measurement, the amount or presence of the analyte in the sample is calculated. These and other analytical electrochemical methods are well known in the art.

In embodiments in which the cartridge comprises an immunosensor, the immunosensor is advantageously microfabricated from a base sensor of an unreactive metal such as gold, platinum or iridium, and a porous permselective layer which is overlaid with a bioactive layer attached to a microparticle, for example latex particles. The microparticles are dispensed onto the porous layer covering the electrode surface, forming an adhered, porous bioactive layer. The bioactive layer has the property of binding specifically to the analyte of interest, or of manifesting a detectable change when the analyte is present, and is most preferably an immobilized antibody directed against the analyte.

Figure 4:
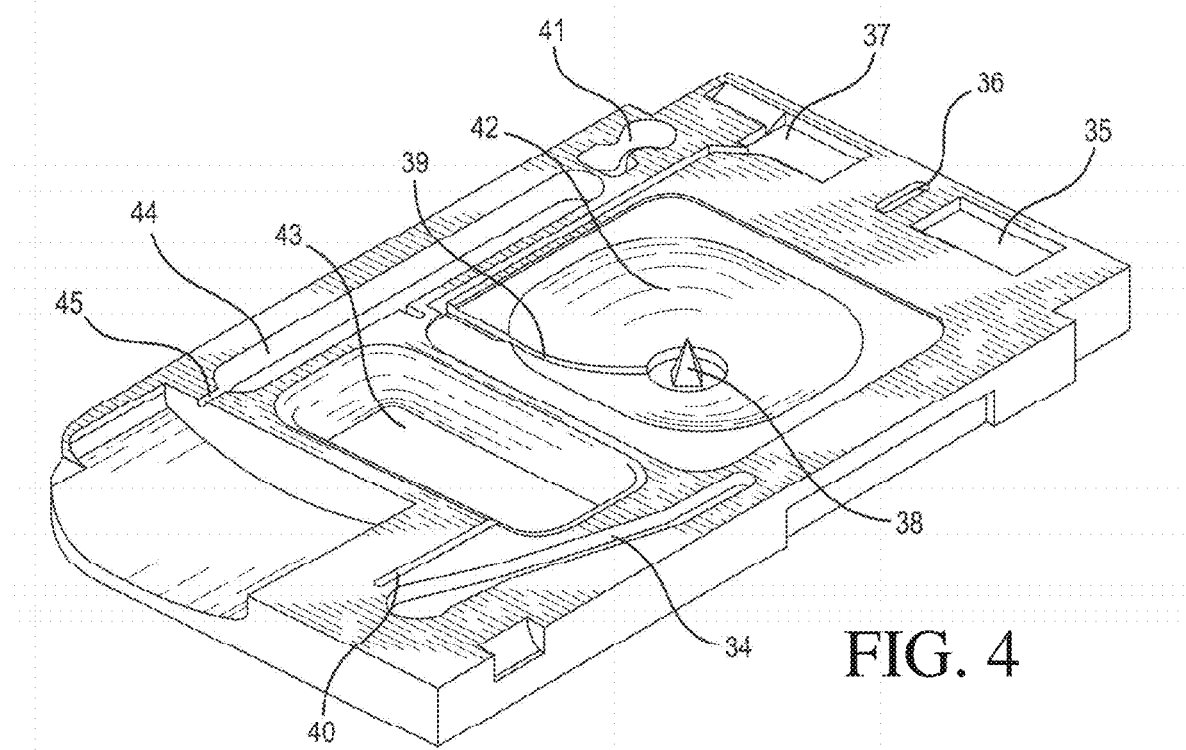
FIG. 4 is an isometric top view of an immunosensor cartridge base.

Referring to the Figures, the cartridge of the present invention comprises a cover, an embodiment of which is shown in FIGS. 1 and 2, a base, an embodiment of which is shown in FIG. 4, and a thin-film adhesive gasket, an embodiment of which is shown in FIG. 3, disposed between the base and the cover. Referring to FIG. 1, the cover 1 is made of a rigid material, preferably plastic, and is capable of repetitive deformation at flexible hinge regions 5, 9, 10 without cracking. The cover comprises a lid 2, attached to the main body of the cover by a flexible hinge 9. In operation, after introduction of a sample into the sample holding chamber 34, the lid can be secured over the entrance to the sample entry port 4, preventing sample leakage, and the lid is held in place by hook 3. The cover further comprises two paddles 6, 7, that are moveable relative to the body of the cover, and which are attached to it by flexible hinge regions 5, 10. Additionally in operation, when operated upon by a pump means, paddle 6 exerts a force upon an air bladder comprised of cavity 43, which is covered by thin-film gasket 21, to displace fluids within conduits of the cartridge. When operated by a second pump means, paddle 7 exerts a force upon the gasket 21, which can deform because of slits 22 cut therein. The cartridge is adapted for insertion into a reading apparatus, and therefore has a plurality of mechanical and electrical connections for this purpose. In other embodiments of the invention, manual operation of the cartridge is possible.

Upon insertion of the cartridge into a reading apparatus, the gasket transmits pressure onto a fluid-containing foil pack filled with approximately 130 µL of analysis/wash solution ("fluid") located in cavity 42, rupturing the package upon spike 38, and expelling fluid into conduit 39, which is connected via a short transecting conduit in the base to the sensor conduit. The analysis fluid fills the front of the analysis conduit first pushing fluid onto a small opening in the tape gasket that acts as a capillary stop. Other motions of the analyzer mechanism applied to the cartridge are used to inject one or more segments into the analysis fluid at controlled positions within the analysis conduit. These segments are used to help wash the sensor surface and the surrounding conduit with a minimum of fluid.

In some embodiments, the cover further comprises a hole covered by a thin pliable film 8. In operation, pressure exerted upon the film expels one or more air segments into a conduit 20 through a small hole 28 in the gasket.

Referring to FIG. 2, the lower surface of the base further comprises second conduit 11, and first conduit 15. Second conduit 11 includes a constriction 12, which controls fluid flow by providing resistance to the flow of a fluid. Optional coatings 13, 14 provide hydrophobic surfaces, which together with gasket holes 31, 32, control fluid flow between second and first conduits 11, 15. A recess 17 in the base provides a pathway for air in conduit 34 to pass to conduit 34 through hole 27 in the gasket.

Referring to FIG. 3, thin-film gasket 21 comprises various holes and slits to facilitate transfer of fluid between conduits within the base and the cover and to allow the gasket to deform under pressure where necessary. Thus, hole 24 permits fluid to flow from conduit 11 into waste chamber 44; hole 25 comprises a capillary stop between conduits 34 and 15; hole 26 permits air to flow between recess 18 and conduit 40; hole 27 provides for air movement between recess 17 and conduit 34; and hole 28 permits fluid to flow from conduit 19 to waste chamber 44 via optional closeable valve 41. Holes 30 and 33 permit the plurality of electrodes that are housed within cutaways 35 and 37, respectively, to contact fluid within conduit 15. In a specific embodiment, cutaway 37 houses a ground electrode, and/or a counter-reference electrode, and cutaway 35 houses at least one analyte sensor and, optionally, a conductimetric sensor. In FIG. 3, the tape 21 is slit at 22 to allow the tape enclosed by the three cuts 22 to deform when the instrument applies a downward force to rupture the calibrant pouch within element 42 on the barb 38. The tape is also cut at 23 and this allows the tape to flex downwards into element 43 when the instrument provides a downward force, expelling air from chamber 43 and moving the sample fluid through conduit 15 towards the sensors. Element 29 in FIG. 3 acts as an opening in the tape connecting a region in the cover FIG. 2 with the base FIG. 4.

Referring to FIG. 4, conduit 34 is the sample holding chamber that connects the sample entry port 4 to first conduit 11 in the assembled cartridge. Cutaway 35 houses the analyte sensor or sensors, or an analyte responsive surface, together with an optional conductimetric sensor or sensors. Cutaway 37 houses a ground electrode if needed as a return current path for an electrochemical sensor, and may also house an optional conductimetric sensor. Cutaway 36 provides a fluid path between gasket holes 31 and 32 so that fluid can pass between the first and second conduits. Recess 42 houses a fluid-containing package, e.g., a rupturable pouch, in the assembled cartridge that is pierced by spike 38 because of pressure exerted upon paddle 7 upon insertion into a reading apparatus. Fluid from the pierced package flows into the second conduit at 39. An air bladder is comprised of recess 43 which is sealed on its upper surface by gasket 21. The air bladder is one embodiment of a pump means, and is actuated by pressure applied to paddle 6 which displaces air in conduit 40 and thereby displaces the sample from sample chamber 34 into first conduit 15.

The location at which air enters the sample holding chamber (gasket hole 27) from the bladder, and the capillary stop 25, together define a predetermined volume of the sample holding chamber. An amount of the sample corresponding to this volume is displaced into the first conduit when paddle 6 is depressed. This arrangement is therefore one possible embodiment of a metering means for delivering a metered amount of an unmetered sample into the conduits of the cartridge.

In certain embodiments of the cartridge, a means for metering a sample segment is provided in the base plastic part. The segment size is controlled by the size of the compartment in the base and the position of the capillary stop and air pipe holes in the tape gasket. This volume can be readily varied from 2 to 200 µl. Expansion of this range of sample sizes is possible within the context of the present invention.

In some embodiments, the fluid is pushed through a pre-analytical conduit 11 that can be used to amend a reagent (e.g., particles, soluble molecules, or the IgM or fragments thereof) into the sample prior to its presentation at the sensor conduit 19. Alternatively, the amending reagent may be located in portion 15, beyond portion 16. Pushing the sample through the pre-analytical conduit also serves to introduce tension into the diaphragm pump paddle 7, which improves its responsiveness for actuation of fluid displacement.

According to certain embodiments of the invention, metering is advantageous in some assays if quantification of the analyte is required. A waste chamber is provided, 44, for sample and/or fluid that is expelled from the conduit, to prevent contamination of the outside surfaces of the cartridge. A vent connecting the waste chamber to the external atmosphere is also provided, 45. One desirable feature of the cartridge is that once a sample is loaded, analysis can be completed and the cartridge discarded without the operator or others contacting the sample.

Figure 5:
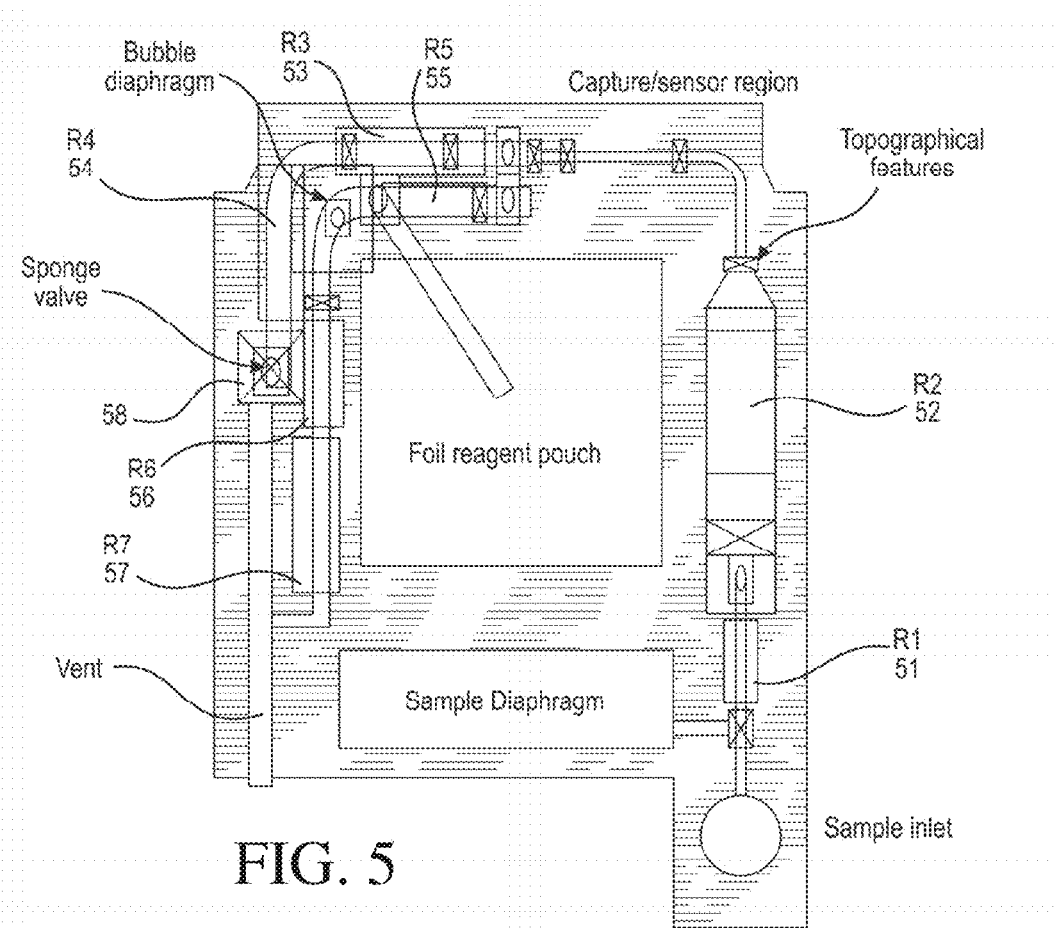
FIG. 5 is a schematic view of the layout of an immunosensor cartridge.

Referring now to FIG. 5, a schematic diagram of the features of a cartridge and components is provided, wherein 51-57 are portions of the conduits and sample chamber that can optionally be coated with dry reagents to amend a sample or fluid. The sample or fluid is passed at least once over the dry reagent to dissolve it. Reagents used to amend the sample may include one or more of the following: antibody-enzyme conjugates (signal antibodies), one or more leukocidal reagents, IgM and/or fragments thereof, IgG and/or fragments thereof, and other blocking agents that prevent either specific or non-specific binding reactions among assay compounds, and/or the above-described IgG-coated microparticles for reducing leukocyte interference. A surface coating that is not soluble but helps prevent non-specific adsorption of assay components to the inner surfaces of the cartridges can also be provided.

In specific embodiments, a closeable valve is provided between the first conduit and the waste chamber. In one embodiment, this valve, 58, is comprised of a dried sponge material that is coated with an impermeable substance. In operation, contacting the sponge material with the sample or a fluid results in swelling of the sponge to fill the cavity 41 (FIG. 4), thereby substantially blocking further flow of liquid into the waste chamber 44. Furthermore, the wetted valve also blocks the flow of air between the first conduit and the waste chamber, which permits the first pump means connected to the sample chamber to displace fluid within the second conduit, and to displace fluid from the second conduit into the first conduit in the following manner.

Figure 6:
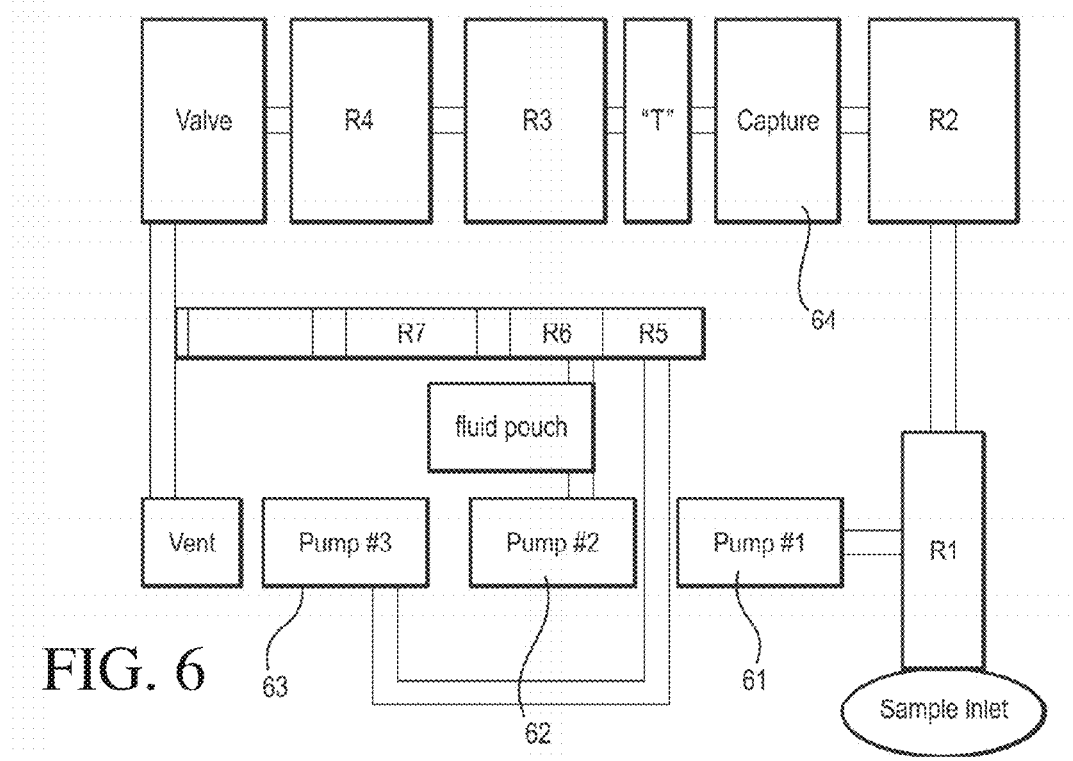
FIG. 6 is a schematic view of the fluid and air paths within an immunosensor cartridge, including sites for amending fluids with dry reagents.

Referring now to FIG. 6, which illustrates the schematic layout of an immunosensor cartridge, there are provided three pumps, 61-63. While these pumps have been described in terms of specific embodiments, it will be readily understood that any pumping device capable of performing the respective functions of pumps 61-63 may be used within the present invention. Thus, pump 1, 61, should be capable of displacing the sample from the sample holding chamber into the first conduit; pump 2, 62, should be capable of displacing fluid within the second conduit; and pump 3, 63, should be capable of inserting at least one segment into the second conduit. Other types of pumps that are envisaged in the present application include, but are not limited to, an air sac contacting a pneumatic means whereby pressure is applied to the air sac, a flexible diaphragm, a piston and cylinder, an electrodynamic pump, and a sonic pump. With reference to pump 3, 63, the term "pump" includes all devices and methods by which one or more segments are inserted into the second conduit, such as a pneumatic means for displacing air from an air sac, a dry chemical that produces a gas when dissolved, or a plurality of electrolysis electrodes operably connected to a current source. In a specific embodiment, the segment is produced using a mechanical segment generating diaphragm that may have more than one air bladder or chamber. As shown, the well 8 has a single opening which connects the inner diaphragm pump and the fluid filled conduit into which a segment is to be injected 20. The diaphragm can be segmented to produce multiple segments, each injected in a specific location within a fluid filled conduit. In FIG. 6, element 64 indicates the region where the immunosensor performs the capture reaction to form a sandwich comprising the immobilized antibody, the analyte and the signal antibody.

In alternative embodiments, a segment is injected using a passive feature. A well in the base of the cartridge is sealed by the tape gasket. The tape gasket covering the well has two small holes on either end. One hole is open while the other is covered with a filter material which wets upon contact with a fluid. The well is filled with a loose hydrophilic material such as a cellulose fiber filter, paper filter or glass fiber filter. This hydrophilic material draws the liquid into the well in the base via capillary action, displacing the air that was formerly in the well. The air is expelled through the opening in the tape gasket creating a segment whose volume is determined by the volume of the well and the void volume of the loose hydrophilic material. The filter used to cover one of the inlets to the well in the base can be chosen to meter the rate at which the fluid fills the well and thereby control the rate at which the segment is injected into the conduit in the cover. This passive feature permits any number of controlled segments to be injected at specific locations within a fluid path and requires a minimum of space.

IX. Devices, Kits and Methods for Reducing or Eliminating Leukocyte Interference Based on the disclosure herein, it is apparent that embodiments of the present invention provide a method of reducing or eliminating interference from leukocytes in an analyte immunoassay.

Preferred embodiments are directed to the performance of an immunoassay for a target analyte in a blood sample by contacting a sample with a leukocidal reagent that substantially inhibits activity of leukocytes in the sample. An immunoassay is also performed on the sample to detect a target analyte. As described herein, in some embodiments, the leukocidal reagent can be an oxygen depleting reagent and a glucose depleting reagent, e.g., glucose oxidase with or without an electron acceptor. In other embodiments, the reagent may constitute hexokinase and a source of ATP, e.g. creatine kinase, ADP and creatine phosphate. Another alternative is a glucose dehydrogenase, with for example NAD, NADH oxidase and an electron acceptor, or GDH-PQQ. In other embodiments, an oxygen depleting reagent, e.g. dithionite, glucose oxidase (with or without added glucose) and ascorbate oxidase can be used.

The present invention further constitutes embodiments where the leukocidal reagent is a mitochondrial electron transport inhibitor and/or a mitochondrial membrane uncoupling agent, e.g. cyanide, antimycin, rotenone, malonate, carbonyl cyanide p-[trifluoromethoxyl]-phenyl-hydrozone, 2,4-dinitrophenol and oligomycin. In additional embodiments, the reagent may be an amphipathic reagent, e.g. a saponin, a leukocidin and a mucopolysaccharide. Another alternative is the use of a monoclonal antibody AHN-1, which inhibits phagocytosis by human neutrophils, see Skubitz et al, Blood 65, 333-339, (1985), which is herein incorporated by reference.

The present invention is equally applicable to both sandwich and competitive immunoassays. In sandwich assay embodiments, the sample contacts an immunosensor with an immobilized first antibody to the target analyte, and a labeled second antibody to said target analyte. In competitive assay embodiments, the sample contacts an immunosensor comprising an immobilized first antibody to said target analyte, and a labeled target analyte that competes for binding with the target analyte. Typical analytes include, but are not limited to TnI, TnT, BNP, NTproBNP, proBNP, HCG, TSH, NGAL, digoxin, theophylline and phenyloin and the like.

In some embodiments of the invention, the sample, e.g., whole blood sample, is first collected and then amended by dissolving a dry reagent comprising one or more leukocidal reagents and optionally sacrificial beads into the sample. In certain embodiments, sufficient sacrificial beads are utilized to provide an excess of beads with respect to leukocytes in a blood sample. This yields a sample with a dissolved sacrificial bead concentration of at least 5 micrograms per microliter of sample, e.g., at least 10 micrograms per microliter of sample, or at least 15 micrograms per microliter of sample, which is sufficient to substantially engage any leukocytes in the sample. In terms of ranges, the dry reagent preferably dissolves into the sample to give a sacrificial bead concentration of from about 5 micrograms to about 40 micrograms beads per microliter of sample, preferably from about 10 to about 20 micrograms beads per microliter of sample. Depending on the size of the beads, this corresponds to at least about $10^4$ beads per microliter of sample, at least about $10^5$ beads per microliter of sample, or approximately from about $10^5$ to about $10^6$ beads per microliter of sample. Thus, in some preferred embodiments, in addition to the leukocidal reagent, the sacrificial beads are present in an amount sufficient to provide a dissolved sacrificial bead concentration of at least $10^4$ beads per microliter of sample, e.g., at least about $10^5$ beads per microliter of sample, or from about $10^5$ to about $10^6$ beads per microliter of sample. Once this step is completed, it is possible to perform an immunoassay, e.g., an electrochemical immunoassay, on the amended sample to determine the concentration of an analyte.

The dissolution of the dry reagents and the sandwich formation step can occur concurrently or in a stepwise manner. Embodiments of the method of the present invention are directed mainly to analytes that are cardiovascular markers, e.g., TnI, TnT, CKMB, myoglobin, BNP, NT-proBNP, and proBNP, but can also be used for other markers such as, for example, beta-HCG, TSH, myeloperoxidase, myoglobin, D-dimer, CRP, NGAL and PSA. To ensure that the majority of the leukocytes are sequestered before the detection step, it is preferable that the sample amendment step is for a selected predetermined period in the range of about 1 minute to about 30 minutes.

In preferred embodiments, the method is performed in a cartridge comprising an immunosensor, a conduit, a sample entry port and a sample holding chamber, where at least a portion of at least one of these elements is coated with the dry reagent. Note that the dry reagent can include one or more of: a leukocidal reagent, sacrificial beads for reducing leukocyte interference, buffer, salt, surfactant, stabilizing agent, a simple carbohydrate, a complex carbohydrate and various combinations. In addition, the dry reagent can also include an enzyme-labeled antibody (signal antibody) to the analyte.

If sacrificial beads are employed, as suggested above, in addition to or instead of coating the sacrificial beads using whole IgG molecules, where the individual monomers are formed from an Fc region attached to a F(ab')$_2$ region, which in turn comprises two Fab regions, it is also possible to use fragments of IgG. IgG fragmentation can be achieved variously using combinations of disulphide bond reduction (—S—S— to —SHHS—) and enzymatic pepsin or papain digestion, to create some combination of F(ab')2 fragments, Fab fragments, and/or Fc fragments. These fragments can be separated for use separately by chromatography, or used in combination. For example, where the blocking site is on the Fc fragment, this can be used instead of the whole IgG molecule. The same applies to the Fab fragment and the F(ab')2 fragment.

In the actual assay step, in preferred embodiments, once the sandwich is formed between the immobilized and signal antibodies, the sample medium is subsequently washed to a waste chamber, followed by exposing the sandwich to a substrate capable of reacting with an enzyme to form a product capable of electrochemical detection. The preferred format is an electrochemical enzyme-linked immunosorbent assay.

Preferably, the device is one that performs an immunoassay of an analyte in a sample, e.g., blood sample, with reduced interference from leukocytes. The device is a housing with an electrochemical immunosensor, a conduit and a sample entry port, where the conduit permits the sample to pass from the entry port to the immunosensor in a controlled manner.

In one aspect, samples containing an analyte of interest may be amended with one or more leukocidal reagents that reduce or eliminate the activity of leukocytes, as described above, and the resulting amended sample may be analyzed in an immunoassay to determine analyte content and/or concentration without significant leukocyte interference. In preferred embodiments, the impaired activity is phagocytosis. With regard to various preferred embodiments of the invention, such embodiments include modifying whole blood samples with glucose oxidase and glucose to give respective sample concentrations above about 3 IU per mL and 500 mg/dL, with or without saponin at about 0.5 mg/mL, and with or without opsonized decoy beads as described herein.

In another aspect, in addition to amending the sample with the one or more leukocidal reagents, at least a portion of the housing may be coated with a dry reagent which can comprise non-human IgG-coated sacrificial beads. The important feature is that the dry reagent is capable of dissolving into the sample and engaging leukocytes in binding and preferably phagocytosis. This is generally sufficient to sequester potentially interfering leukocytes in the sample.

In a preferred embodiment, the device also comprises an immuno-reference sensor. The immunosensor is preferably directed to detect a cardiovascular marker, e.g., analytes such as TnI, TnT, CKMB, myoglobin, BNP, NT-proBNP, and proBNP. The system in which the device operates generally allows the sample to remain in contact with the reagent for a predetermined period, e.g., from 1 to 30 minutes. Preferably the device is a single-use cartridge, e.g., filled with a single sample, used once for the test and then discarded. Generally, the device includes a wash fluid capable of washing the sample to a waste chamber, and a substrate capable of reacting with the enzyme sandwich at the immunosensor to form a product suitable for electrochemical detection.

More broadly the invention relates to reducing interference from leukocytes in an analyte immunoassay for any biological sample where leukocytes are generally present. Furthermore, performing an immunoassay on the amended sample to determine the concentration of the selected analyte can be based on various techniques including electrochemical ones, e.g., amperometric and potentiometric, and also optical ones, e.g., absorbance, fluorescence and luminescence.

Various embodiments of the present invention are directed to a kit for performing an immunoassay for a target analyte in a whole blood sample comprising a leukocidal reagent wherein said reagent substantially inhibits activity of leukocytes in a sample, and immunoassay reagents for detecting a target analyte. Other embodiments of the invention are directed to a kit for performing an immunoassay for an analyte suspected of being present in a blood sample where the kit comprises one or more leukocidal reagents, sacrificial beads opsonized to leukocytes, an immobilized first antibody to the analyte and a second labeled antibody to the analyte. In addition a current immunoassay format known in the art may be modified to include the sacrificial beads, for example by adding the beads in a sample pre-treatment step. This pretreatment may be accomplished by incorporating the sacrificial beads in a blood collection device, in a separate vessel, or may take place in the analytical (immunoassay) device itself by incorporation of the sacrificial beads in the test cycle of the device.

While the present invention has been described in the context of a BNP test cartridge, it is equally applicable to any immunoassay where leukocytes are present and can be the cause of interference. The method or kit is not limited to BNP but can be adapted to any immunoassay, including but not limited to proBNP, NTproBNP, cTnI, TnT, HCG, TSH, PSA, D-dimer, CRP, myoglobin, NGAL, CKMB and myeloperoxidase. Furthermore the method and kit is applicable to assays where the sacrificial beads, if employed, are coated with any non-human IgG or a fragment thereof, including murine, caprine, bovine and lupine, and alternatively sacrificial beads coated with an activated human IgG or fragment thereof. The sacrificial beads may comprise substrate beads coated with a material or fragment thereof selected from a protein, a bacterium, a virus and a xenobiotic, or may be afforded by dormant or otherwise stabilized bacterial cells, spores or fragment thereof, e.g., *E. coli*, optionally without substrate beads.

While certain assays described above use an immobilized first antibody attached to an assay bead which is in turn attached to a porous layer with an underlying electrode, the first antibody may be immobilized directly onto an electrode or any other surface, or immobilized on a soluble bead.

The kit or method of the present invention can comprise a second labeled antibody that is in the form of a dissolvable dry reagent. In some embodiments, the dissolvable dry reagent includes one or more leukocidal reagents and optionally opsonized sacrificial beads as part of the dissolvable dry reagent, or where the various components are in separate dry reagent locations. Note that both the immobilized and labeled antibodies can be monoclonal, polyclonal, fragments thereof and combinations thereof. In addition, the second antibody can be labeled with various labels including a radiolabel, enzyme, chromophore, fluorophore, chemiluminescent species and other known in the immunoassay art. Where the second antibody is labeled with an enzyme, it is preferably ALP, horseradish peroxidase, or glucose oxidase.

The kit or method is applicable to any sample containing leukocytes, e.g., whole blood, and can be a blood sample amended with an anticoagulant, e.g., EDTA, heparin, fluoride, citrate and the like.

Where the method or kit is used to perform a non-competitive immunoassay there may be a sequence of mixing steps including: (i) mixing a blood sample suspected of containing an analyte with reagent (including one or more leukocidal reagents) and optionally opsonized sacrificial beads; (ii) mixing the blood sample with an immobilized first antibody to the analyte and forming a complex between the immobilized antibody and said analyte; and (iii) mixing the blood sample with a labeled second antibody to form a complex with said analyte and said immobilized antibody. Note that these mixing steps can be performed at the same time or in an ordered sequence. For example, steps (ii) and (iii) may occur at the same time, or steps (i) and (iii) may be performed before step (ii). In the final step there is a determination of the amount of complex formed between the immobilized first antibody, the analyte and the labeled second antibody.

Embodiments of the method of the present invention are directed to substantially ameliorating white blood cell accumulation on an analyte immunosensor. In some embodiments, the immunosensor is made from an anti-body-based reagent and/or antibody-coated assay beads to the analyte. After mixing a sample suspected of containing an analyte with the one or more leukocidal reagents and optionally opsonized sacrificial beads to form an amended sample where white blood cells in the sample preferentially are ameliorated by the one or more leukocidal reagents or seek to preferentially phagocytose the sacrificial beads, if present, the amended sample is then contacted with the immunosensor. As a result there is minimal accumulation of white cells, and a reliable assay may be achieved.

The present method is directed to performing an immunoassay for an analyte suspected of being present in a blood sample comprising: mixing a blood sample suspected of containing an analyte with one or more leukocidal reagents and optionally with an excess of opsonized sacrificial beads to form an amended sample wherein white blood cells in the sample are ameliorated with the leukocidal reagents and/or preferentially seek to phagocytose the sacrificial beads (if present); contacting the amended sample with an immunosensor comprising antibody-coated beads to the analyte immobilized on an electrode; forming a sandwich between said antibody-coated bead, said analyte and a second labeled antibody; washing said blood sample from said immunosensor; and determining the amount of said sandwiched label with said immunosensor and relating the amount of said label to the concentration of the analyte in the sample.

The present method is also directed to performing an immunoassay for an analyte suspected of being present in a blood sample comprising: mixing a blood sample suspected of containing an analyte with one or more leukocidal reagents and optionally with an excess of opsonized sacrificial beads to form an amended sample wherein white blood cells in the sample are ameliorated with the one or more leukocidal reagents and, if present, preferentially seek to phagocytose the sacrificial beads; contacting the amended sample with the reagent and/or beads to the analyte; forming a sandwich between said reagent and/or beads, said analyte and a second labeled antibody; washing said blood sample from said reagent and/or beads; and determining the amount of said sandwiched label and relating the amount of said label to the concentration of the analyte in the sample.

The present invention is also directed to a test cartridge for performing an immunoassay for an analyte suspected of being present in a blood sample comprising: an immunosensor in a conduit wherein said immunosensor having an immobilized first antibody to the analyte. In some embodiments, the conduit preferably has a dry reagent coating or separate coatings comprising one or more leukocidal reagents and optionally sacrificial beads opsonized to leukocytes and a second labeled antibody to said analyte. In operation, the dry reagent dissolves into said blood sample.

EXAMPLES

The present invention will be better understood in view of the following non-limiting Examples.

Example 1

Figure 7:
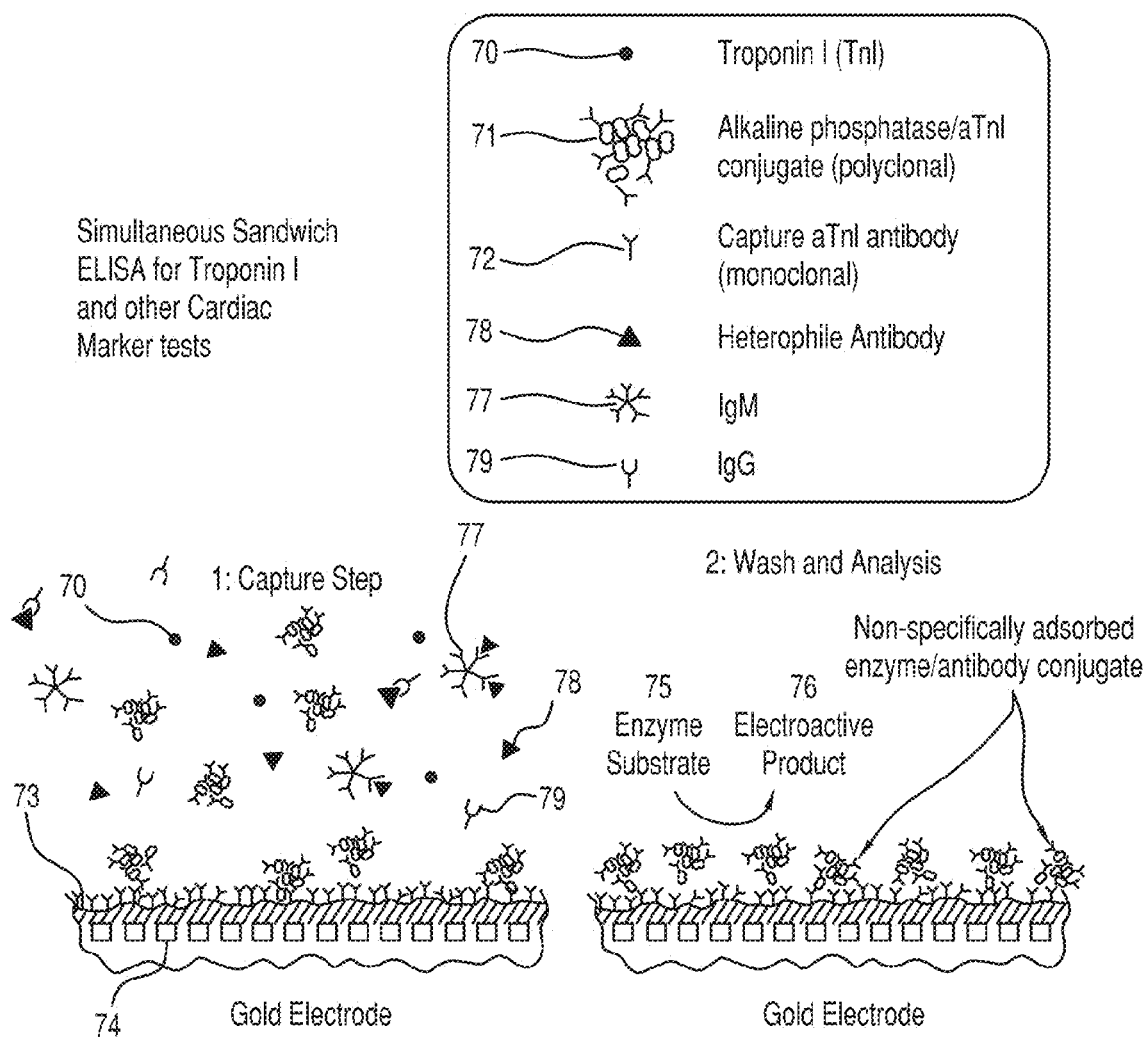
FIG. 7 illustrates the principle of operation of an electrochemical immunosensor with the inclusion of IgM.

FIG. 7 illustrates the principle of an amperometric immunoassay according to specific embodiments of U.S. application Ser. No. 12/411,325, referenced above and incorporated herein by reference in its entirety for determining the presence and amount of troponin I (TnI), a marker of cardiac necrosis. A blood sample was introduced into the sample holding chamber of a cartridge and was amended by dissolution of a dry reagent coated into the sample holding chamber. The dry reagent includes IgM 77, which upon dissolution into the sample selectively binds to complementary heterophile antibodies 78 that may be contained in the sample. As shown, the dry reagent also comprises IgG 79, which also selectively binds to complementary antibodies 78 after dissolution into the sample.

Figure 10:
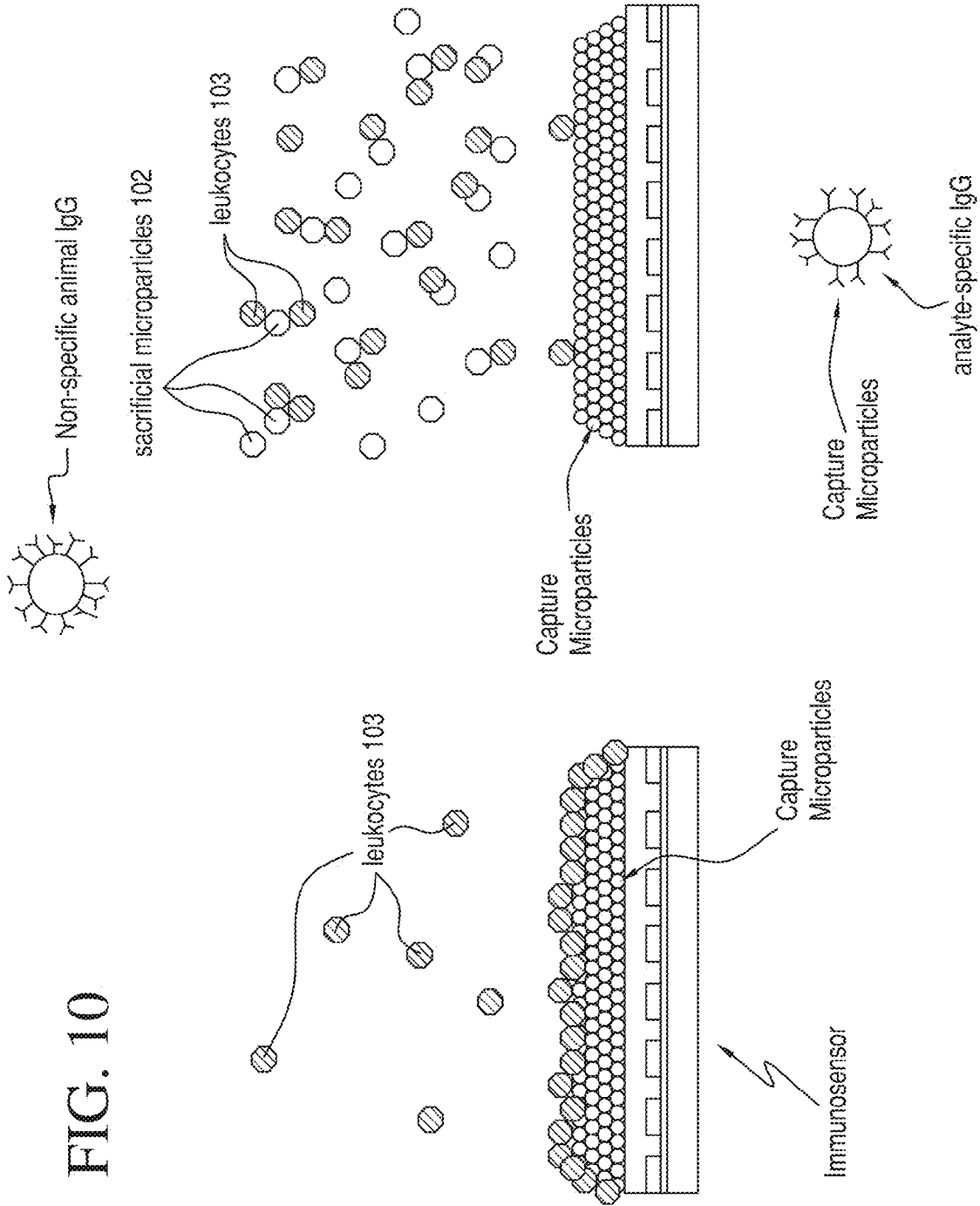
FIG. 10 illustrates the principle of operation of an electrochemical immunosensor with the inclusion of sacrificial beads opsonized for leukocytes.

FIG. 10 illustrates the principle of an amperometric immunoassay according to U.S. patent application Ser. Nos. 12/620,179 and 12/620,230, for determining the presence and amount of a marker of cardiac function, e.g., BNP and TnI, and employing opsonized sacrificial beads for reducing leukocyte interference. A blood sample was introduced into the sample holding chamber of a cartridge and was amended by dissolution of a dry reagent coated into the sample holding chamber. The dry reagent includes sacrificial beads 102, which upon dissolution into the sample selectively bind to leukocytes 103 that may be contained in the sample. Note that the dry reagent may also and preferably comprises IgM and IgG as described for FIG. 7.

In addition, FIGS. 7 and 10 show a conjugate molecule comprising alkaline phosphatase enzyme (AP) covalently attached to a signal antibody 71, e.g., polyclonal anti-troponin I antibody, also was dissolved into the sample. This conjugate specifically binds to the analyte 70, e.g., TnI or BNP, in the blood sample producing a complex made up of analyte bound to the AP conjugate. In a capture step, this complex binds to the capture antibody 72 (immobilized antibody) attached on, or close to, the immunosensor. The sensor chip has a conductivity sensor, which is used to monitor when the sample reaches the sensor chip. The time of arrival of the fluid can be used to detect leaks within the cartridge, e.g., a delay in arrival signals a leak. In some embodiments, the position of the sample segment within the sensor conduit can be actively controlled using the edge of the fluid as a position marker. As the sample/air interface crosses the conductivity sensor, a precise signal is generated which can be used as a fluid marker from which controlled fluid excursions can be executed. The fluid segment is preferentially oscillated edge-to-edge over the sensor in order to present the entire sample to the immunosensor surface. A second reagent can be introduced in the sensor conduit beyond the sensor chip, which becomes homogenously distributed during the fluid oscillations.

The sensor chip contains a capture region or regions coated with antibodies for the analyte of interest. These capture regions are defined by a hydrophobic ring of polyimide or another photolithographically produced layer. A microdroplet or several microdroplets (approximately 5 to 40 nanoliters in size) containing antibodies in some form, for example bound to latex microspheres, is dispensed on the surface of the sensor or on a permselective layer on the sensor. The photodefined ring contains this aqueous droplet allowing the antibody coated region to be localized to a precision of a few microns. The capture region can be made from 0.03 to roughly 2 square millimeters in size. The upper end of this size is limited by the size of the conduit and sensor in present embodiments, and is not a limitation of the invention.

Thus, the gold electrode 74 is coated with a biolayer 73, e.g., a covalently attached anti-troponin I antibody, to which the TnI/AP-aTnI complex binds. AP is thereby immobilized close to the electrode in proportion to the amount of analyte initially present in the sample. In addition to specific binding, the enzyme-antibody conjugate may bind non-specifically to the sensor. Non-specific binding provides a background signal from the sensor that is undesirable and preferably is minimized. As described above, the rinsing protocols, and in particular the use of segmented fluid to rinse the sensor, provide efficient means to minimize this background signal. In a second step subsequent to the rinsing step, a substrate 75 that is hydrolyzed by, for example, alkaline phosphatase to produce an electroactive product 76 is presented to the sensor. In specific embodiments the substrate is comprised of a phosphorylated ferrocene or p-aminophenol. The amperometric electrode is either poised at a fixed electrochemical potential sufficient to oxidize or reduce a product of the hydrolyzed substrate but not the substrate directly, or the potential is swept one or more times through an appropriate range. Optionally, a second electrode may be coated with a layer where the complex of analyte/AP anti-analyte, e.g., TnI/AP-aTnI, is made during manufacture to act as a reference sensor or calibration means for the measurement.

In the present example, the sensor comprises two amperometric electrodes which are used to detect the enzymatically produced 4-aminophenol from the reaction of 4-aminophenylphosphate with the enzyme label alkaline phosphatase. The electrodes are preferably produced from gold surfaces coated with a photodefined layer of polyimide. Regularly spaced openings in the insulating polyimide layer define a grid of small gold electrodes at which the 4-aminophenol is oxidized in a two electron per molecule reaction. Sensor electrodes further comprise a biolayer, while reference electrodes can be constructed, for example, from gold electrodes lacking a biolayer, or from silver electrodes, or other suitable material. Different biolayers can provide each electrode with the ability to sense a different analyte.

Substrates, such as p-aminophenol species, can be chosen such that the E(½) of the substrate and product differ substantially. Preferably, the voltammetric half-wave potential E(½) of the substrate is substantially higher (more positive) than that of the product. When the condition is met, the product can be selectively electrochemically measured in the presence of the substrate.

The size and spacing of the electrode play an important role in determining the sensitivity and background signal. Important parameters in the grid include the percentage of exposed metal and the spacing between the active electrodes. The position of the electrode can be directly underneath the antibody capture region or offset from the capture region by a controlled distance. The actual amperometric signal of the electrodes depends on the positioning of the sensors relative to the antibody capture site and the motion of the fluid during the analysis. A current at the electrode is recorded that depends upon the amount of electroactive product in the vicinity of the sensor.

The detection of alkaline phosphatase activity in this example relies on a measurement of the 4-aminophenol oxidation current. This is achieved at a potential of about +60 mV versus the Ag/AgCl ground chip. The exact form of detection used depends on the sensor configuration. In one version of the sensor, the array of gold microelectrodes is located directly beneath the antibody capture region. When the analysis fluid is pulled over this sensor, enzyme located on the capture site converts the 4-aminophenylphosphate to 4-aminophenol in an enzyme limited reaction. The concentration of the 4-aminophenylphosphate is selected to be in excess, e.g., 10 times the Km value. The analysis solution is 0.1 M in diethanolamine, 1.0 M NaCl, buffered to a pH of 9.8. In additional embodiments, the analysis solution contains 0.5 mM $MgCl_2$, which is a cofactor for the enzyme. Alternatively, a carbonate buffer has the desired properties.

In another electrode geometry embodiment, the electrode is located a few hundred microns away from the capture region. When a fresh segment of analysis fluid is pulled over the capture region, the enzyme product builds with no loss due to electrode reactions. After time, the solution is slowly pulled from the capture region over the detector electrode resulting in a current spike from which the enzyme activity can be determined.

An important consideration in the sensitive detection of alkaline phosphatase activity is the non-4-aminophenol current associated with background oxidations and reductions occurring at the gold sensor. Gold sensors tend to give significant oxidation currents in basic buffers at these potentials. The background current is largely dependent on the buffer concentration, the area of the gold electrode (exposed area), surface pretreatments and the nature of the buffer used. Diethanolamine is a particularly good activating buffer for alkaline phosphatase. At molar concentrations, the enzymatic rate is increased by about three times over a non-activating buffer such as carbonate.

In alternative embodiments, the enzyme conjugated to an antibody or other analyte-binding molecule is urease, and the substrate is urea. Ammonium ions produced by the hydrolysis of urea are detected in this embodiment by the use of an ammonium sensitive electrode. Ammonium-specific electrodes are well-known to those of skill in the art. For example, a suitable microfabricated ammonium ion-selective electrode is disclosed in U.S. Pat. No. 5,200,051, incorporated herein by reference. Other enzymes that react with a substrate to produce an ion are known in the art, as are other ion sensors for use therewith. For example, phosphate produced from an alkaline phosphatase substrate can be detected at a phosphate ion-selective electrode.

Figure 8:
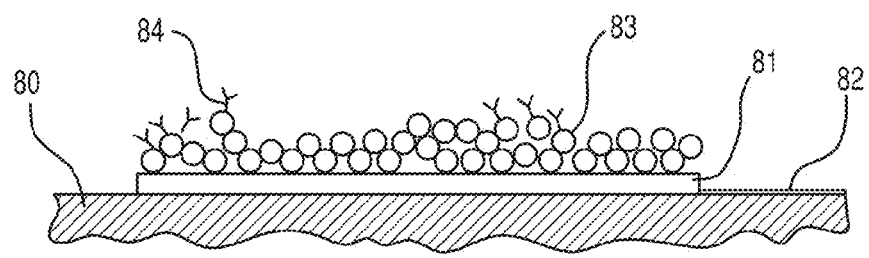
FIG. 8 is a side view of the construction of an electrochemical immunosensor with antibody-labeled particles not drawn to scale.

FIG. 8 illustrates the construction of an embodiment of a microfabricated immunosensor. Preferably a planar non-conducting substrate 80 is provided onto which is deposited a conducting layer 81 by conventional means or microfabrication known to those of skill in the art. The conducting material is preferably a noble metal such as gold or platinum, although other unreactive metals such as iridium may also be used, as may non-metallic electrodes of graphite, conductive polymer, or other materials. An electrical connection 82 is also provided. A biolayer 83 is deposited onto at least a portion of the electrode. In the present disclosure, a "biolayer" refers to a porous layer comprising on its surface a sufficient amount of a molecule 84 that can either bind to an analyte of interest, or respond to the presence of such analyte by producing a change that is capable of measurement. Optionally, a permselective screening layer may be interposed between the electrode and the biolayer to screen electrochemical interferents, as described in U.S. Pat. No. 5,200,051, referenced above.

In specific embodiments, a biolayer is constructed from latex beads of specific diameter in the range of about 0.001 to 50 microns. The beads are modified by covalent attachment of any suitable molecule consistent with the above definition of a biolayer. Many methods of attachment exist in the art, including providing amine reactive N-hydroxysuccinimide ester groups for the facile coupling of lysine or N-terminal amine groups of proteins. In specific embodiments, the biomolecule is chosen from among ionophores, cofactors, polypeptides, proteins, glycopeptides, enzymes, immunoglobulins, antibodies, antigens, lectins, neurochemical receptors, oligonucleotides, polynucleotides, DNA, RNA, or suitable mixtures. In more specific embodiments, the biomolecule is an antibody selected to bind one or more of human chorionic gonadotrophin, troponin I, troponin T, troponin C, a troponin complex, creatine kinase, creatine kinase subunit M, creatine kinase subunit B, myoglobin, myosin light chain, or modified fragments of these. Such modified fragments are generated by oxidation, reduction, deletion, addition or modification of at least one amino acid, including chemical modification with a natural moiety or with a synthetic moiety. Preferably, the biomolecule binds to the analyte specifically and has an affinity constant for binding analyte ligand of about $10^{-7}$ to $10^{-15}$ M.

In one embodiment, the biolayer, comprising beads having surfaces that are covalently modified by a suitable molecule, is affixed to the sensor by the following method. A microdispensing needle is used to deposit onto the sensor surface a small droplet, preferably about 20 nL, of a suspension of modified beads. The droplet is permitted to dry, which results in a coating of the beads on the surface that resists displacement during use.

In addition to immunosensors in which the biolayer is in a fixed position relative to an amperometric sensor, the present invention also envisages embodiments in which the biolayer is coated upon particles, e.g., assay beads, that are mobile. The cartridge can contain mobile microparticles capable of interacting with an analyte, for example magnetic particles that are localized to an amperometric electrode subsequent to a capture step, whereby magnetic forces are used to concentrate the particles at the electrode for measurement. One advantage of mobile microparticles in the present invention is that their motion in the sample or fluid accelerates binding reactions, making the capture step of the assay faster. For embodiments using non-magnetic mobile microparticles, a porous filter is used to trap the beads at the electrode. Note that with respect to the sacrificial beads, where the assay beads are magnetic, the sacrificial beads are preferably non-magnetic and sequestered separately. In addition, where the assay beads are non-magnetic, the sacrificial beads are preferably magnetic and sequestered separately.

Referring now to FIG. 9, there is illustrated a mask design for several electrodes upon a single substrate. By masking and etching techniques, independent electrodes and leads can be deposited. Thus, a plurality of immunosensors, 94 and 96, and conductimetric sensors, 90 and 92, are provided in a compact area at low cost, together with their respective connecting pads, 91, 93, 95, and 97, for effecting electrical connection to the reading apparatus. In principle, a very large array of sensors can be assembled in this way, each sensitive to a different analyte or acting as a control sensor or reference immunosensor.

In specific embodiments of the invention, immunosensors may be prepared as follows. Silicon wafers are thermally oxidized to form an insulating oxide layer approximately 1 micron thick. A titanium/tungsten layer is sputtered onto the oxide layer to a preferable thickness of between 100 to 1000 Angstroms, followed by a layer of gold that is most preferably 800 Angstroms thick. Next, a photoresist is spun onto the wafer and is dried and baked appropriately. The surface is then exposed using a contact mask, such as a mask corresponding to that illustrated in FIG. 9. The latent image is developed, and the wafer is exposed to a gold-etchant. The patterned gold layer is coated with a photodefinable polyimide, suitably baked, exposed using a contact mask, developed, cleaned in an $O_2$ plasma, and preferably imidized at 350° C. for 5 hours. An optional metallization of the back side of the wafer may be performed to act as a resistive heating element, where the immunosensor is to be used in a thermostatted format. The surface is then printed with antibody-coated particles. Droplets, preferably of about 20 nL volume and containing 1% solid content in deionized water, are deposited onto the sensor region and are dried in place by air drying. Optionally, an antibody stabilization reagent (supplied by SurModica Corporation, Eden Prairie, Minn., USA or Applied Enzyme Technology Ltd, Pontypool, UK) is overcoated onto the sensor.

Drying the particles causes them to adhere to the surface in a manner that prevents dissolution in either sample or fluid containing a substrate. This method provides a reliable and reproducible immobilization process suitable for manufacturing sensor chips in high volume.

Example 2

With respect to the method of use of a cartridge, in one embodiment, an unmetered fluid sample is introduced into sample holding chamber 34 of a cartridge, through sample entry port 4. Capillary stop 25 prevents passage of the sample into conduit 15 at this stage, and holding chamber 34 is filled with the sample. Lid 2 or element 200 is closed to prevent leakage of the sample from the cartridge. The cartridge is then inserted into a reading apparatus, such as that disclosed in U.S. Pat. No. 5,821,399 to Zelin, which is hereby incorporated by reference. Insertion of the cartridge into a reading apparatus activates the mechanism, which punctures a fluid-containing package located at 42 when the package is pressed against spike 38. Fluid is thereby expelled into the second conduit, arriving in sequence at 39, 20, 12 and 11. The constriction at 12 prevents further movement of fluid because residual hydrostatic pressure is dissipated by the flow of fluid via second conduit portion 11 into the waste chamber 44. In a second step, operation of a pump means applies pressure to air bladder 43, forcing air through conduit 40, through cutaways 17 and 18, and into conduit 34 at a predetermined location 27. Capillary stop 25 and location 27 delimit a metered portion of the original sample. While the sample is within sample holding chamber 34, it is amended with the dry reagent coating comprising one or more leukocidal reagents and optionally sacrificial beads and any other desired materials on the inner surface of the chamber. The metered portion of the sample is then expelled through the capillary stop by air pressure produced within air bladder 43. The sample passes into conduit 15 and into contact with the analyte sensor or sensors located within cutaway 35.

In embodiments employing an immunosensor located within cutout 35, the sample is amended prior to arriving at the sensor by, for example, an enzyme-antibody conjugate (signal antibody). To promote efficient binding of the analyte to the sensor, the sample containing the analyte is optionally passed repeatedly over the sensor in an oscillatory motion. Preferably, an oscillation frequency of between about 0.2 and 2 Hz is used, most preferably 0.7 Hz. Thus, the signal enzyme associated with the signal antibody is brought into close proximity to the amperometric electrode surface in proportion to the amount of analyte present in the sample.

Once an opportunity for the analyte/enzyme-antibody conjugate complex to bind to the immunosensor has been provided, the sample is ejected by further pressure applied to air bladder 43, and the sample passes to waste chamber 44. A wash step next removes non-specifically bound enzyme-conjugate and sacrificial beads from the sensor chamber. Fluid in the second conduit is moved by a pump means 43, into contact with the sensors. The analysis fluid is pulled slowly until the first air segment is detected at a conductivity sensor.

Figure 14:
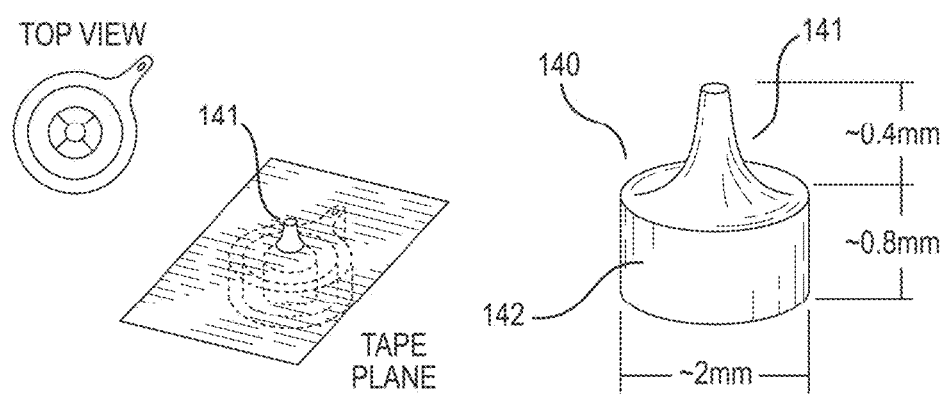
FIG. 14 illustrates a segment forming means.

The air segment or segments can be produced within a conduit by any suitable means, including but not limited to: (1) passive means, as shown in FIG. 14 and described below;

(2) active means including a transient lowering of the pressure within a conduit using a pump whereby air is drawn into the conduit through a flap or valve; or (3) by dissolving a compound pre-positioned within a conduit that liberates a gas upon contacting fluid in the conduit, where such compound may include a carbonate, bicarbonate or the like. This segment is extremely effective at clearing the sample-contaminated fluid from conduit 15. The efficiency of the rinsing of the sensor region is greatly enhanced by the introduction of one or more air segments into the second conduit as described. The leading and/or trailing edges of air segments are passed one or more times over the sensors to rinse and re-suspend extraneous material that may have been deposited from the sample. Extraneous material includes any material other than specifically bound analyte or analyte/antibody-enzyme conjugate complex. However, it is an object of the invention that the rinsing is not sufficiently protracted or vigorous as to promote dissociation of specifically bound analyte or analyte/antibody-enzyme conjugate complex from the sensor.

Another advantage of introducing air segments into the fluid is to segment the fluid. For example, after a first segment of the fluid is used to rinse a sensor, a second segment is then placed over the sensor with minimal mixing of the two segments. This feature further reduces background signal from the sensor by more efficiently removing unbound antibody-enzyme conjugate. After the front edge washing, the analysis fluid is pulled slowly until the first air segment is detected at a conductivity sensor. This segment is extremely effective at clearing the sample-contaminated fluid which was mixed in with the first analysis fluid sample. For measurement, a new portion of fluid is placed over the sensors, and the current or potential, as appropriate to the mode of operation, is recorded as a function of time.

Example 3

Figure 15:
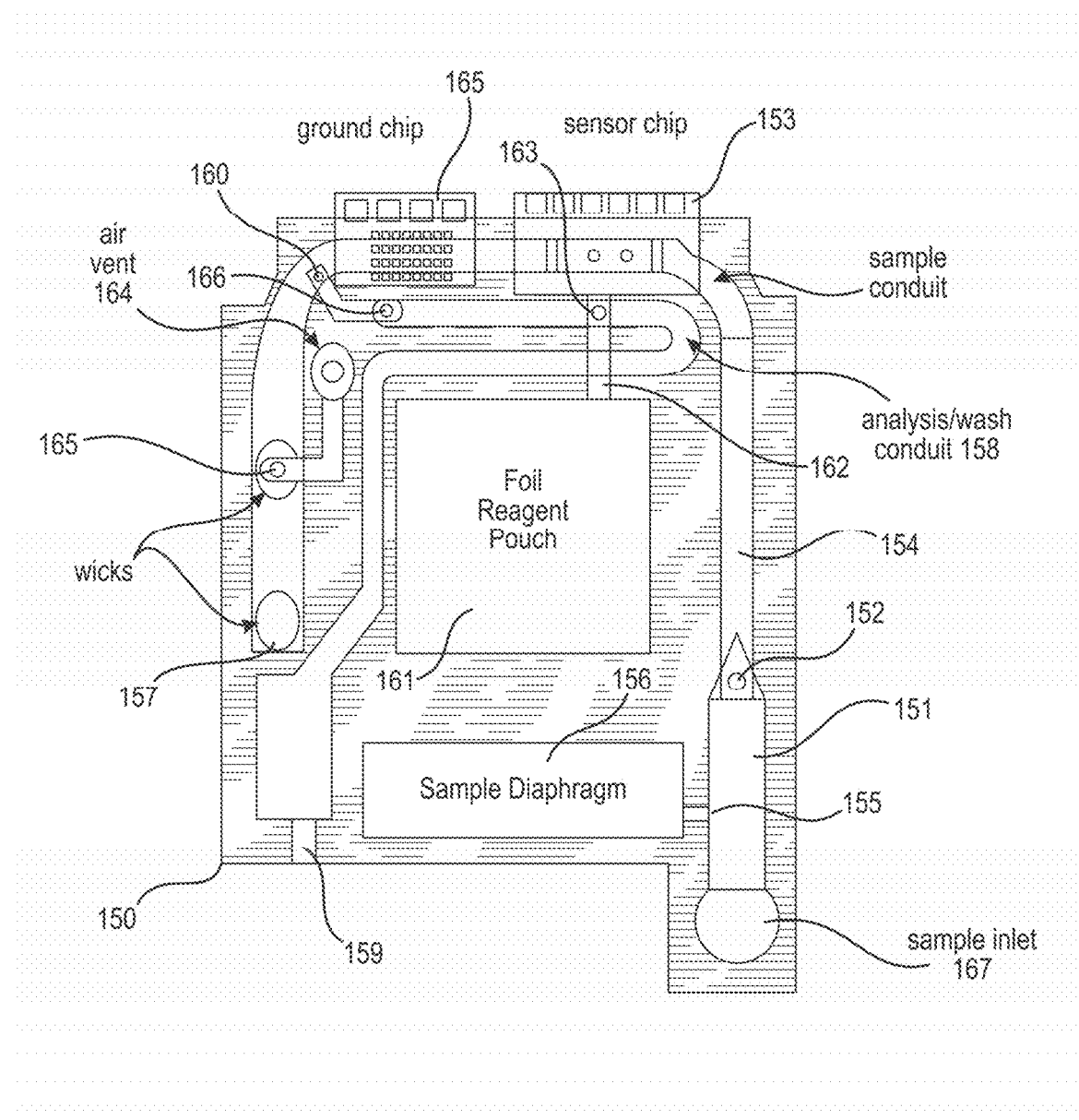
FIG. 15 is a top view of the preferred embodiment of an immunosensor cartridge.

Referring now to FIG. 15, there is shown a top view of an immunosensor cartridge. Cartridge 150 comprises a base and a top portion, preferably constructed of a plastic. The two portions are connected by a thin, adhesive gasket or thin pliable film. As in previous embodiments, the assembled cartridge comprises a sample holding chamber 151 into which a sample containing an analyte of interest is introduced via a sample inlet 167. A metered portion of the sample is delivered to the sensor chip 153, via the sample conduit 154 (first conduit) as before by the combined action of a capillary stop 152, preferably formed by a 0.012 inch (0.3 mm) laser cut hole in the gasket or film that connects the two portions of the cartridge, and an entry point 155 located at a predetermined point within the sample holding chamber whereby air introduced by the action of a pump means, such as a paddle pushing upon a sample diaphragm 156. After contacting the sensor to permit binding to occur, the sample is moved to vent 157, which contains a wicking material that absorbs the sample and thereby seals the vent closed to the further passage of liquid or air. The wicking material is preferably a cotton fiber material, a cellulose material, or other hydrophilic material having pores. It is important in the present application that the material is sufficiently absorbent (i.e., possesses sufficient wicking speed) that the valve closes within a time period that is commensurate with the subsequent withdrawal of the sample diaphragm actuating means described below, so that sample is not subsequently drawn back into the region of the sensor chip.

As in the specific embodiment shown, there is provided a wash conduit (second conduit) 158, connected at one end to a vent 159 and at the other end to the sample conduit at a point 160 of the sample conduit that is located between vent 157 and sensor chip 153. Upon insertion of the cartridge into a reading apparatus, a fluid is introduced into conduit 158. Preferably, the fluid is present initially within a foil pouch 161 that is punctured by a pin when an actuating means applies pressure upon the pouch. There is also provided a short conduit 162 that connects the fluid to conduit 154 via a small opening in the gasket 163. A second capillary stop initially prevents the fluid from reaching capillary stop 160, so that the fluid is retained within conduit 158.

After vent 157 has closed, the pump is actuated, creating a lowered pressure within conduit 154. Air vent 164, preferably comprising a small flap cut in the gasket or a membrane that vibrates to provide an intermittent air stream, provides a means for air to enter conduit 158 via a second vent 165. The second vent 165 preferably also contains wicking material capable of closing the vent if wetted, which permits subsequent depression of sample diaphragm 156 to close vent 165, if required. Simultaneously with the actuation of sample diaphragm 156, fluid is drawn from conduit 158, through capillary stop 160, into conduit 154. Because the flow of fluid is interrupted by air entering vent 164, at least one air segment (a segment or stream of segments) is introduced.

Further withdrawal of sample diaphragm 156 draws the liquid containing at least one air segment back across the sensing surface of sensor chip 153. The presence of air-liquid boundaries within the liquid enhances the rinsing of the sensor chip surface to remove remaining sample. Preferably, the movement of the sample diaphragm 156 is controlled in conjunction with signals received from the conductivity electrodes housed within the sensor chip adjacent to the analyte sensors. In this way, the presence of liquid over the sensor is detected, and multiple readings can be performed by movement of the fluid in discrete steps.

It is advantageous in this embodiment to perform analyte measurements when only a thin film of fluid coats the sensors, ground chip 165, and a contiguous portion of the wall of conduit 154 between the sensors and ground electrode. A suitable film is obtained by withdrawing fluid by operation of the sample diaphragm 156, until the conductimetric sensor located next to the sensor indicates that bulk fluid is no longer present in that region of conduit 154. It has been found that measurement can be performed at very low (nA) currents, the potential drop that results from increased resistance of a thin film between ground chip and sensor chip (compared to bulk fluid), is not significant.

The ground chip 165 is preferably silver/silver chloride. It is advantageous, to avoid air segments, which easily form upon the relatively hydrophobic silver chloride surface, to pattern the ground chip as small regions of silver/silver chloride interspersed with more hydrophilic regions, such as a surface of silicon dioxide. Thus, a preferred ground electrode configuration comprises an array of silver/silver chloride squares densely arranged and interspersed with silicon dioxide. There is a further advantage in the avoidance of unintentional segments if the regions of silver/silver chloride are somewhat recessed.

Figure 16:
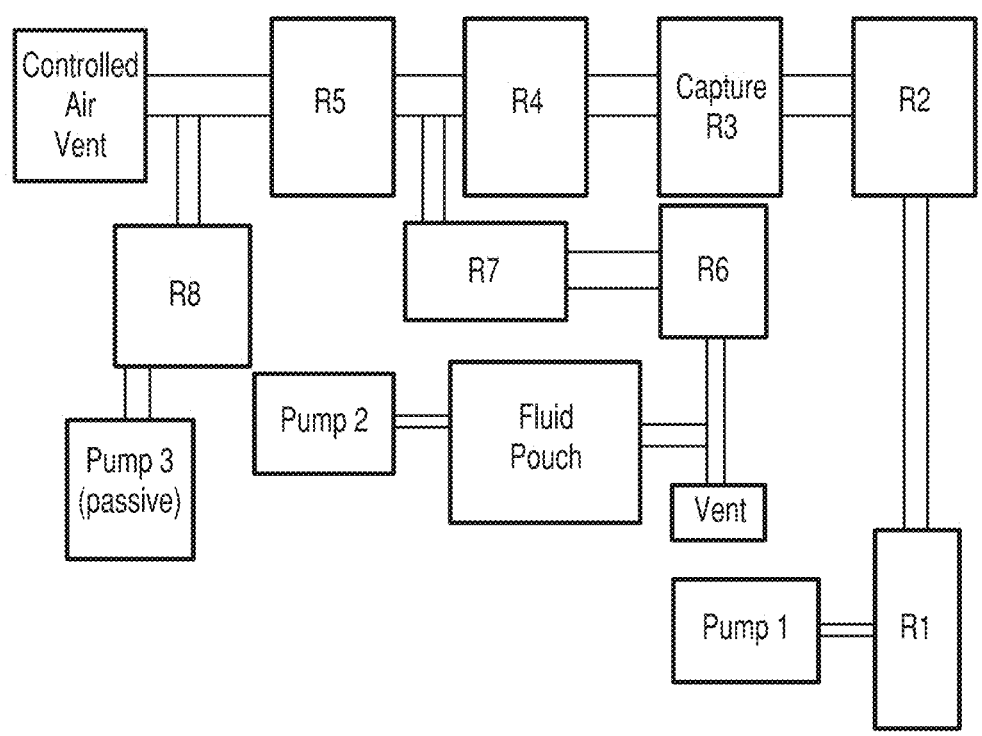
FIG. 16 is a schematic view of the fluidics of a preferred embodiment of an immunosensor cartridge.

Referring now to FIG. 16, there is shown a schematic view of the fluidics of the preferred embodiment of an immunosensor cartridge. Regions R1-R7 represent specific regions of the conduits associated with specific operational functions. Thus R1 represents the sample holding chamber; R2 the sample conduit whereby a metered portion of the sample is transferred to the capture region, and in which the sample is optionally amended with a substance coated upon the walls of the conduit, e.g., one or more leukocidal reagents and optionally opsonized sacrificial beads; R3 represents the capture region, which houses the conductimetric and analyte sensors; R4 and R5 represent portions of the first conduit that are optionally used for further amendment of fluids with substances coated onto the conduit wall, whereby more complex assay schemes are achieved; R6 represents the portion of the second conduit into which fluid is introduced upon insertion of the cartridge into a reading apparatus; R7 comprises a portion of the conduit located between capillary stops 160 and 166, in which further amendment can occur; and R8 represents the portion of conduit 154 located between point 160 and vent 157, and which can further be used to amend liquids contained within.

Example 4

With regard to the coordination of fluidics and analyte measurements, during the analysis sequence, a user places a sample into the cartridge, places the cartridge into the analyzer and in from 1 to 20 minutes, a quantitative measurement of one or more analytes is performed. A non-limiting example of a sequence of events that occur during the analysis is as follows:

(1) A 25 to 50 µL sample is introduced in the sample inlet 167 and fills to a capillary stop 151 formed by a 0.012 inch (0.3 mm) laser cut hole in the adhesive tape holding the cover and base components together. One or more dry reagent coatings comprising one or more leukocidal reagents and optionally opsonized sacrificial beads plus optionally other materials for ameliorating interference and preferably a signal antibody are dissolved into the sample. The user rotates a latex rubber disk mounted on a snap flap to close the sample inlet 167 and places the cartridge into the analyzer.

(2) The analyzer makes contact with the cartridge, and a motor driven plunger presses onto the foil pouch 161 forcing the wash/analysis fluid out into a central conduit 158.

(3) A separate motor driven plunger contacts the sample diaphragm 156 pushing a measured segment of the sample along the sample conduit (from reagent region R1 to R2). The sample is detected at the sensor chip 153 via the conductivity sensors. The sensor chip is located in capture region R3.

(4) The sample is oscillated by means of the sample diaphragm 156 between R2 and R5 in a predetermined and controlled fashion for a controlled time to promote binding to the sensor.

(5) The sample is pushed towards the waste region of the cartridge (R8) and comes in contact with a passive pump 157 in the form of a cellulose or similar absorbent wick. The action of wetting this wick seals the wick to air flow thus eliminating its ability to vent excess pressure generated by the sample diaphragm 156. The active vent becomes the "controlled air vent" of FIG. 16.

(6) Rapid evacuation of the sample conduit (effected by withdrawing the motor driven plunger from the sample diaphragm 156) forces a mixture of air (from the vent) and wash/analysis fluid from the second conduit to move into the inlet located between R5 and R4 in FIG. 16. By repeating the rapid evacuation of the sample conduit, a series of air separated fluid segments are generated which are pulled across the sensor chip towards the sample inlet (from R4 to R3 to R2 and R1). This washes the sensor free of excess reagents and wets the sensor with reagents appropriate for the analysis. The wash/analysis fluid which originates in the foil pouch can be further amended by addition of reagents in R7 and R6 within the central wash/analysis fluid conduit.

(7) The wash/analysis fluid segment is drawn at a slower speed towards the sample inlet to yield a sensor chip which contains only a thin layer of the analysis fluid. The electrochemical analysis is performed at this point. The preferred method of analysis is amperometry but potentiometry or impedance detection is also used.

(8) And the mechanism retracts allowing the cartridge to be removed from the analyzer.

Example 5

In some embodiments, the device employs an immunoreference sensor for purposes of assessing the degree of nonspecific binding occurring during an assay. The immunoreference sensor is fabricated in much the same way as the analyte immunosensor with the exception that the immuno reagent is an anti-HSA (human serum albumin) antibody rather than an anti-analyte antibody. Upon exposure to a human whole blood or plasma sample, the reference sensor becomes coated with specifically bound HSA, an abundant endogenous protein present in all human blood samples thus affording a common reference for all individual tests run using the present immunoassay format. NSB arising due to inadequate washing or due to the presence of interferences can be monitored by means of this second sensor.

The net signal from the assay is comprised of the specific signal arising from the analyte immunosensor corrected by subtracting the non-specific signal arising from the reference sensor, e.g., Net Signal=Analyte Sensor Signal−Reference Sensor Signal−Offset, as shown in equation 4 above. The "offset" is a coefficient that accounts for the difference in the tendency of the two sensors to be subject to NSB. In effect, it accounts for the relative "stickiness" of each sensor with respect to their ability to bind conjugate non-specifically and is established based on the responses of samples that are free of analyte and free of interference. This is done by independent experimentation.

The amount of signal tolerated at the reference sensor is subject to limits defined by a quality control algorithm that seeks to safeguard the integrity of results at low analyte concentration where the effects of NSB have the greatest potential to affect assay results in a manner that can alter decision-making in a clinical environment. The essential principal is that the existence of excessive signal at the reference sensor acts as a flag for the presence of NSB, due either to an inadequate wash step or interference.

Example 6

The experiments described below were performed on a BNP assay, specifically an i-STAT® BNP cartridge (Abbott Point of Care, Princeton, N.J., USA) or a partially modified version thereof.

In all of these embodiments, the use of one or more leukocidal reagents and optionally beads opsonized for leukocytes, as described elsewhere in this application may be integrated into the assay, for example the sample may be amended with both glucose oxidase, and with beads opsonized for leukocytes, and optionally glucose and saponin. Generally the sample is a whole blood sample, e.g., venous, arterial and capillary, which may or may not have been amended with an anticoagulant.

As an experimental aid to understanding the affect of leukocytes on whole-blood immunoassays, it is desirable to create an enriched buffy (blood) sample (EBS). The method adopted here was to take a spun tube of blood, with plasma at the top, red cells at the bottom and a thin buffy coat in between. About half or more of the plasma and red cells were then removed by pipette, and the sample remixed. In the experiments described herein, the EBS constituted approximately a ten-fold increase in the buffy concentration, i.e. roughly 90% of the plasma and red cells were removed. The hematocrit value (Hct) of the sample was therefore maintained in the normal range, roughly 50-60%.

Figure 26:
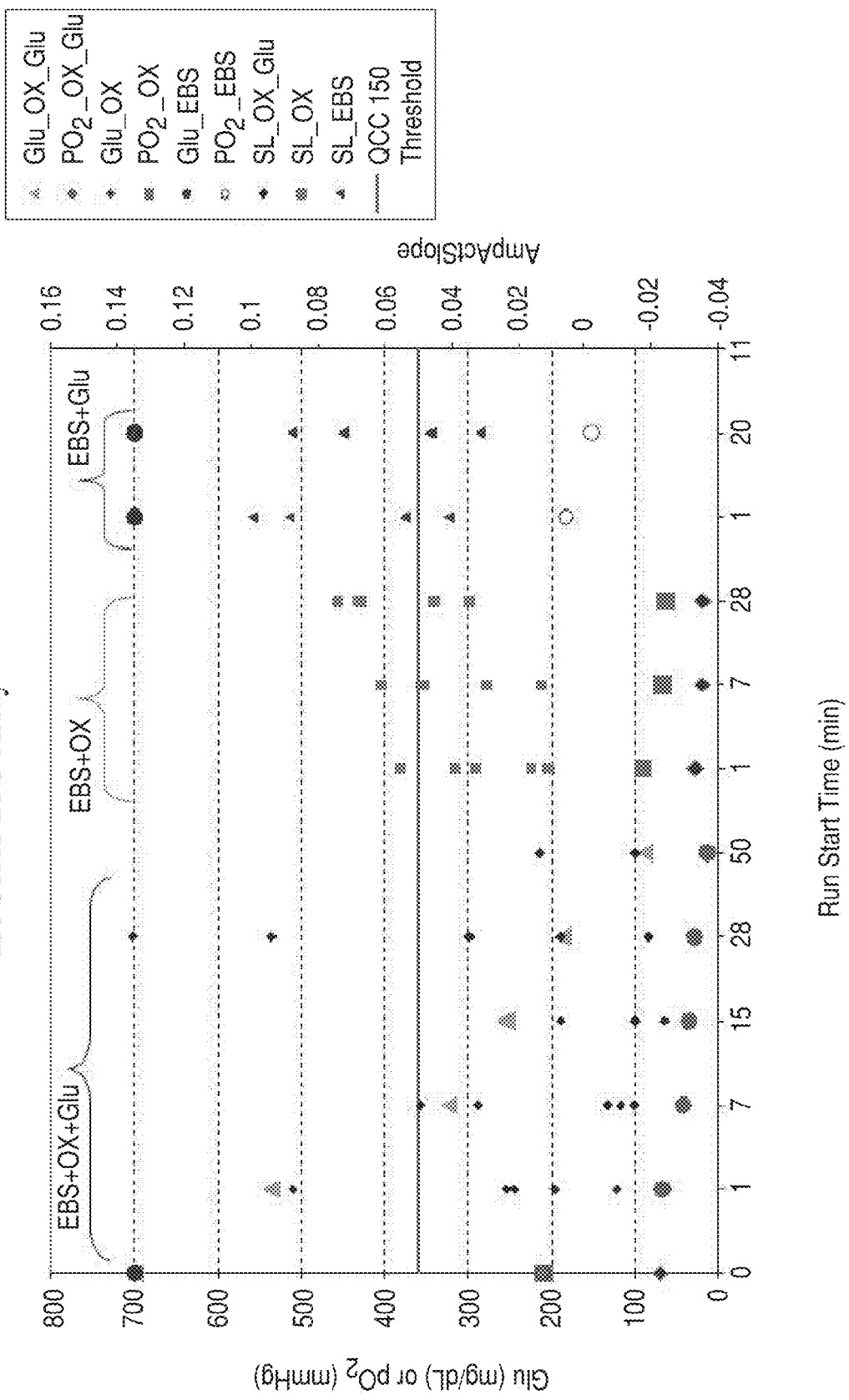
FIG. 26 shows the use of glucose oxidase in reducing the effect of leukocyte activity on the signal output slope of an immunosensor.

FIG. 26 shows the effect of glucose oxidase on leukocyte activity. As a baseline indicator of leukocyte interference, a cut-off value of a signal rate of change above 0.05 nA per second, was used (see right side y-axis, AmpActSlope). The data sets are broken into three groups EBS+OX+Glu, EBS+OX and EBS+Glu, where OX is glucose oxidase at a concentration of 4.0 IU per mL and Glu is glucose at a concentration of 700 mg/dL. In the first group the enzyme is anticipated to remove substantially all the oxygen and the co-reactant glucose is added in substantial excess. The second group relies on glucose already in the sample to react with the enzyme. The third group is a control with added glucose and no enzyme.

The left side of the y-axis in FIG. 26 shows both the glucose (mg/dL) and oxygen ($PO_2$ mm Hg) concentrations. The x-axis of FIG. 26 shows the "run start time," which is the time between mixing the samples in each group above, and taking an aliquot of that sample and injecting it into a cartridge. Note that i-STAT® CG8+ cartridges (Abbott Point of Care, New Jersey, USA) were used to determine the glucose and oxygen concentrations.

With respect to the first group (EBS+OX+Glu), the initial oxygen concentration of about 200 mm Hg falls to about 10 mm Hg after 50 minutes, and the glucose concentration drops from 700 to about 100 mg/dL over the same period. During this period immunoassays were run to determine the AmpActSlope value. In this group 16 out of 19 assayed samples had slopes below 0.05 nA per second. The AmpActSlope value is obtained from the analysis of current versus time signal traces, as shown in FIG. 25.

Figure 25:
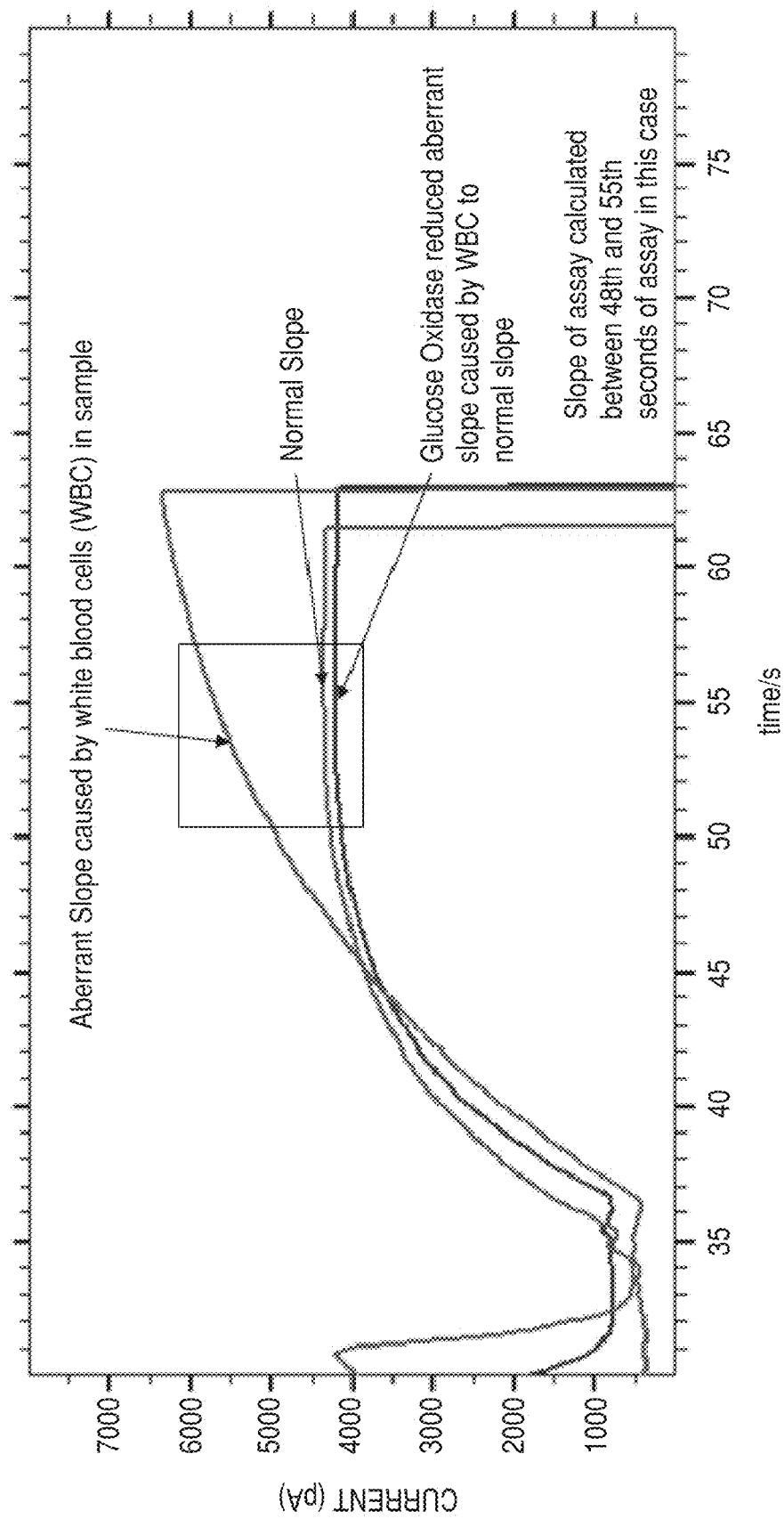
FIG. 25 shows current versus time plots for immunosensors.

As shown in FIG. 25, the first trace beyond about the 50 second point is a steady current value, typical of a sample with a low or normal leukocyte activity towards the immunosensor. Specifically, the immunosensor included a BNP immunosensor comprising a first capture antibody on bead attached to an electrode and a second signal antibody labeled with ALP. A general description of this type of immunosensor and immunoassay cartridge is found in U.S. Pat. No. 7,419,821 to Davis et al. The rate of change in the current is substantially less than the preferred threshold value of 0.05 nA per second. The second trace is typical of a sample with a high leukocyte activity towards the immunosensor, e.g., EBS. The rate of change in the current is greater than the preferred threshold value of 0.05 nA per second. The third trace beyond about the 50 second point is a steady current value, typical of an EBS that has been treated with a combination of glucose and glucose oxidase to reduce leukocyte activity towards the immunosensor. Note that the rate of change in the current is once again substantially less than the preferred threshold value of 0.05 nA per second.

With respect to the second group (EBS+OX), the oxygen concentration only drops down (from about 200 mm Hg) to about 50 mm Hg and the glucose concentration drops rapidly below about 20 mg/dL indicating that there is insufficient glucose in the sample to consume all the oxygen. This observation is related to the red blood cells acting as an oxygen buffer, i.e., releasing more oxygen as the plasma concentration falls. During this period immunoassays were also run to determine the AmpActSlope value. In this group, 9 out of 13 assayed samples had slopes below 0.05 nA per second.

With respect to the third group (EBS+Glu), the oxygen concentration only drops slightly and the glucose concentration remains roughly unchanged. During this period immunoassays were run to determine the AmpActSlope value. In this group, 3 out of 8 assayed samples had slopes below 0.05 nA per second.

Based on the data from the three groups, it is clear that glucose oxidase can help contribute to a reduction in leukocyte activity and that this is enhanced by the addition of excess glucose to the sample. It was found that a glucose oxidase concentration in excess of about 3 IU per mL in the sample was preferable for venous samples and addition of glucose to give an initial sample concentration of above about 500 mg/dL was preferable.

Figure 27:
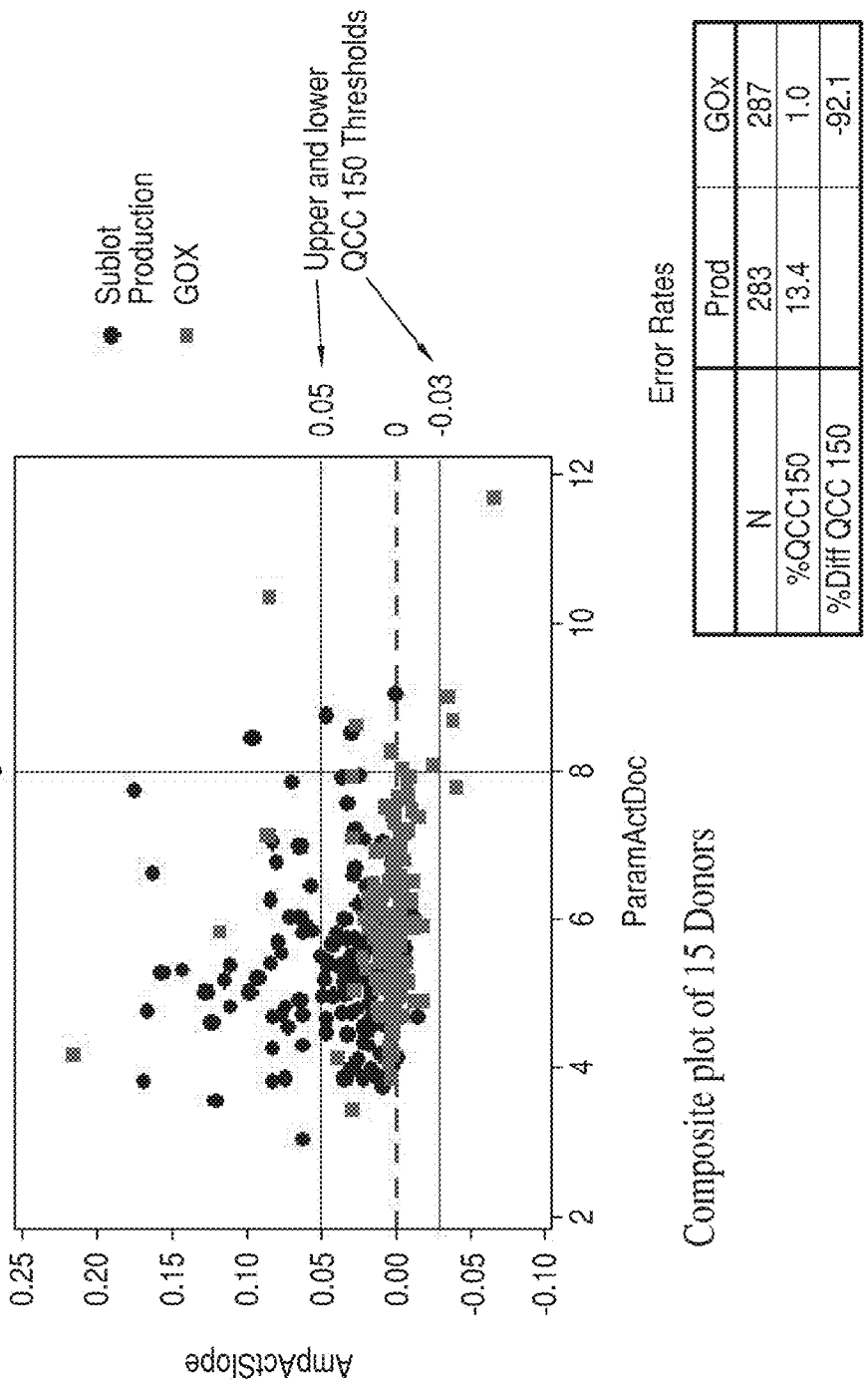
FIG. 27 shows a scatter plot for untreated and treated samples and the effect of leukocyte activity on the signal output slope.

To further characterize these effects, a study was run on a larger sample donor pool (15 donors multiple runs), as shown in FIG. 27. FIG. 27 is a scatter plot where the desirable AmpActSlope value is less than 0.05 and greater than −0.03 nA per second. In addition, in this particular experiment a maximum desirable sensor threshold current (ParamActDoc) was also set at 8.0 nA. The desirable result was therefore to minimize samples falling into the five segments around the target zone. Treated EBS+OX samples (squares) clearly show superior performance to untreated samples (circles); treated N=287, 1.0% beyond threshold; untreated N=283, 13.4% beyond threshold; giving a 92.1% difference. Based on the experimental results, in general, the addition of the glucose oxidase reduces the number of assays where a slope above the desirable threshold is observed by about 90%. This is a significant improvement in overall assay quality and performance.

Those skilled in the art will recognize that while the present invention is described in terms of a specific amperometric sensor used in an immunoassay, other parameters than AmpActSlope measured as delta nA per second may be used as a determinant of leukocyte interference, e.g., absolute current value, signal noise as fraction of signal strength and the like. In addition, the present invention is equally relevant to other immunosensors, including electrochemical immunosensors based on potentiometric and conductimetric measurements, and non-electrochemical immunosensors, e.g., surface acoustic wave, surface plasmon resonance, optical waveguides and the like. Each of these has known criteria for assessing adverse effects on sensor performance. These can be assessed for suitability using the EBS method, or variants thereof.

Figure 28B:
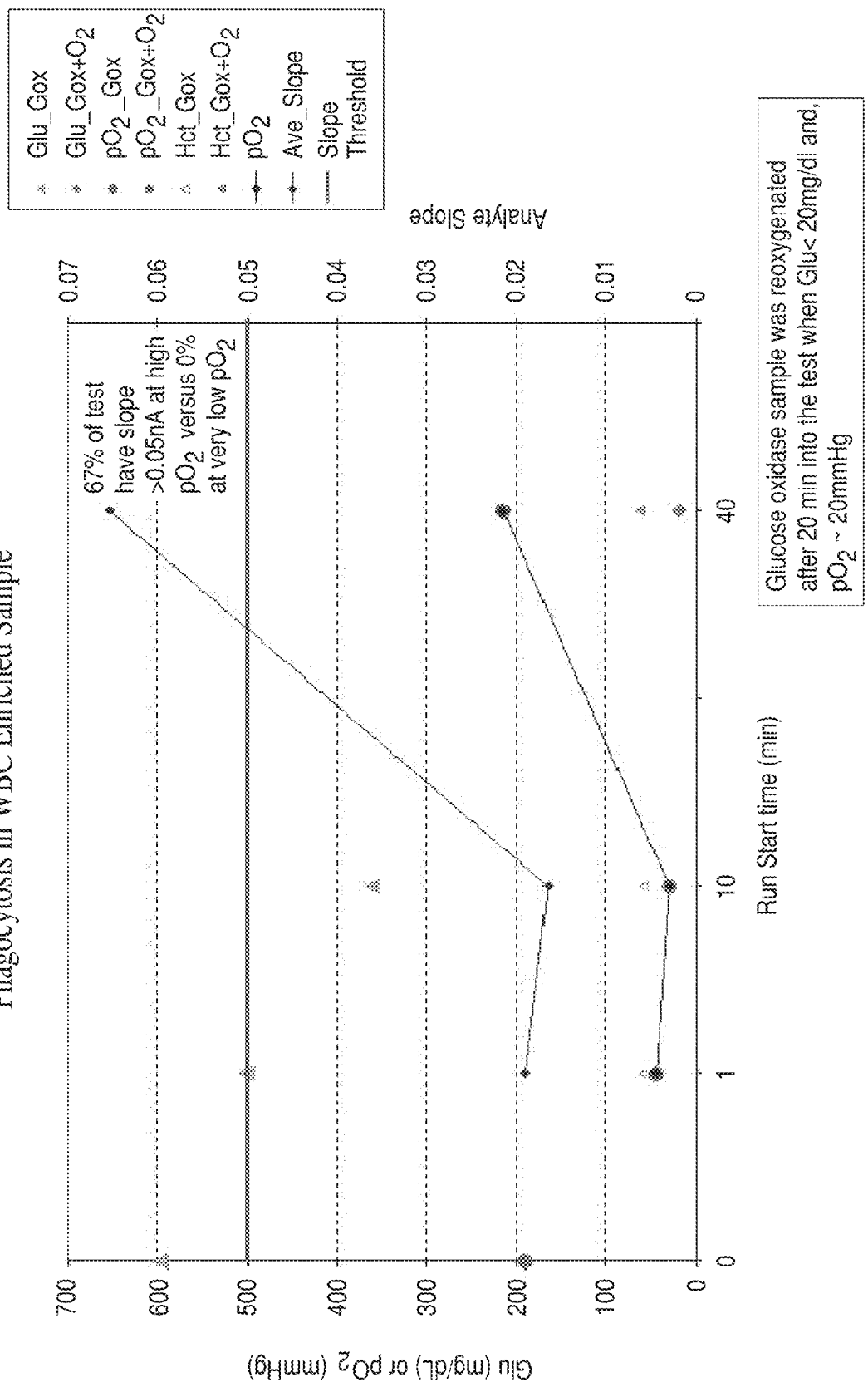
FIG. 28(b) shows the use of glucose oxidase in reducing the effect of leukocyte activity on the signal output slope of an immunosensor where the sample is retained in a closed container versus open to ambient air.

FIG. 28A shows an additional study that was performed to further characterize the use of EBS+OX+Glu treated samples. The "Sample 2" set of data was obtained where the treatment occurs in a closed syringe to prevent any oxygen being introduced from ambient air. Over ten minutes the oxygen dropped from about 200 mm Hg to about 20 mm Hg and the glucose dropped from about 600 to about 360 mg/dL. All 12 consecutive immunoassays run on the sample had desirable AmpActSlope values below 0.05 nA per second. The "Sample 3" data reflects opening the syringe about 20 minutes after the initial runs to allow ambient air access. This sample was run at the 40 minute mark. Here, the leukocytes are no longer deprived of oxygen and an increased number of immunoassay tests show AmpActSlope values above the desired threshold. The "Sample 1" data in FIG. 28A is a control EBS+Glu only. FIG. 28B presents the data in a simpler form with the points at run times of 1 and 10 minutes being those of the syringe samples and those at 40 minutes being the same sample after re-oxygenation by exposure to air.

While it is more common for a blood sample used in an immunoassay performed in a laboratory to be drawn from a vein, where point-of-care (or bedside, e.g. Emergency Room, Operating Room) testing is done, it is not uncommon for the sample to be drawn from an artery. Obviously the $PO_2$ concentration will generally be higher in the latter type of sample. To assess the impact of an arterial sample on the present assay, simulated arterial samples were generated and tested. Those skilled in the art will recognize that directly obtaining arterial samples involves a much higher risk of internal bleeding, hence the use of simulated samples. Simulated samples were created with a tonometer using venous blood collected in an EDTA tube. The tonometer equilibrates the blood with a predetermined gas composition.

FIG. 29 shows data for the simulated arterial samples. Note these samples were not enriched as described above. The first column of data (WB) indicates that the tonometered whole blood sample had an initial $PO_2$ of about 150 mm Hg and an initial glucose value of about 70 mg/dL, and that neither changed significantly over a period of eight minutes. Addition of glucose oxidase at both 6 and 12 IU per mL (see WB+6 and WB+12 columns) resulted in both decreased glucose and $PO_2$. As anticipated in the fourth column WB+Glu, the glucose was elevated and the $PO_2$ remained substantially unchanged. Both the fifth and sixth columns (WB+6+Glu and WB+12+Glu) showed drops in $PO_2$ and glucose. As illustrated in FIG. 29, adding glucose oxidase at 6.0 IU and 12.0 IU per mL (and preferably in excess of about 3.0 IU per mL), is sufficient to inhibit phagocytosis in arterial blood through its ability to reduce the partial pressure of oxygen in the sample below about 50 mm Hg.

Example 7

Figure 30:
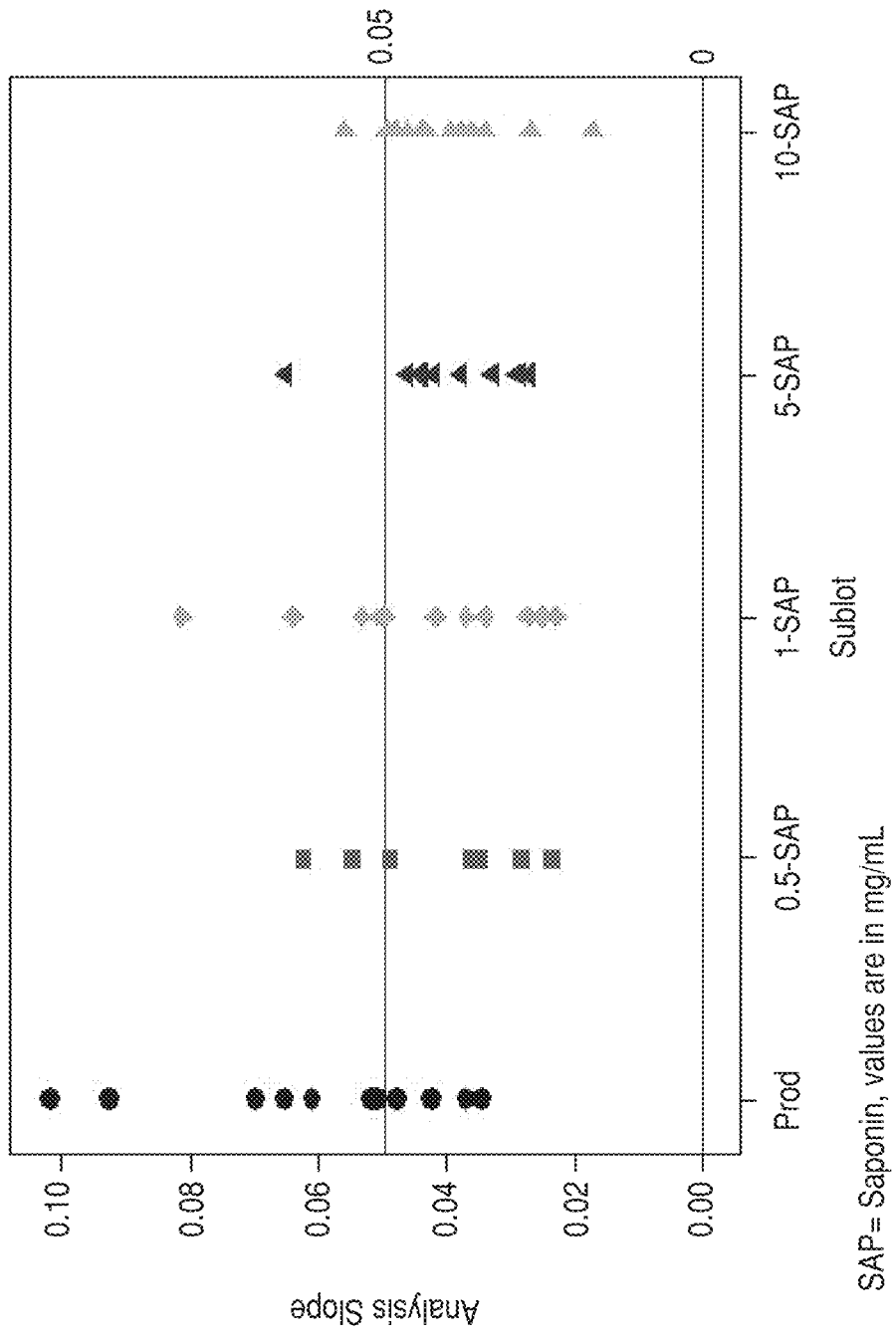
FIG. 30 shows the mitigation of phagocytosis in whole blood samples by using saponin.

As described herein, the use of saponin as a leukocidal reagent is an alternative method for inhibiting the activity of leukocytes. FIG. 30 shows the effect of added saponin (x-axis values in mg/mL in the range 0 to 10 mg/mL) against the analysis slope with the threshold value of 0.05 nA per second indicated for EBS samples. This study shows that samples with 0.5 mg/mL of saponin exhibit significantly fewer slopes above the threshold than untreated samples (Prod). FIG. 30 also shows similar results at concentrations up to 10 mg/mL. In other experiments it was found that saponin concentrations in the range of about 0.1 to 20 mg/mL were useful in reducing leukocyte activity. It was also found that saponin may have an effect on the precision of the assay, that was ameliorated by repeated wash cycles. Consequently, in certain applications lower but effective saponin concentrations around 0.5 to 1.0 mg/mL may be preferred.

While the present invention as described above is generally directed to reducing or eliminating interference from leukocytes in an analyte immunoassay with a whole blood sample, it is also applicable to immunoassays performed in other types of biological samples where leukocytes may be present, e.g., cerebrospinal fluid. In addition it is applicable to samples where residual leukocytes may be present despite an intention to remove them by centrifugation or filtration, e.g., plasma. It is also applicable to samples that may have been diluted, e.g., with a buffer. Furthermore, while the invention is generally directed to amending the sample by dissolving into the sample a dry reagent, it is also practical in other embodiments to add the reagent, e.g., the one or more leukocidal reagents, as a liquid to the sample during the analysis or during sample collection. It is also apparent that the present invention has been described herein in terms of electrochemical detection approaches, e.g., amperometric and potentiometric approaches, although it is equally applicable to other detection modes, notably optical sensing approaches such as luminescence, fluorescence and absorbance based approaches.

While the invention has been described in terms of various preferred embodiments, those skilled in the art will recognize that various modifications, substitutions, omissions and changes can be made without departing from the spirit of the present invention. For example, while portions of the description are directed to non-competitive sandwich immunoassays, the devices and processes of the invention similarly may be employed in competitive immunoassays. Additionally, it is intended that the scope of the present invention be limited solely by the scope of the following claims.

What is claimed is:

1. A method of performing an electrochemical immunoassay for a target analyte in a whole blood sample comprising:
    contacting the whole blood sample with a leukocidal reagent, wherein said leukocidal reagent substantially inhibits phagocytic activity of leukocytes in the whole blood sample, and wherein the leukocidal reagent is a mitochondrial electron transport inhibitor or a mitochondrial membrane uncoupling agent; and
    performing the electrochemical immunoassay on the leukocidal reagent-treated whole blood sample, at an immunosensor and detecting the target analyte.

2. The method of claim 1, wherein the leukocidal reagent is the mitochondrial electron transport inhibitor.

3. The method of claim 1, wherein the leukocidal reagent is the mitochondrial membrane uncoupling agent.

4. The method of claim 1, wherein the leukocidal reagent is the mitochondrial electron transport inhibitor or the mitochondrial membrane uncoupling agent and selected from the group consisting of cyanide, antimycin, rotenone, malonate, carbonyl cyanide p-[trifluoromethoxyl]-phenyl-hydrozone, 2,4-dinitrophenol, and oligomycin.

5. The method of claim 1, wherein the electrochemical immunoassay is a sandwich assay performed by contacting the leukocidal reagent-treated whole blood sample with the immunosensor comprising an immobilized first antibody to the target analyte, and a labeled second antibody to the target analyte.

6. The method of claim 1, wherein the electrochemical immunoassay is a competitive assay performed by contacting the leukocidal reagent-treated whole blood sample with the immunosensor comprising an immobilized first antibody to the target analyte, and a labeled target analyte.

7. The method of claim 1, wherein the leukocidal reagent-treated whole blood sample is contacted with beads opsonized for the leukocytes.

8. The method of claim 1, wherein the whole blood sample is amended with an anticoagulant.

9. The method of claim 1, wherein the target analyte is selected from the group consisting of Troponin I (TnI), Troponin T (TnT), Brain Natriuretic Peptide (BNP), N-terminal of the Prohormone Brain Natriuretic Peptide (NT-proBNP), Prohormone Brain Natriuretic Peptide (proBNP), Human Chorionic Gonadotropin (HCG), Thyroid-Stimulating Hormone (TSH), Neutrophil Gelatinase Associated Lipocalin (NGAL), theophylline, digoxin, and phenytoin.

* * * * *